United States Patent
Erikson et al.

(10) Patent No.: US 7,309,569 B2
(45) Date of Patent: *Dec. 18, 2007

(54) PARALLEL OR ANTIPARALLEL, HOMOLOGOUS OR COMPLEMENTARY BINDING OF NUCLEIC ACIDS OR ANALOGUES THEREOF TO FORM DUPLEX, TRIPLEX OR QUADRUPLEX COMPLEXES

(75) Inventors: Glen H. Erikson, Providenciales (TC); Jasmine I. Daksis, Richmond Hill, CA (US); Ivana Kandic, Toronto (CA); Pierre Picard, Ottawa (CA)

(73) Assignee: Ingeneus, Inc., Belize (BZ)

(*) Notice: Subject to any disclaimer, the term of this patent is extended or adjusted under 35 U.S.C. 154(b) by 546 days.

This patent is subject to a terminal disclaimer.

(21) Appl. No.: 10/293,148

(22) Filed: Nov. 12, 2002

(65) Prior Publication Data
US 2005/0014140 A1    Jan. 20, 2005

Related U.S. Application Data

(63) Continuation-in-part of application No. 09/909,496, filed on Jul. 20, 2001, now Pat. No. 6,656,692, and a continuation-in-part of application No. 09/664,827, filed on Sep. 19, 2000, now Pat. No. 6,900,300, and a continuation-in-part of application No. 09/613,263, filed on Jul. 10, 2000, now Pat. No. 6,420,115, which is a continuation-in-part of application No. 09/468,679, filed on Dec. 21, 1999, now Pat. No. 6,403,313.

(51) Int. Cl.
C12Q 1/68 (2006.01)
C07H 21/04 (2006.01)

(52) U.S. Cl. .......................... 435/6; 536/23.1

(58) Field of Classification Search ...................... 435/6
See application file for complete search history.

(56) References Cited

U.S. PATENT DOCUMENTS

| | | | |
|---|---|---|---|
| 4,220,450 A | 9/1980 | Maggio | |
| 4,876,187 A | 10/1989 | Duck et al. | |
| 4,963,477 A | 10/1990 | Tchen | |
| 5,011,769 A | 4/1991 | Duck et al. | |
| 5,332,659 A | 7/1994 | Kidwell | |
| 5,403,711 A | 4/1995 | Walder et al. | |
| 5,538,848 A | 7/1996 | Livak et al. | |
| 5,539,082 A | 7/1996 | Nielsen et al. | |
| 5,558,998 A | 9/1996 | Hammond et al. | |
| 5,660,988 A | 8/1997 | Duck et al. | |
| 5,705,346 A | 1/1998 | Okamoto et al. | |
| 5,707,801 A | 1/1998 | Bresser et al. | |
| 5,720,928 A | 2/1998 | Schwartz | |
| 5,731,146 A | 3/1998 | Duck et al. | |
| 5,783,063 A | 7/1998 | Clarkson et al. | |
| 5,800,984 A | 9/1998 | Vary | |
| 5,800,992 A | 9/1998 | Fodor et al. | |
| 5,814,447 A | 9/1998 | Ishiguro et al. | |
| 5,814,516 A | 9/1998 | Vo-Dinh | |
| 5,824,477 A | 10/1998 | Stanley | |
| 5,824,557 A | 10/1998 | Burke et al. | |
| 5,846,729 A | 12/1998 | Wu et al. | |
| 5,861,124 A | 1/1999 | Hosoi et al. | |
| 5,874,555 A | 2/1999 | Dervan et al. | |
| 5,888,739 A | 3/1999 | Pitner et al. | |
| 5,912,332 A | 6/1999 | Agrawal et al. | |
| 5,925,517 A * | 7/1999 | Tyagi et al. ........................ 435/6 |
| 5,948,897 A | 9/1999 | Sen et al. | |
| 6,013,442 A | 1/2000 | Kolesar et al. | |
| 6,017,709 A | 1/2000 | Hardin et al. | |
| 6,027,880 A | 2/2000 | Cronin et al. | |
| 6,046,004 A | 4/2000 | Wu et al. | |
| 6,048,690 A | 4/2000 | Heller et al. | |

(Continued)

FOREIGN PATENT DOCUMENTS

| | | |
|---|---|---|
| GB | 2333359 A | 7/1999 |
| GB | 2338301 A | 12/1999 |
| WO | WO 97/45539 A1 | 12/1997 |
| WO | WO 00/20633 A1 | 4/2000 |

OTHER PUBLICATIONS

Gaillard et al. Association of Double-stranded DNA Fragments into multistranded DNA structures. Biopolymers, vol. 50, pp. 679-689, 1999.*
ABSTRACT of JP 5237000, Yoshitami (Sep. 17, 1993).
Baran et al., *Nucleic Acids Research* 25:297-303 (1997).
Bohmann et al., *Science*, 238:1386-1392 (Dec. 1987).
Carlsson et al., 380 *Nature* 207 (Mar. 21, 1996).
Chan et al., *J. Mol. Med.* 75 Issue 4:267-282 (1997).
Dalrymple et al., *Nucleic Acids Research*, vol. 13, No. 21, pp. 7865-7879 (1985).

(Continued)

*Primary Examiner*—Gary Benzion
*Assistant Examiner*—Cynthia B Wilder
(74) *Attorney, Agent, or Firm*—Caesar, Rivise, Bernstein, Cohen & Pokotilow, Ltd.

(57) ABSTRACT

A complex includes: (1) a probe containing a heteropolymeric probe sequence of nucleic acids or nucleic acid analogues; and (2) a target containing a heteropolymeric target sequence of nucleic acids or nucleic acid analogues, wherein: (a) at least one of the probe and the target is purified or synthetic; and (b) the heteropolymeric probe sequence is bonded to the heteropolymeric target sequence by Watson-Crick complementary base interaction or by homologous base interaction, provided that when the complex is a duplex and the heteropolymeric probe sequence is antiparallel to the heteropolymeric target sequence, the heteropolymeric probe sequence is bonded to the heteropolymeric target sequence by homologous base interaction, and provided that when the complex is a triplex, the complex is free of recombination proteins. A method for assaying a target includes detecting formation of the complex.

47 Claims, 26 Drawing Sheets

U.S. PATENT DOCUMENTS

| | | | |
|---|---|---|---|
| 6,060,242 | A | 5/2000 | Nie et al. |
| 6,107,078 | A | 8/2000 | Keese et al. |
| 6,117,657 | A | 9/2000 | Usman et al. |
| 6,147,198 | A | 11/2000 | Schwartz |
| 6,251,591 | B1 | 6/2001 | Wu et al. |
| 6,255,050 | B1 | 7/2001 | Nie et al. |
| 6,265,170 | B1 | 7/2001 | Picard et al. |
| 6,287,772 | B1 | 9/2001 | Stefano et al. |
| 6,312,925 | B1 | 11/2001 | Meyer, Jr. et al. |
| 6,403,313 | B1 | 6/2002 | Daksis et al. |
| 6,420,115 | B1 | 7/2002 | Erikson et al. |
| 6,426,407 | B1 * | 7/2002 | Fresco et al. ............... 536/22.1 |
| 6,878,815 | B2 * | 4/2005 | Erikson et al. ............ 536/23.1 |

OTHER PUBLICATIONS

Durland et al., *Biochemistry*, 30:9246-9255 (1991).
Egholm et al., 365 *Nature* 566 (Oct. 7, 1993).
Floris et al., 260 *Eur. J. Biochem.* 801-809 (1999).
Giese et al., *Nature* 412, p. 318 (Jul. 19, 2001).
Hill et al., *Methods in Enzymology*, 278:390-416 (1997).
Johansen and Jacobsen, *J Biomol Struct Dyn*, 16(2):205-22 (Oct. 1998) (Abstract).
Kadonaga et al., *Cell*, 51:1079-1090 (Dec. 24, 1987).
Kukreti et al., *Nucleic Acids Research*, 25:4264-4270 (1997).
Leontis et al., *Nucleic Acids Research*, 30:(No. 16)3497-3531 (2002).
Marsh et al., *Nucleic Acids Research*, 23:696-700 (1995).
Marsh et al., *Biochemistry* 33:10718-10724 (1994).
Mazumder et al., *Biochemistry* 35:13762-13771 (1996).
Rocher et al., *Nucleic Acids Research*, "Initiation of DNA replication by DNA polymerases from primers forming a triple helix," vol. 29, No. 16, 3320-3326 (2001).
Sen et al., *Nature* 334:364-366 (1988).
Sen et al., *Biochemistry* 31:65-70 (1992).
Sturm et al., *Genes & Development*, 2:1582-1599 (1988).
Tomac et al., 118 *J. Am. Chem. Soc.* 5544-5552 (1996).
Watson, James, "A Personal Account of the Discovery of the Structure of DNA," (1968).
Williamson et al., *Cell* 59:871-880 (Dec. 1, 1989).
Wilson et al., *Cell*, 74:115-125 (Jul. 16, 1993).
Zhurkin et al., *J. Mol. Biol.*, vol. 239, 181-200 (1994).
U.S. Appl. No. 09/713,177, Erikson et al.
U.S. Appl. No. 09/885,731, Erikson et al.
U.S. Appl. No. 09/961,885, Erikson et al.
U.S. Appl. No. 10/080,767, Erikson et al.
U.S. Appl. No. 10/103,022, Erikson et al.
U.S. Appl. No. 10/269,229, Atkinson et al.

* cited by examiner

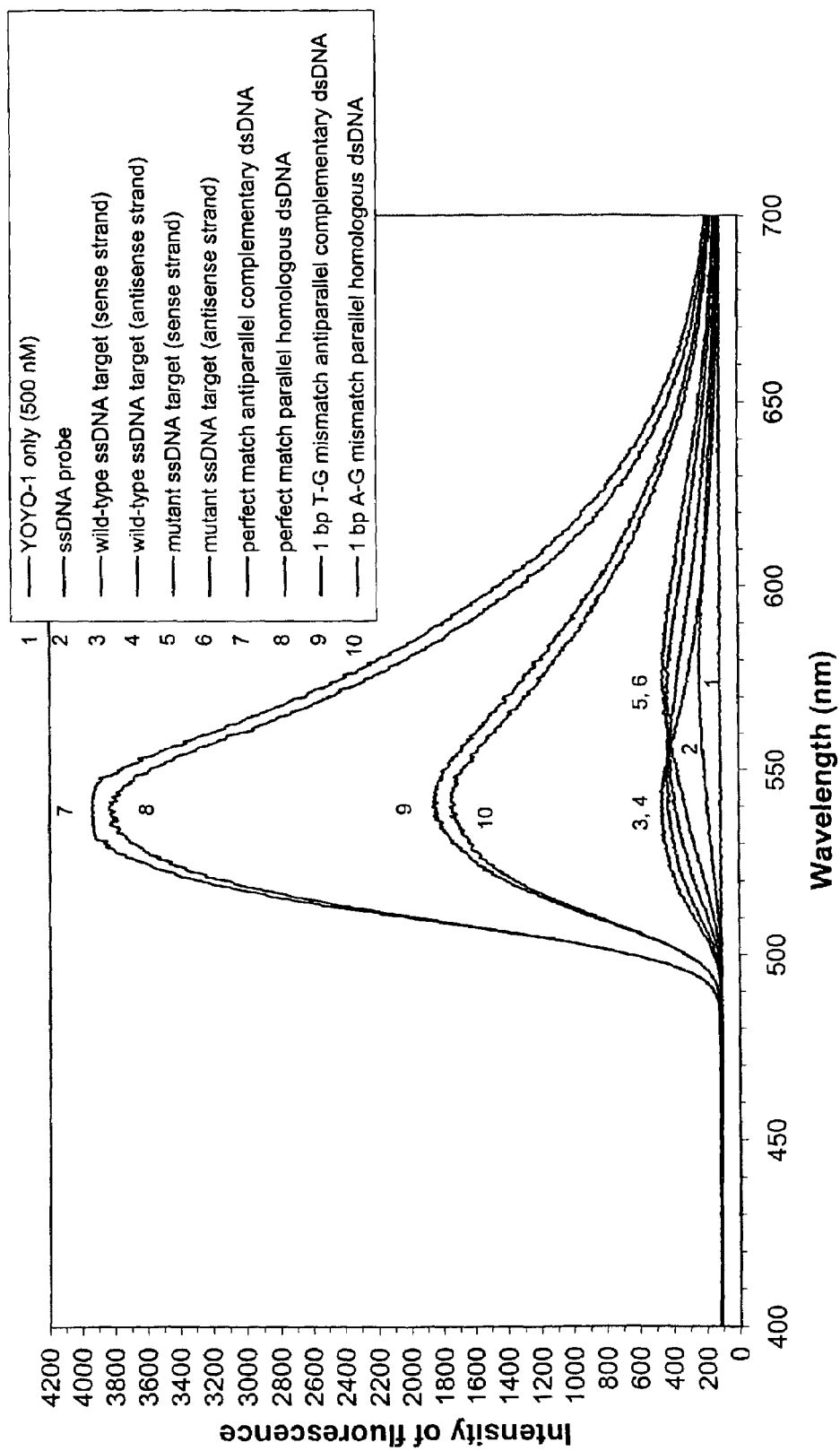

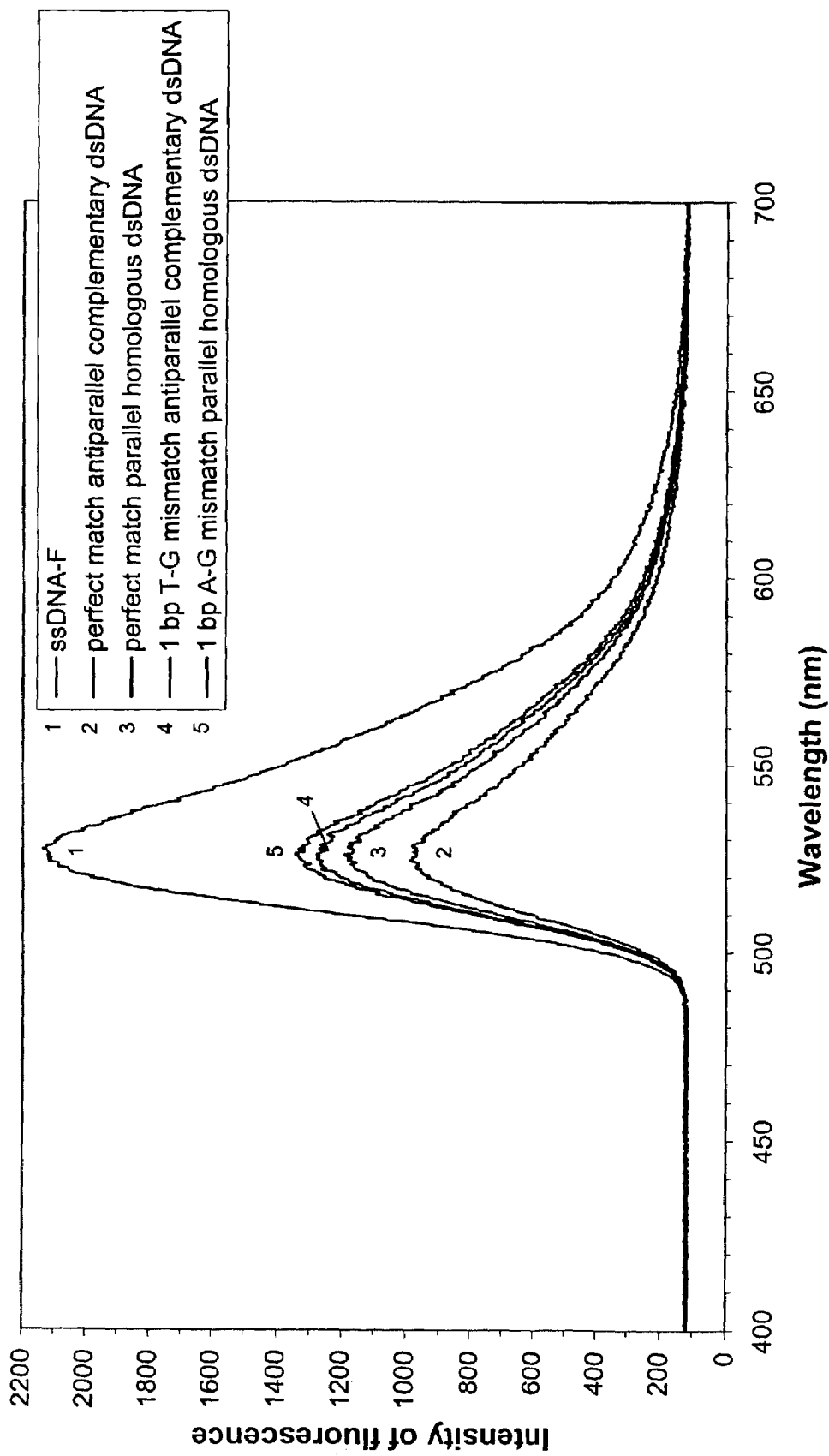
FIG. 1B. Binding of 15-mer ssDNA-F probe (2 pmole) and 50-mer antiparallel or parallel ssDNA (2 pmole) (after 30 min)

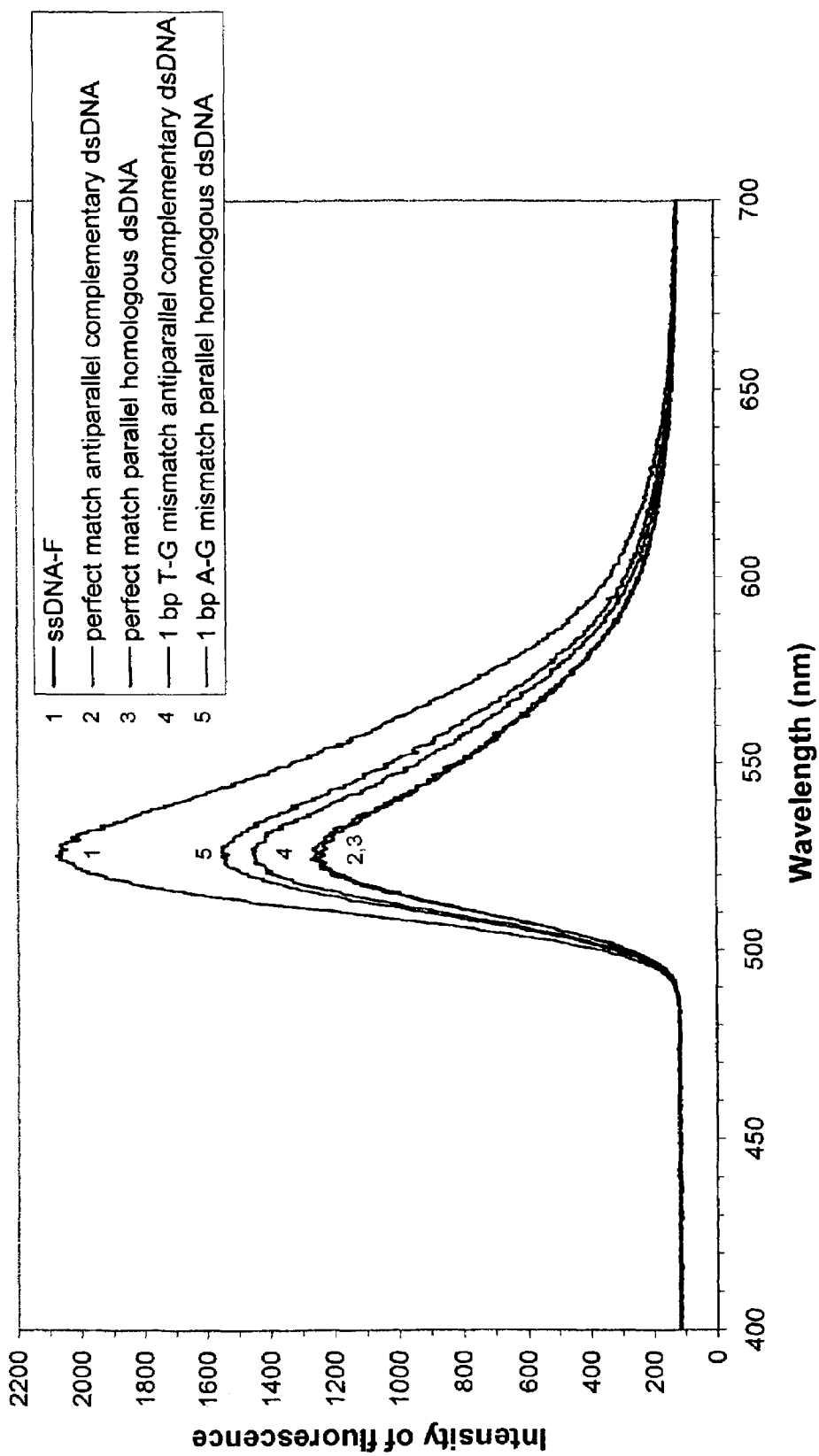
FIG.1C. Binding of 15-mer ssDNA-F probe (2 pmole) and 50-mer antiparallel or parallel ssDNA (2 pmole) (after 90 min)
1 ssDNA-F
2 perfect match antiparallel complementary dsDNA
3 perfect match parallel homologous dsDNA
4 1 bp T-G mismatch antiparallel complementary dsDNA
5 1 bp A-G mismatch parallel homologous dsDNA

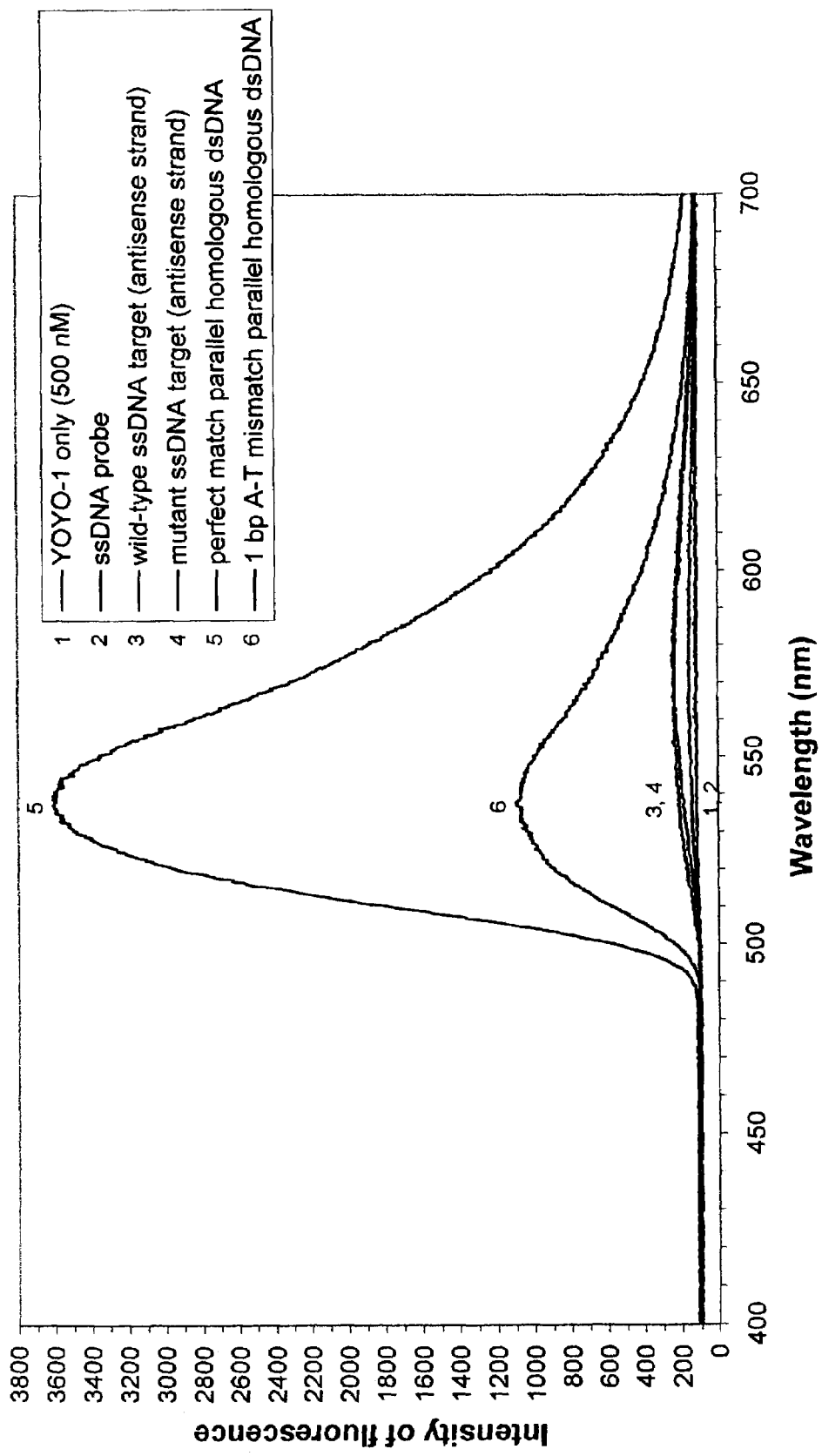
FIG. 2A. Binding of 15-mer ssDNA probe (2 pmole) and 50-mer parallel homologous ssDNA target (2 pmole) (53% GC) with YOYO-1

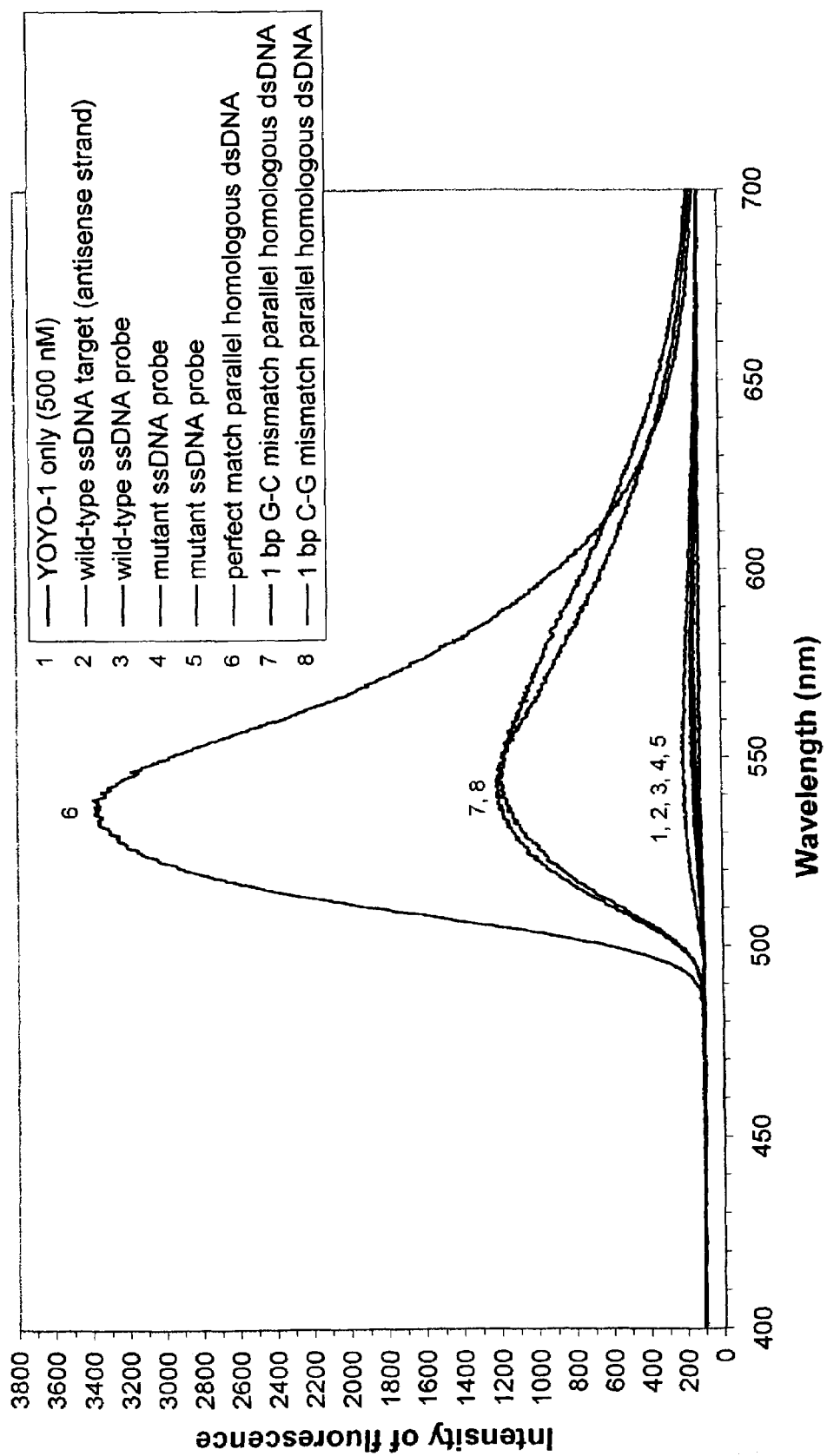
FIG. 2B. Binding of 15-mer ssDNA probe (2 pmole) and 50-mer parallel homologous ssDNA target (2 pmole) (33% GC) with YOYO-1

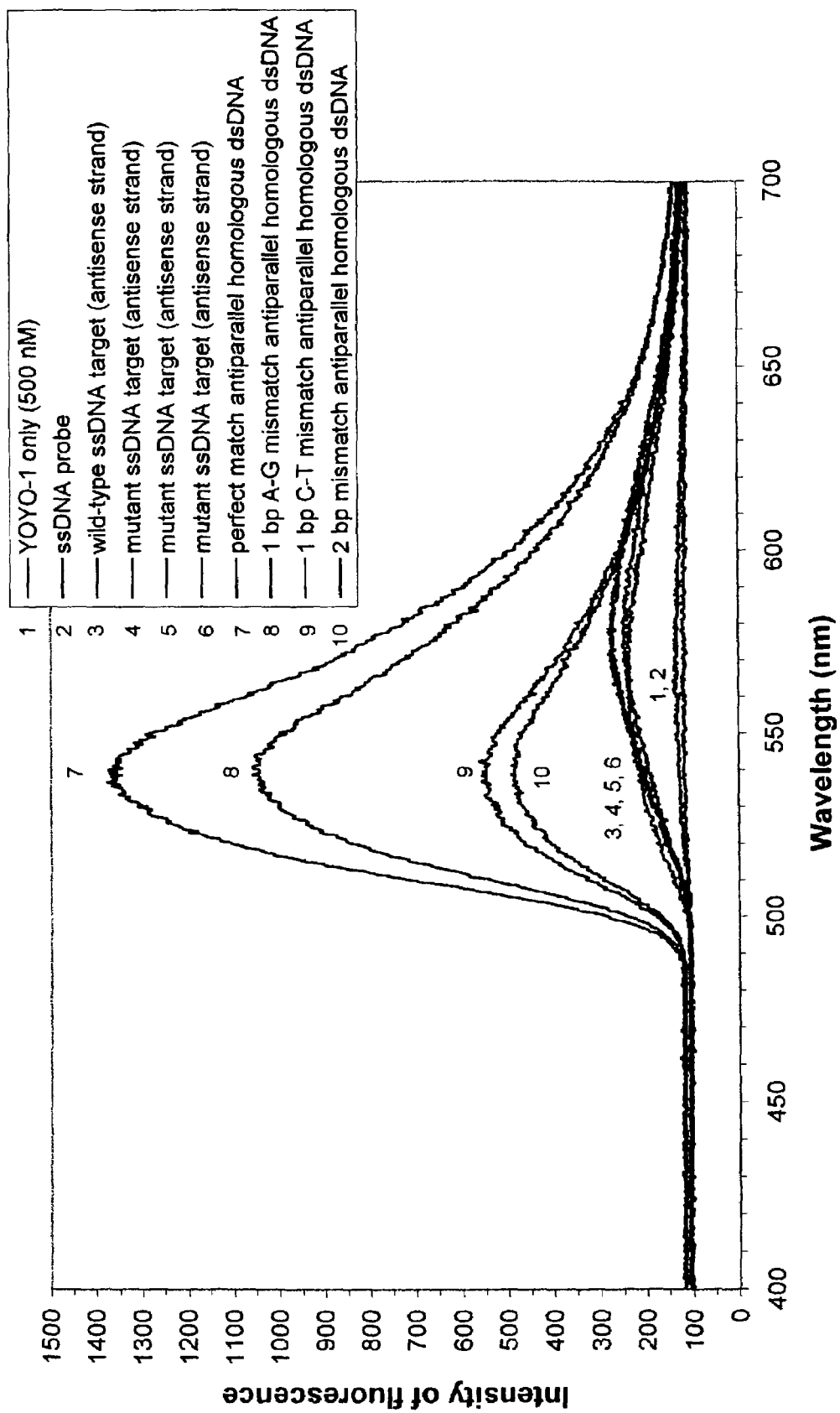
FIG. 3A. Binding of 15-mer ssDNA probe (2 pmole) and 50-mer antiparallel homologous ssDNA target (2 pmole) with YOYO-1

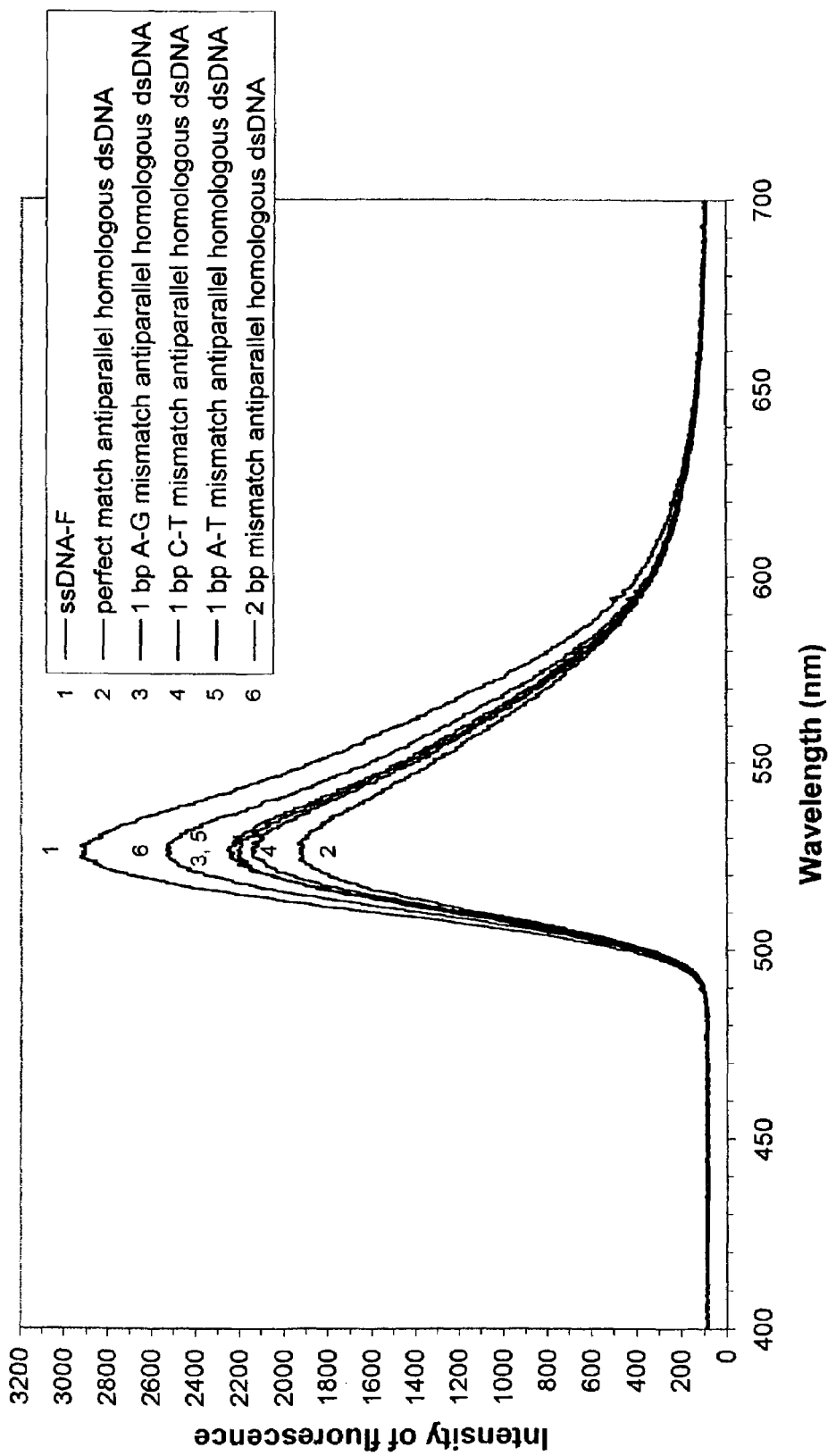
Fig. 3B. Binding of 15-mer ssDNA-F probe (2 pmole) and 50-mer antiparallel homologous ssDNA (2 pmole) in the presence of 50 mM NaCl (after 15 min)

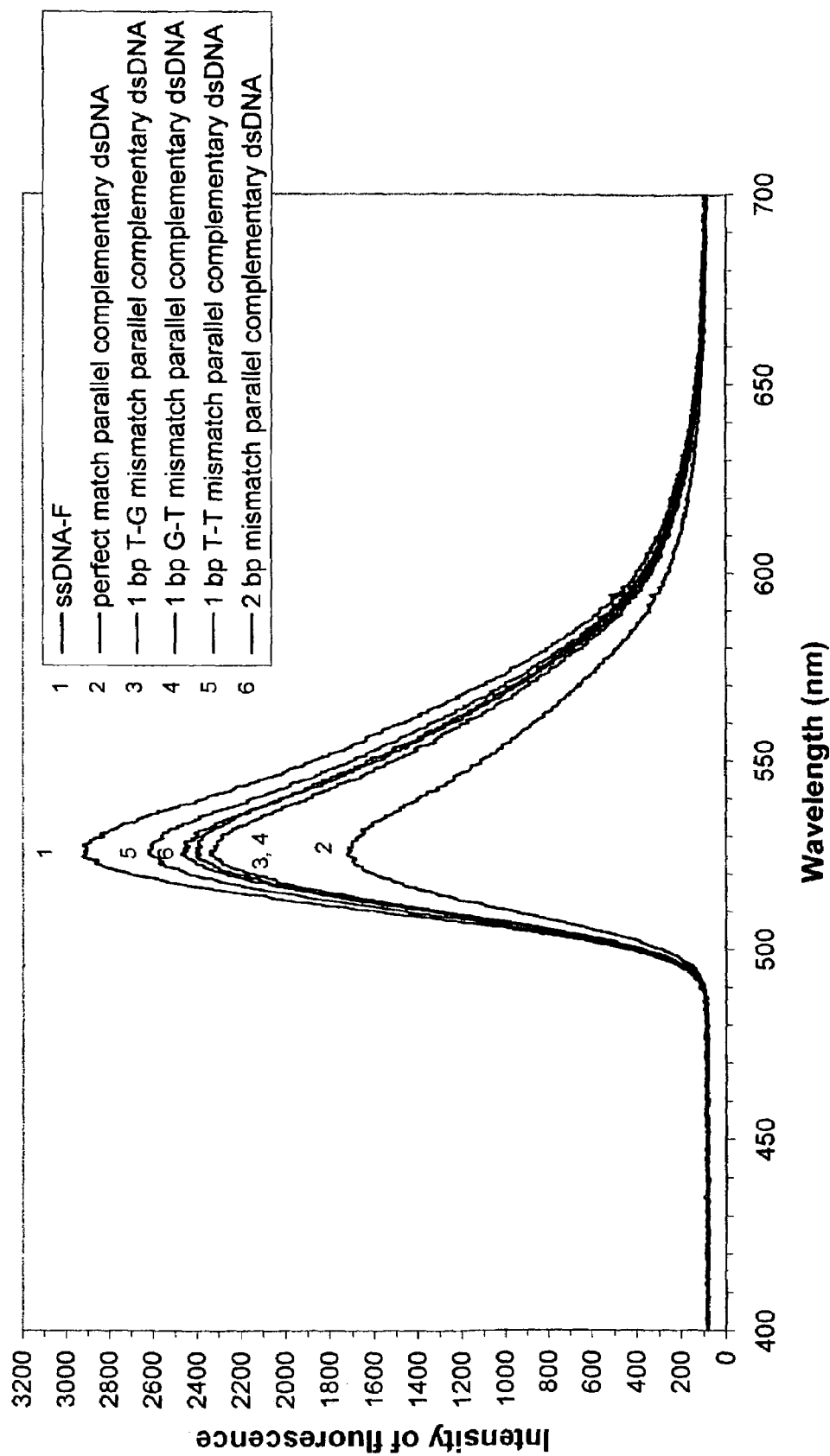
FIG. 4. Binding of 15-mer ssDNA-F probe (2 pmole) and 50-mer parallel complementary ssDNA (2 pmole) in the presence of 50 mM NaCl (after 15 min)

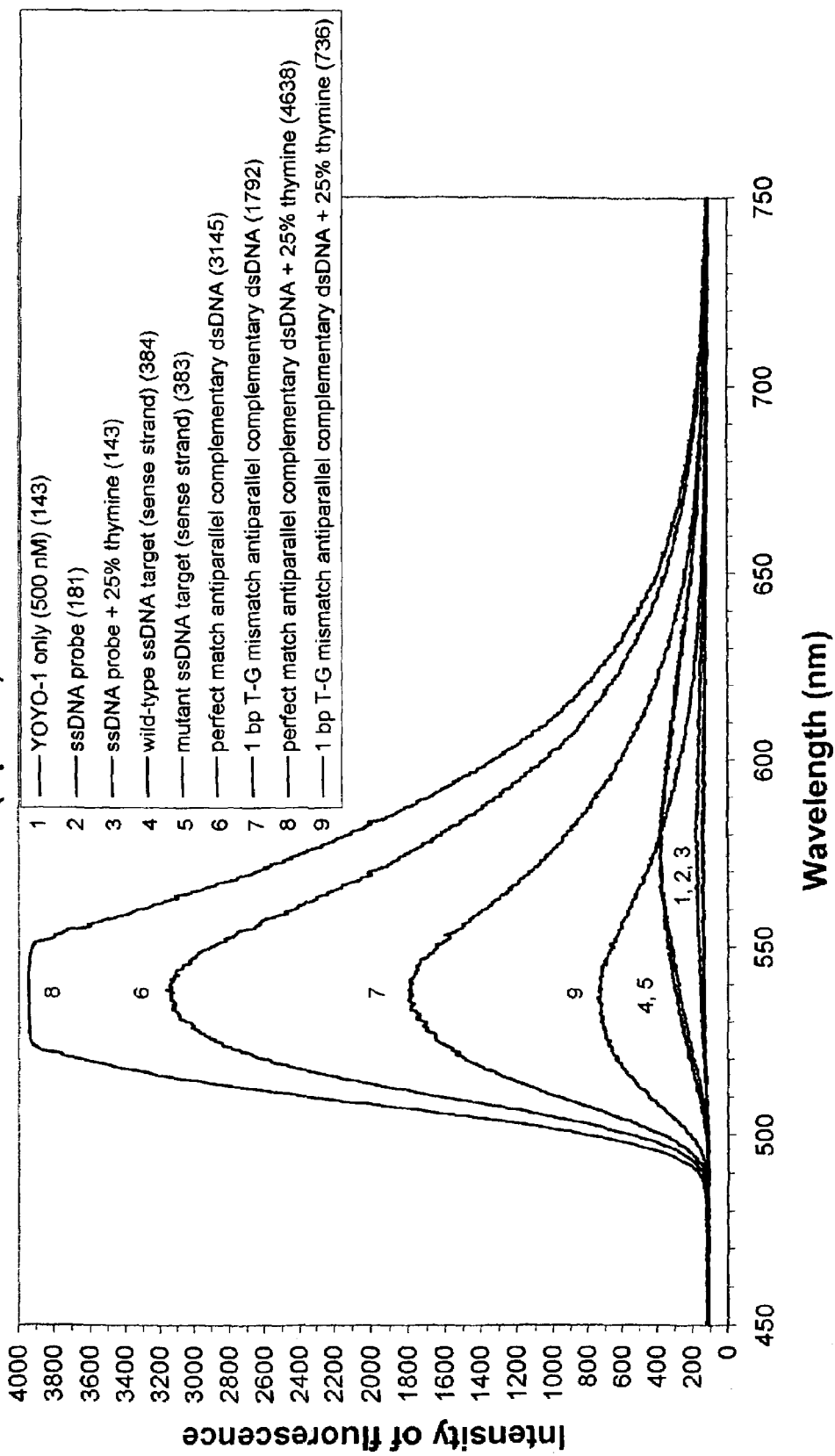
FIG. 5A. Binding of 15-mer ssDNA probe (2 pmole) and 50-mer antiparallel complementary ssDNA target (2 pmole) in the presence of YOYO-1 and thymine (3 pmole)

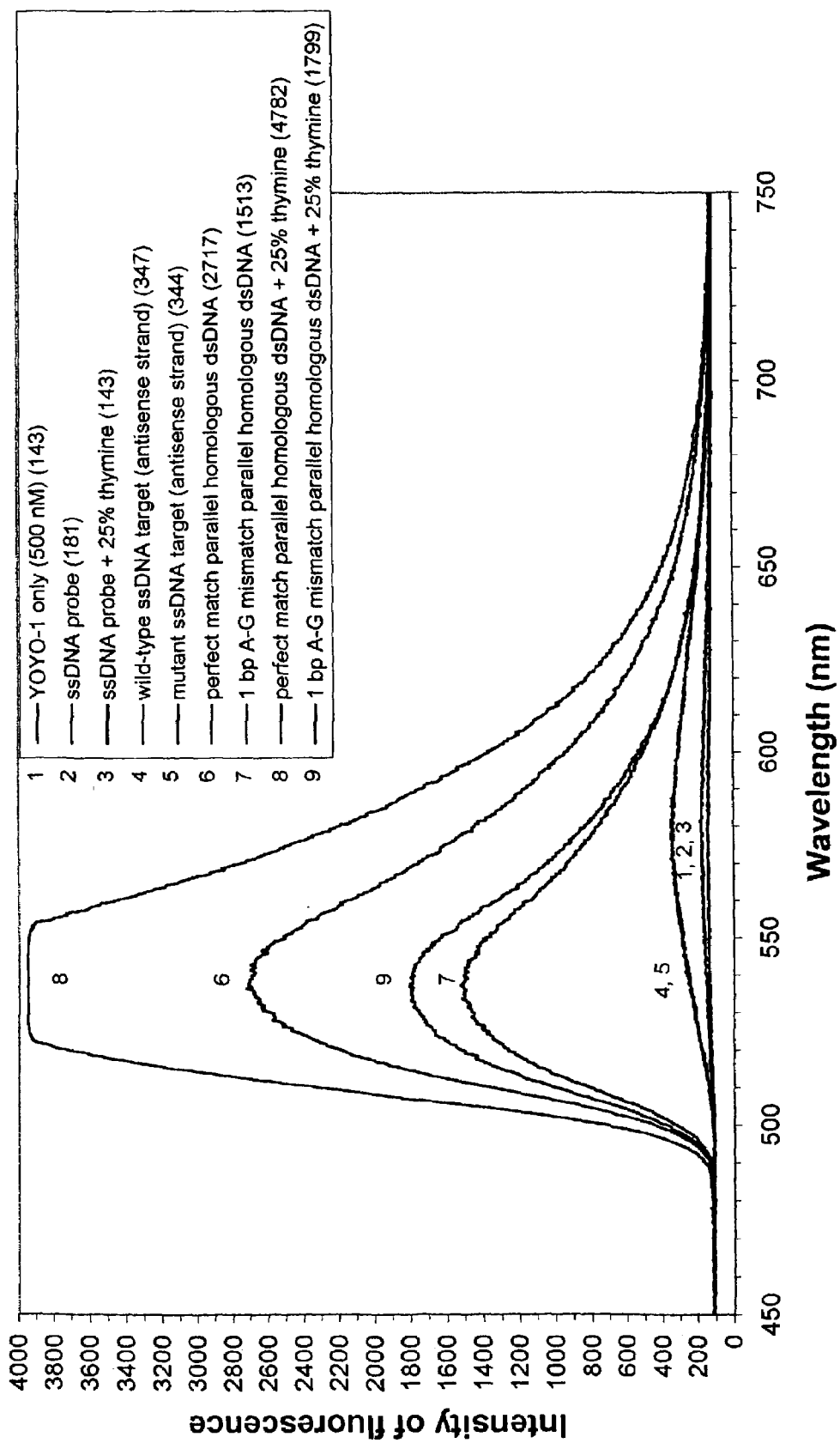
FIG. 5B. Binding of 15-mer ssDNA probe (2 pmole) and 50-mer parallel homologous ssDNA target (2 pmole) in the presence of YOYO-1 and thymine (3 pmole)

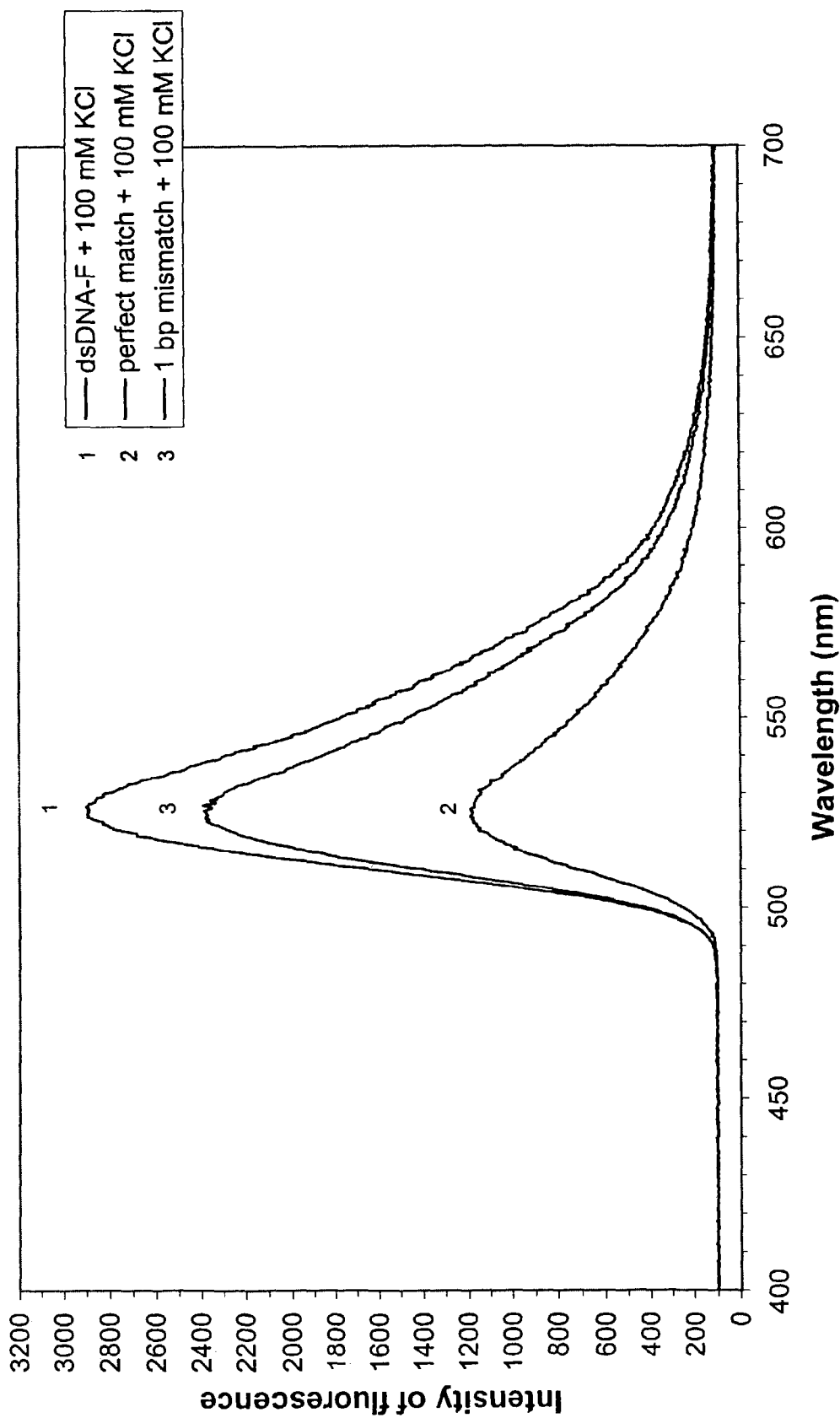
FIG. 6. Mix of 15-mer dsDNA-F (4 pmole) (53% GC) and 50-mer dsDNA (0.4 pmole) in the presence of 100 mM KCl (after 1 hr)
1 — dsDNA-F + 100 mM KCl
2 — perfect match + 100 mM KCl
3 — 1 bp mismatch + 100 mM KCl

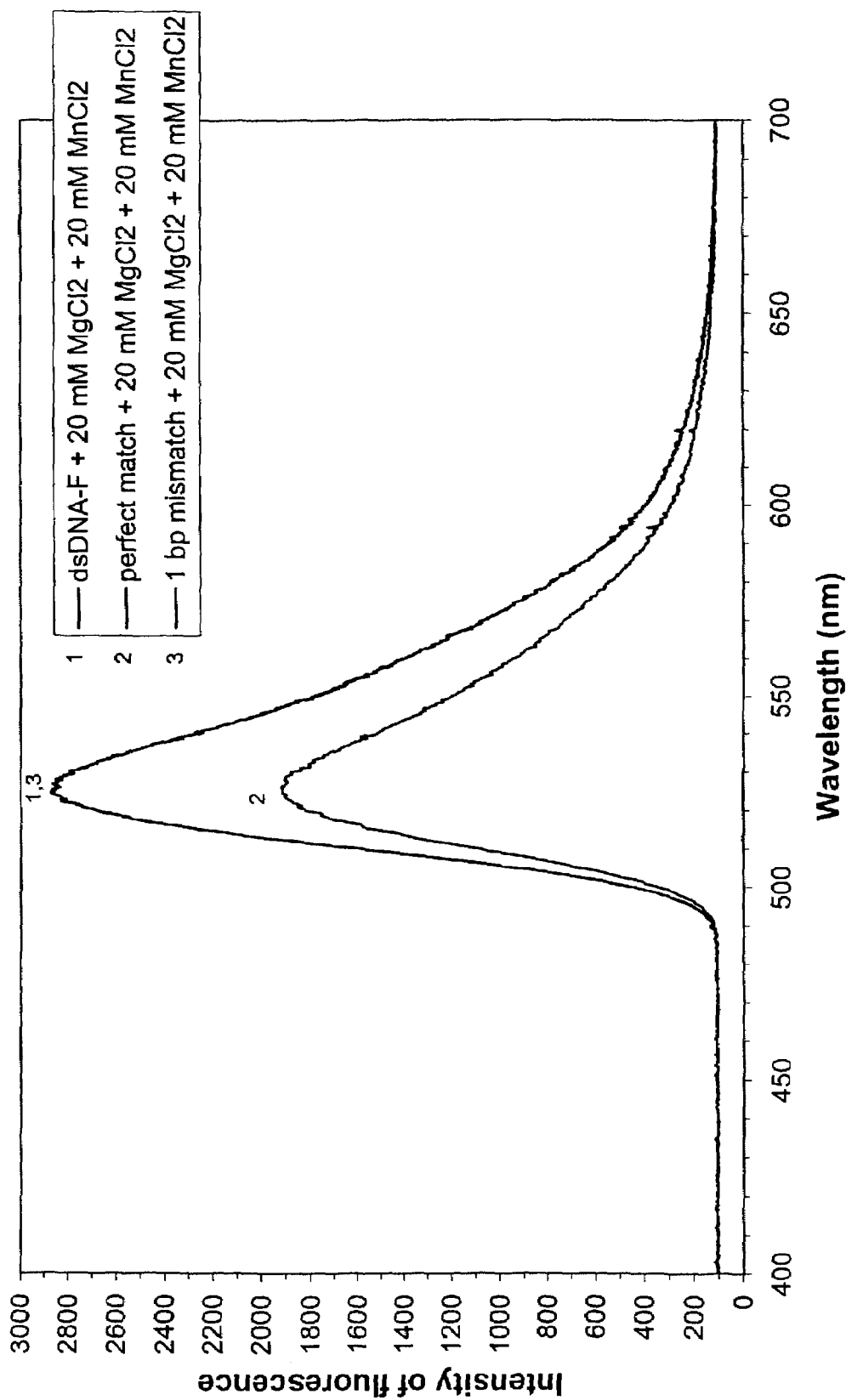
FIG. 7. Mix of 15-mer dsDNA-F (4 pmole) (53% GC) and 50-mer dsDNA (0.4 pmole) in the presence of divalent cations (after 1 hr)

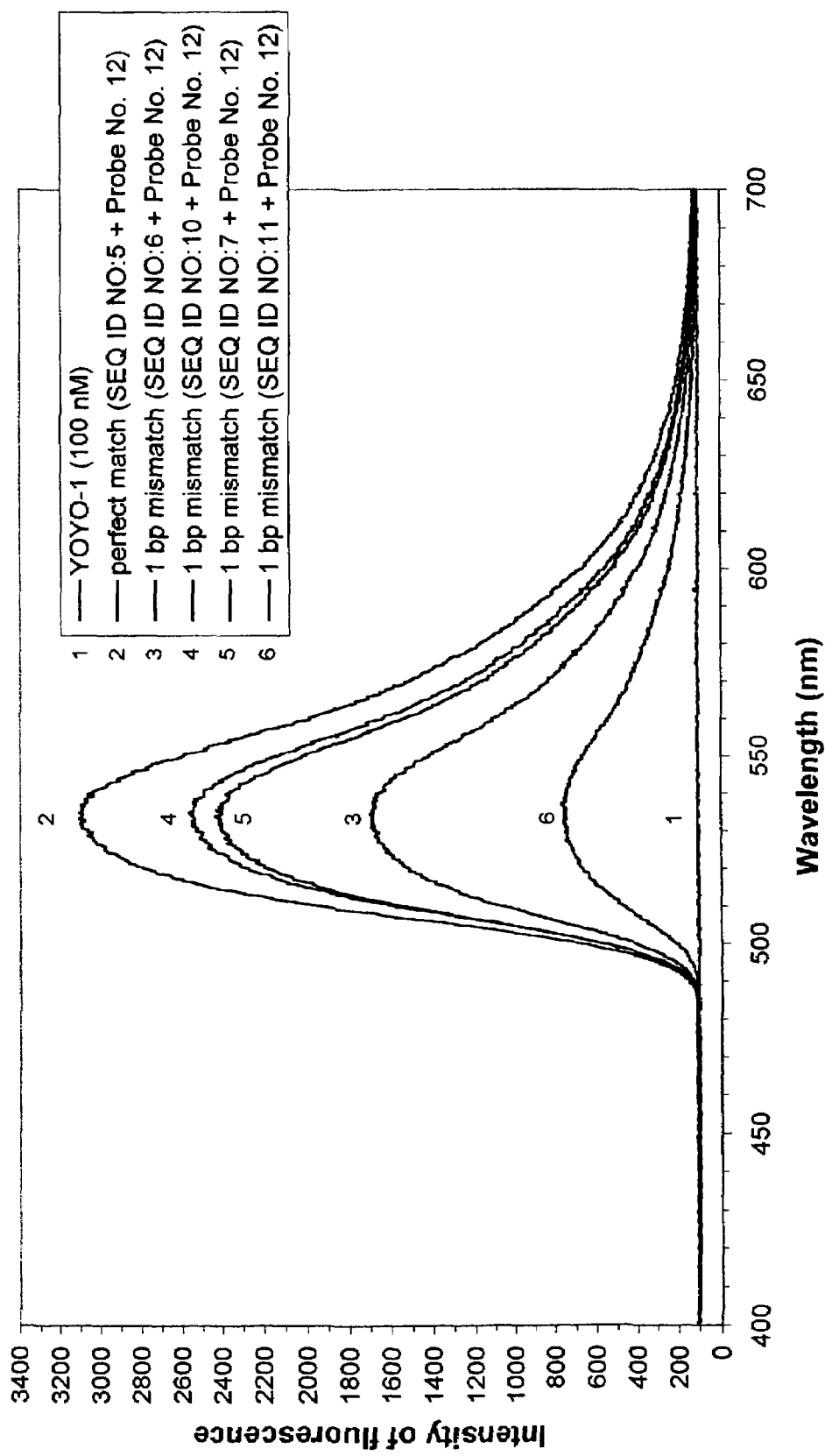
FIG. 8. Mix of 15-mer dsDNA (4 pmole) (53% GC) and 50-mer dsDNA (0.4 pmole) in the presence of 100 nM YOYO-1

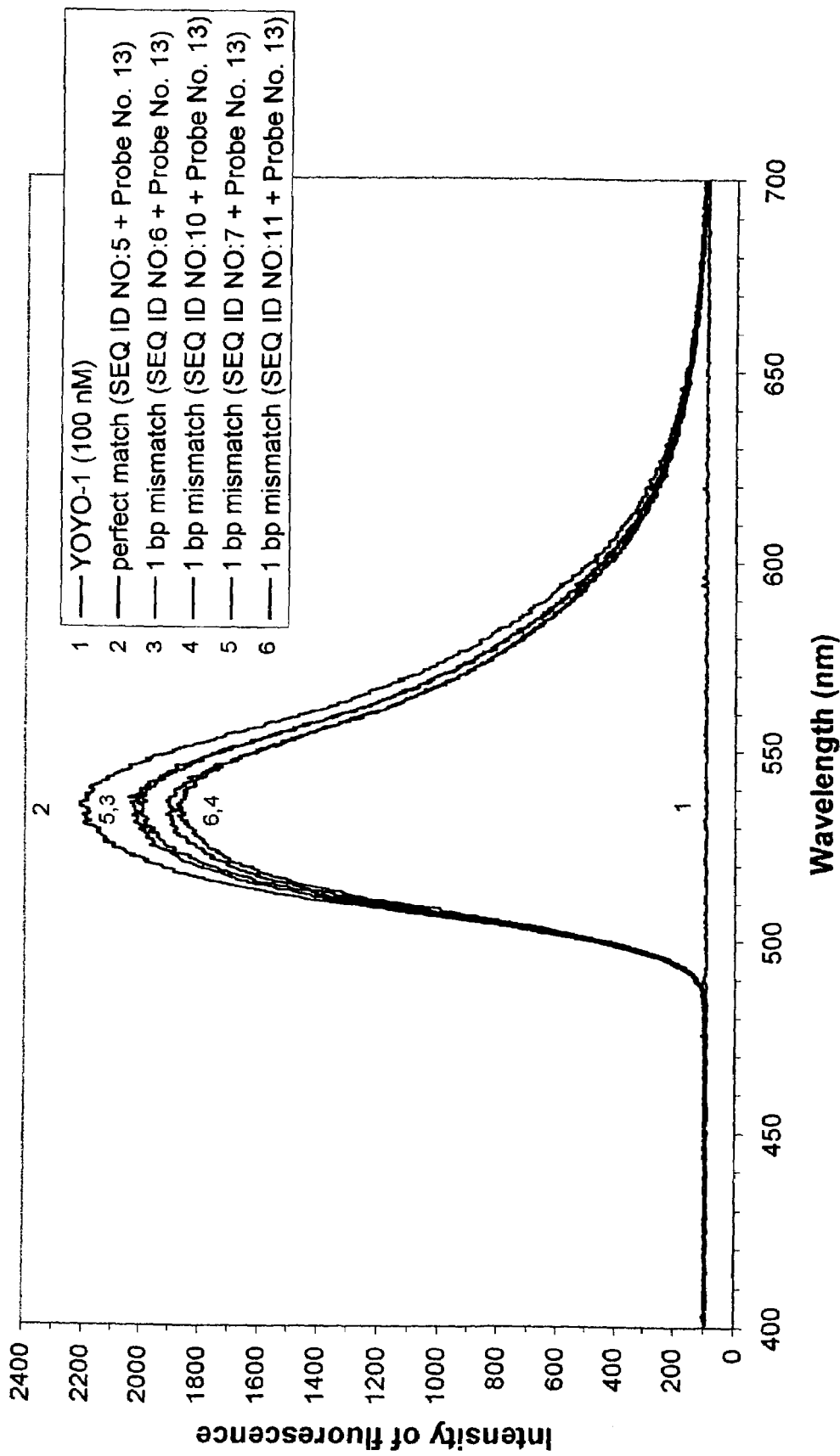

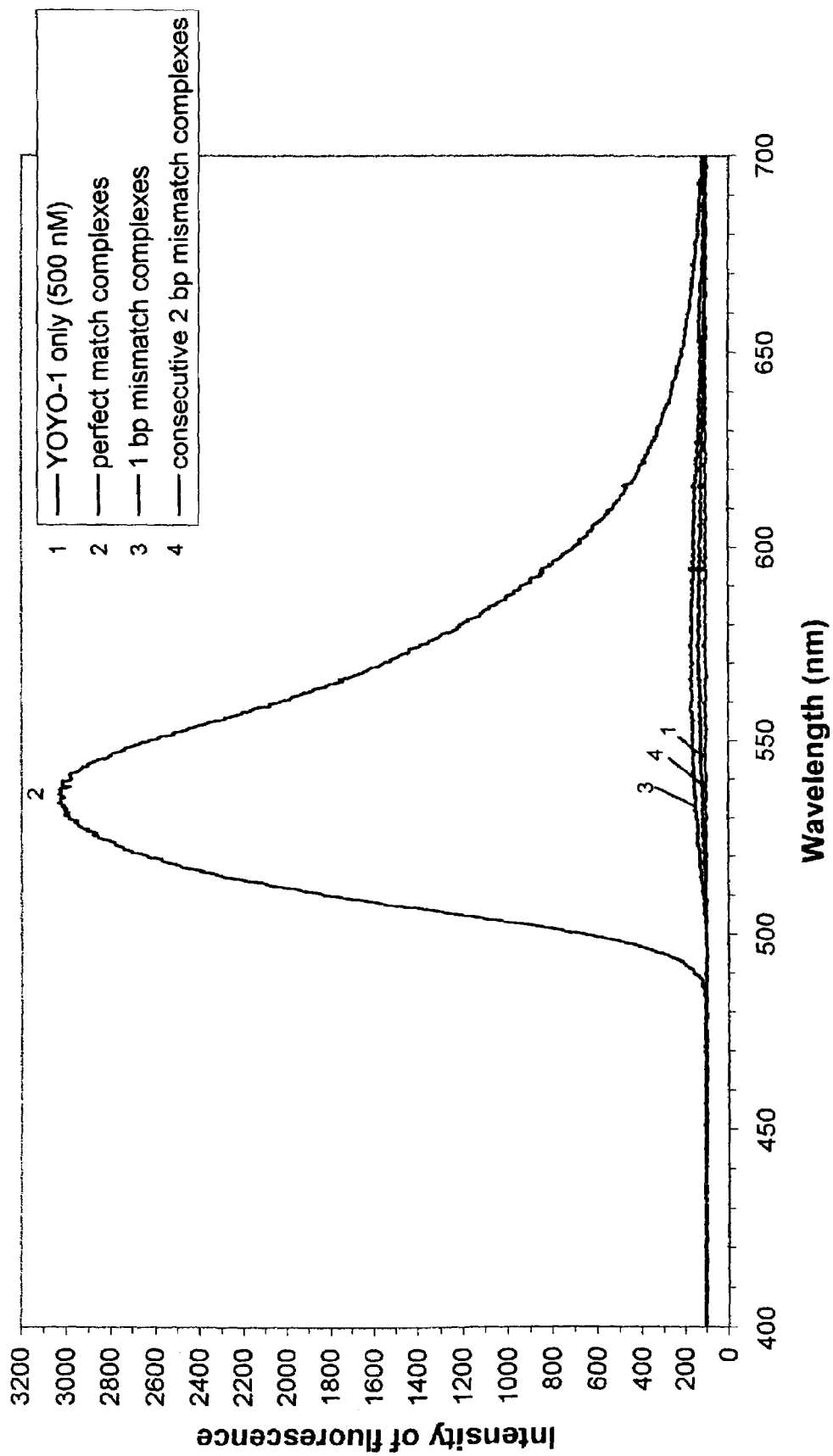

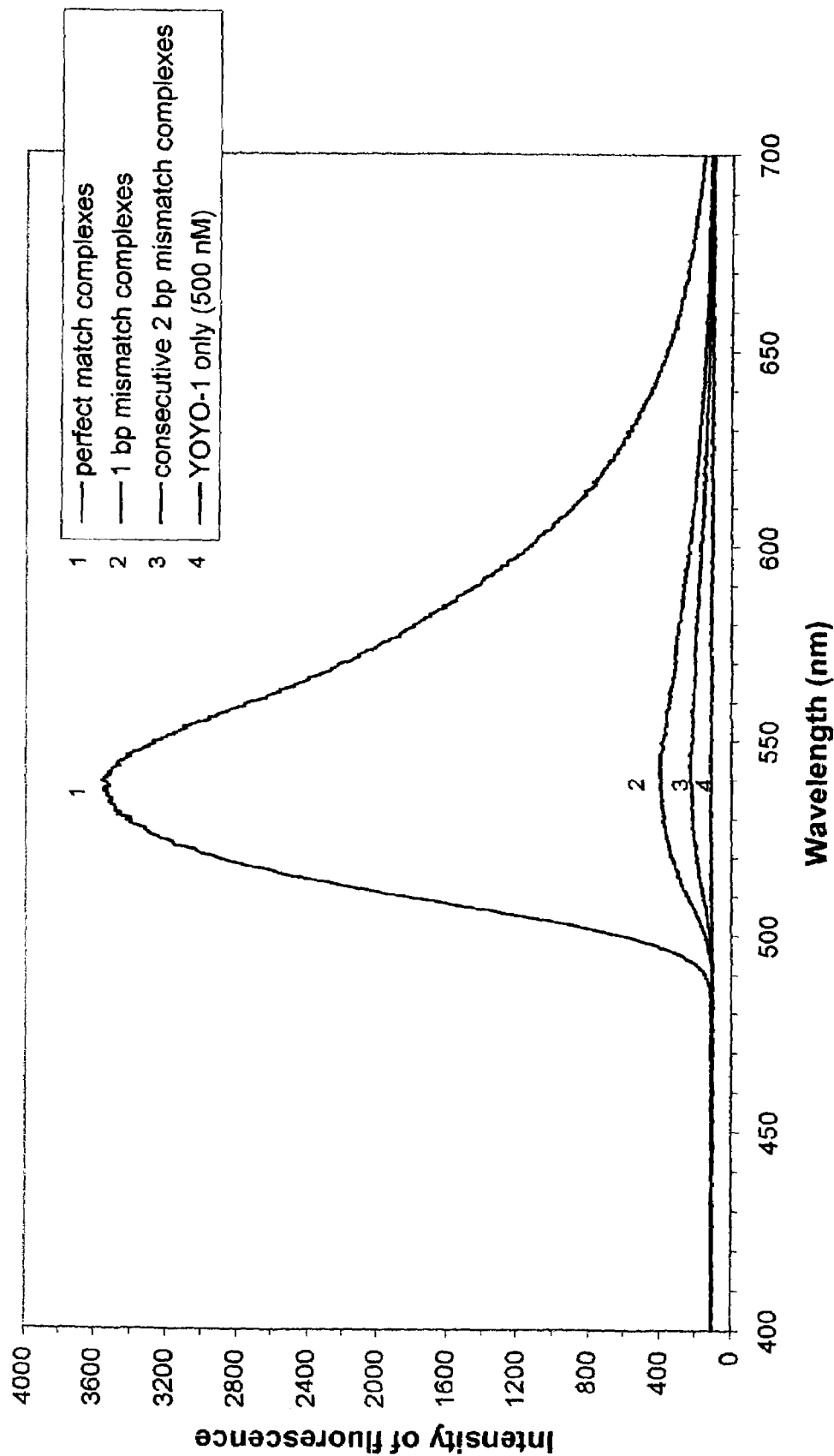
FIG. 10B. Binding of 15-mer parallel PNA to 50-mer non-denatured dsDNA with YOYO-1

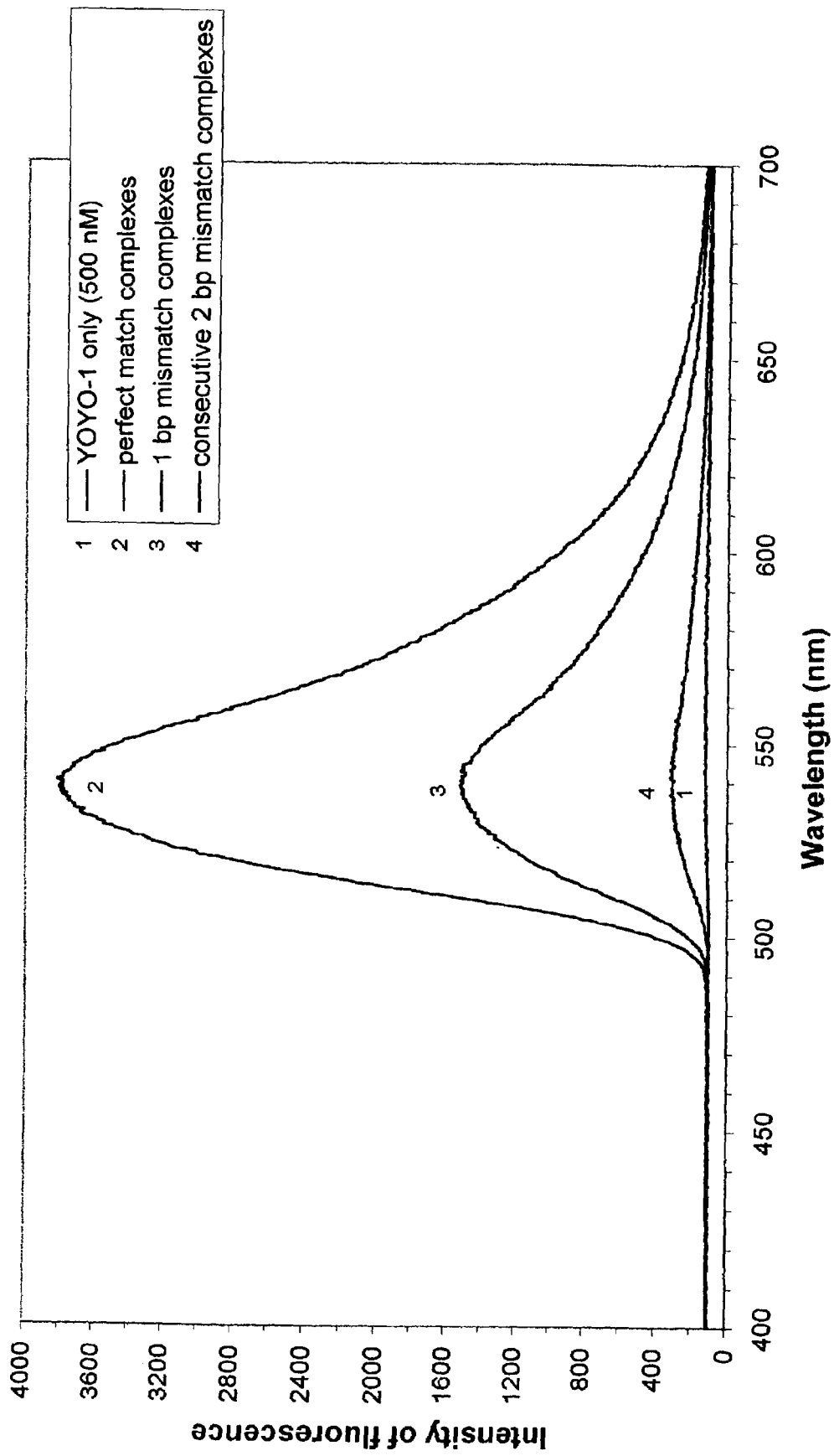
FIG. 11A. Binding of 15-mer antiparallel ssDNA to 50-mer non-denatured dsDNA with YOYO-1

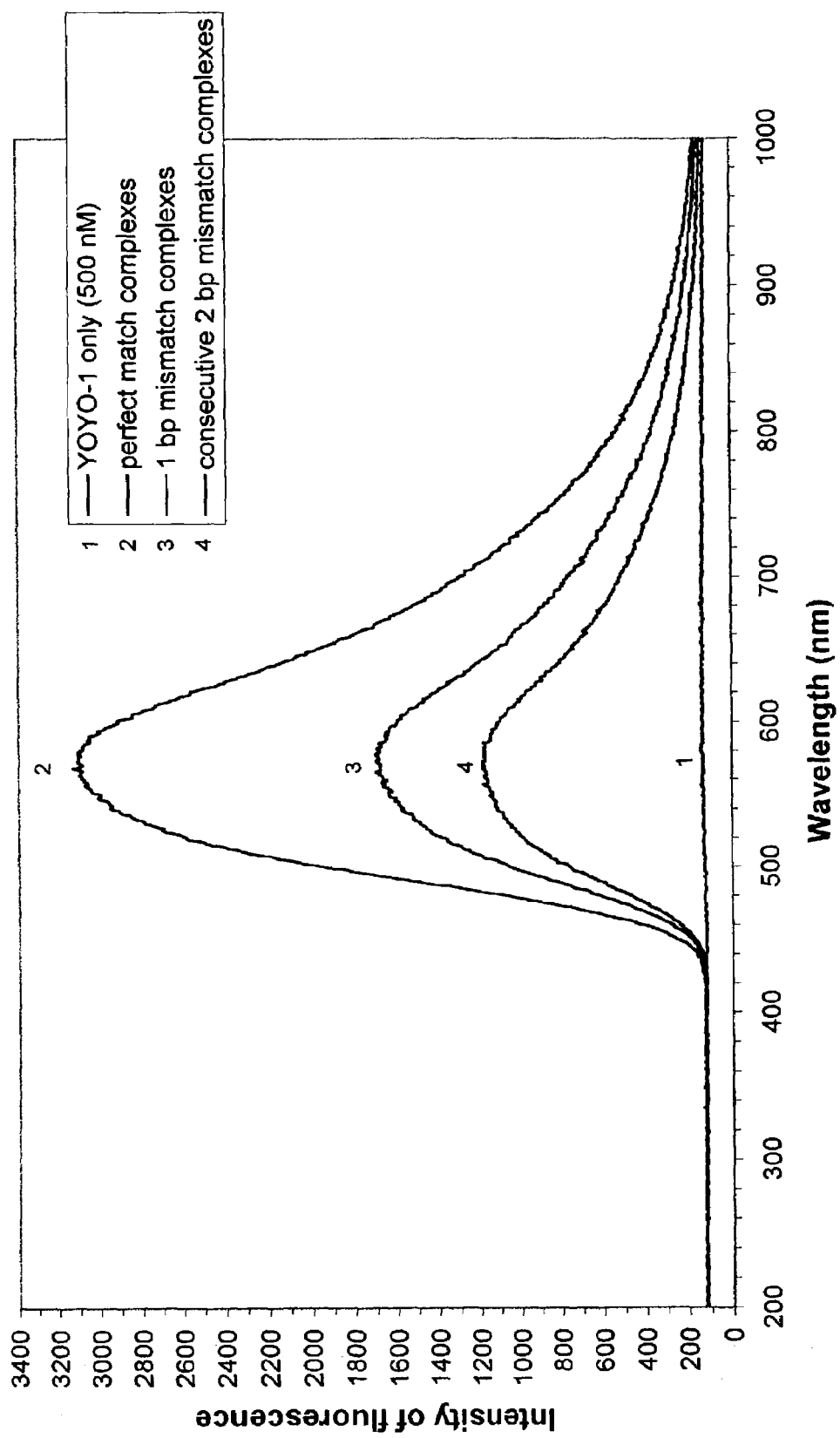
FIG. 11B. Binding of 15-mer parallel ssDNA to 50-mer non-denatured dsDNA with YOYO-1

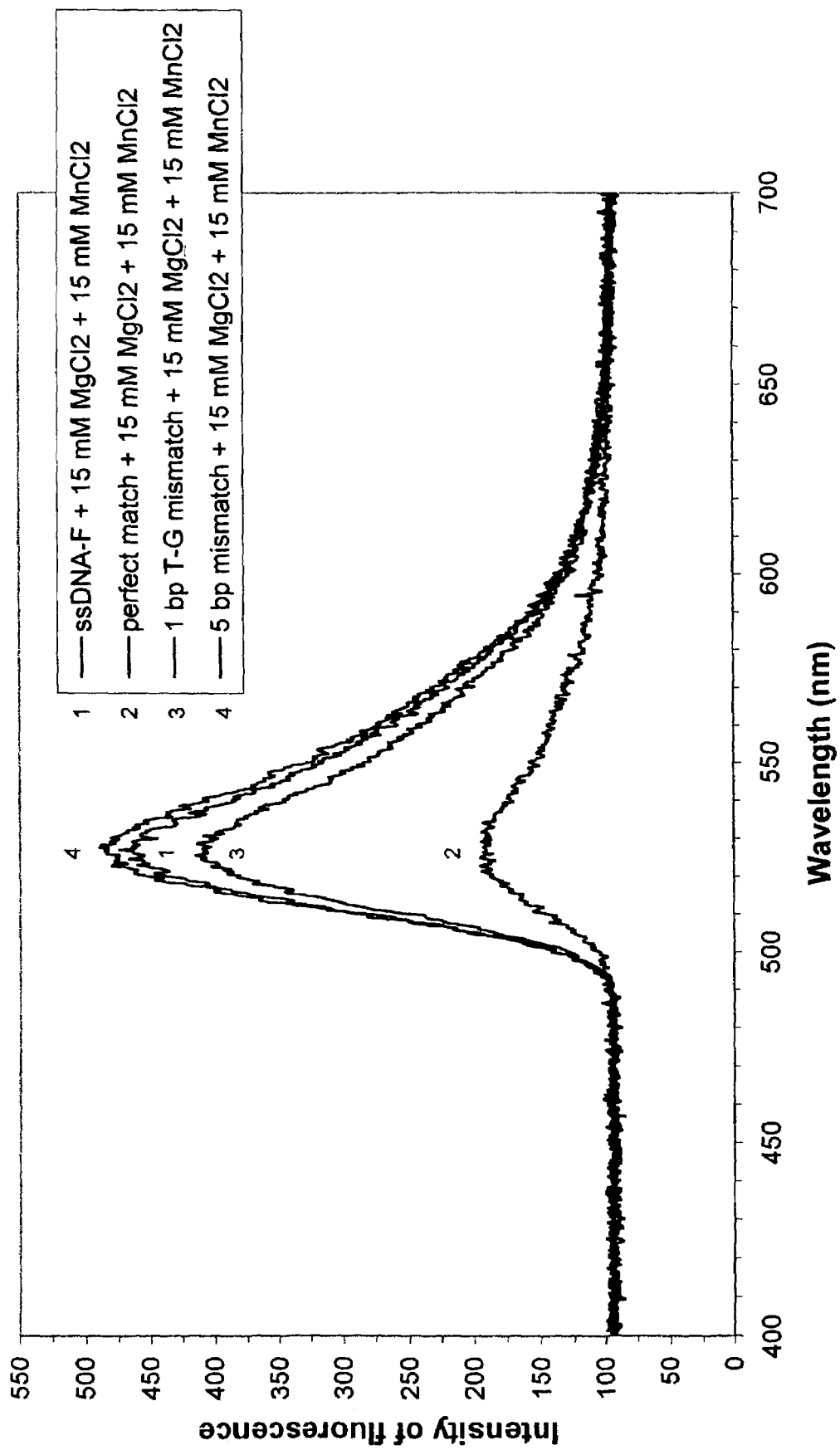
FIG. 12A. Binding of 15-mer antiparallel ssDNA-F probe (4 pmole) and 50-mer dsDNA (0.4 pmole) in the presence of divalent cations (after 1 hr)

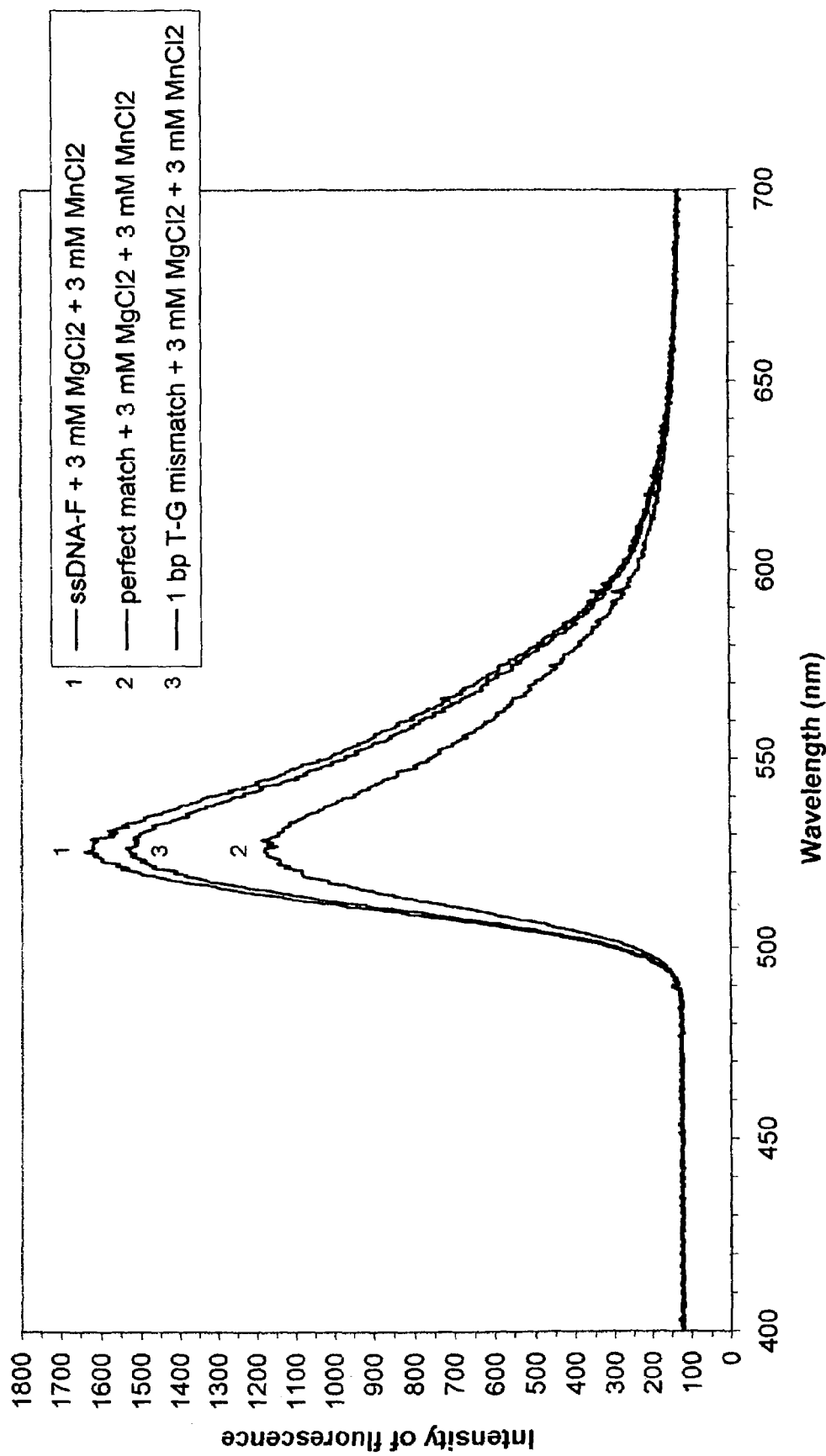
FIG. 12B. Binding of 15-mer parallel ssDNA-F probe (4 pmole) and 50-mer dsDNA (0.4 pmole) in the presence of divalent cations (after 45 min)

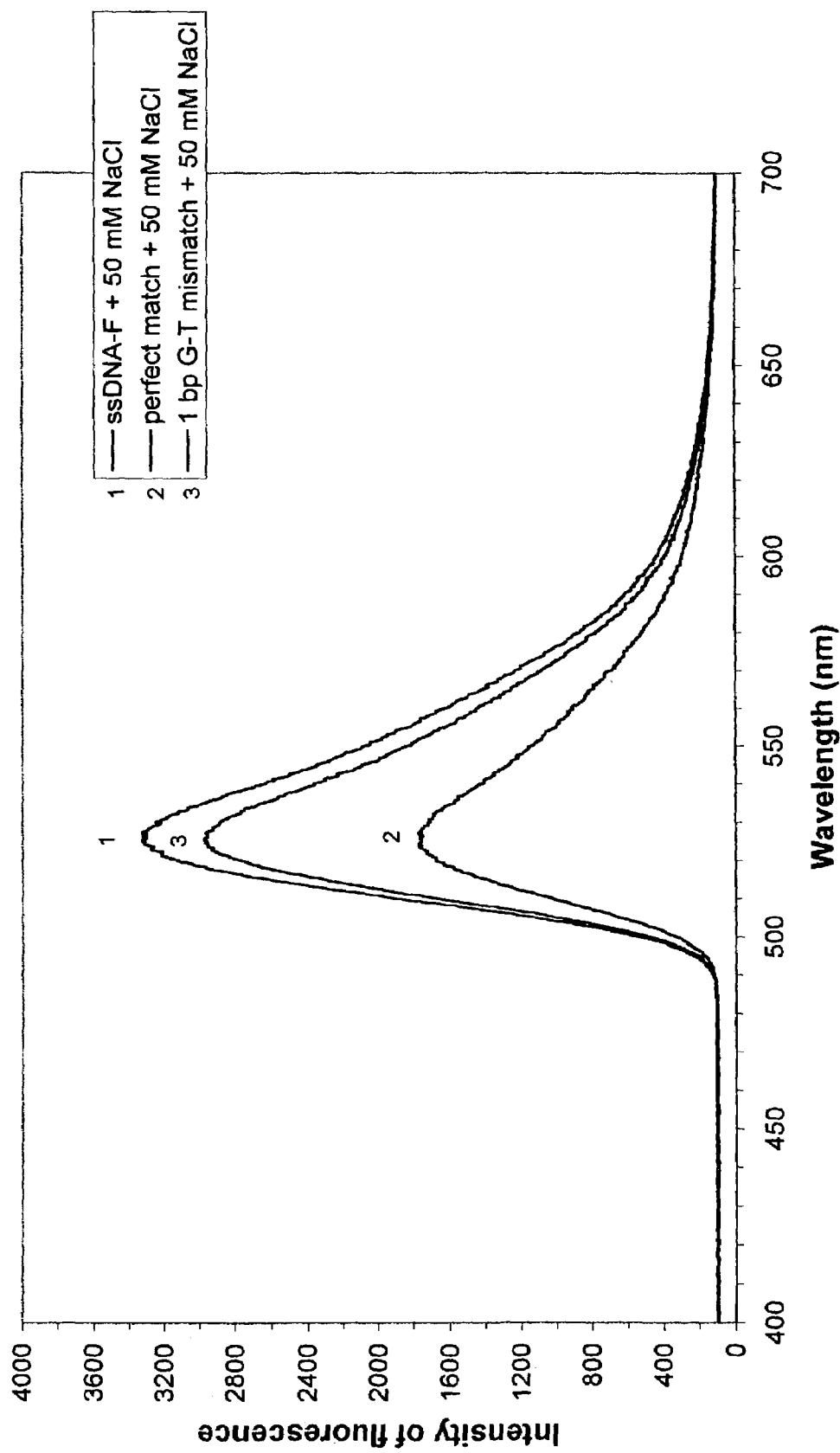
FIG. 13A. Binding of 15-mer antiparallel ssDNA-F probe (4 pmole) and 50-mer dsDNA (0.4 pmole) in the presence of 50 mM NaCl (after 1 hr)

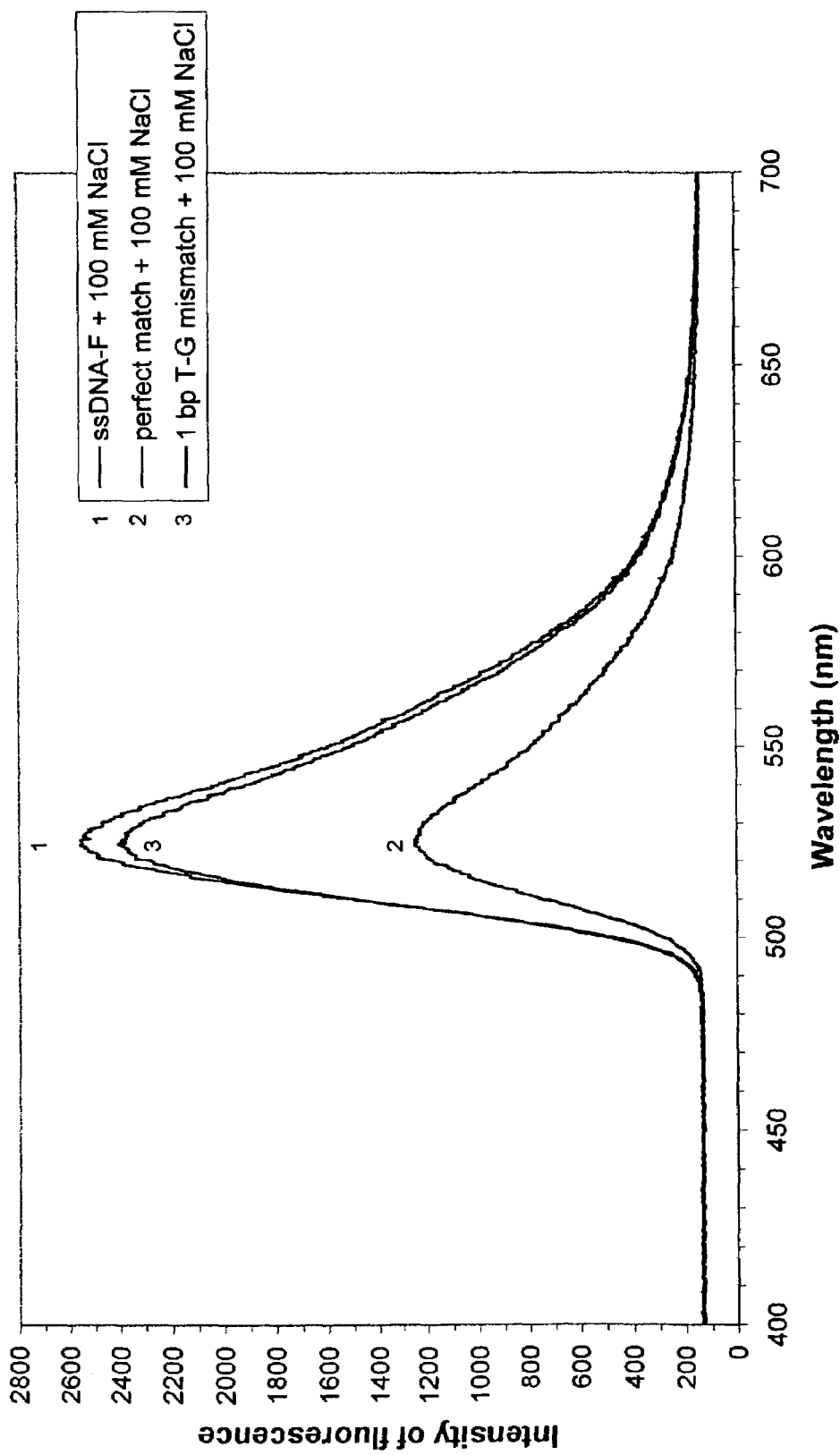
FIG. 13B. Binding of 15-mer parallel ssDNA-F probe (4 pmol) and 50-mer dsDNA (0.4 pmol) in the presence of 100 mM NaCl (after 75min)

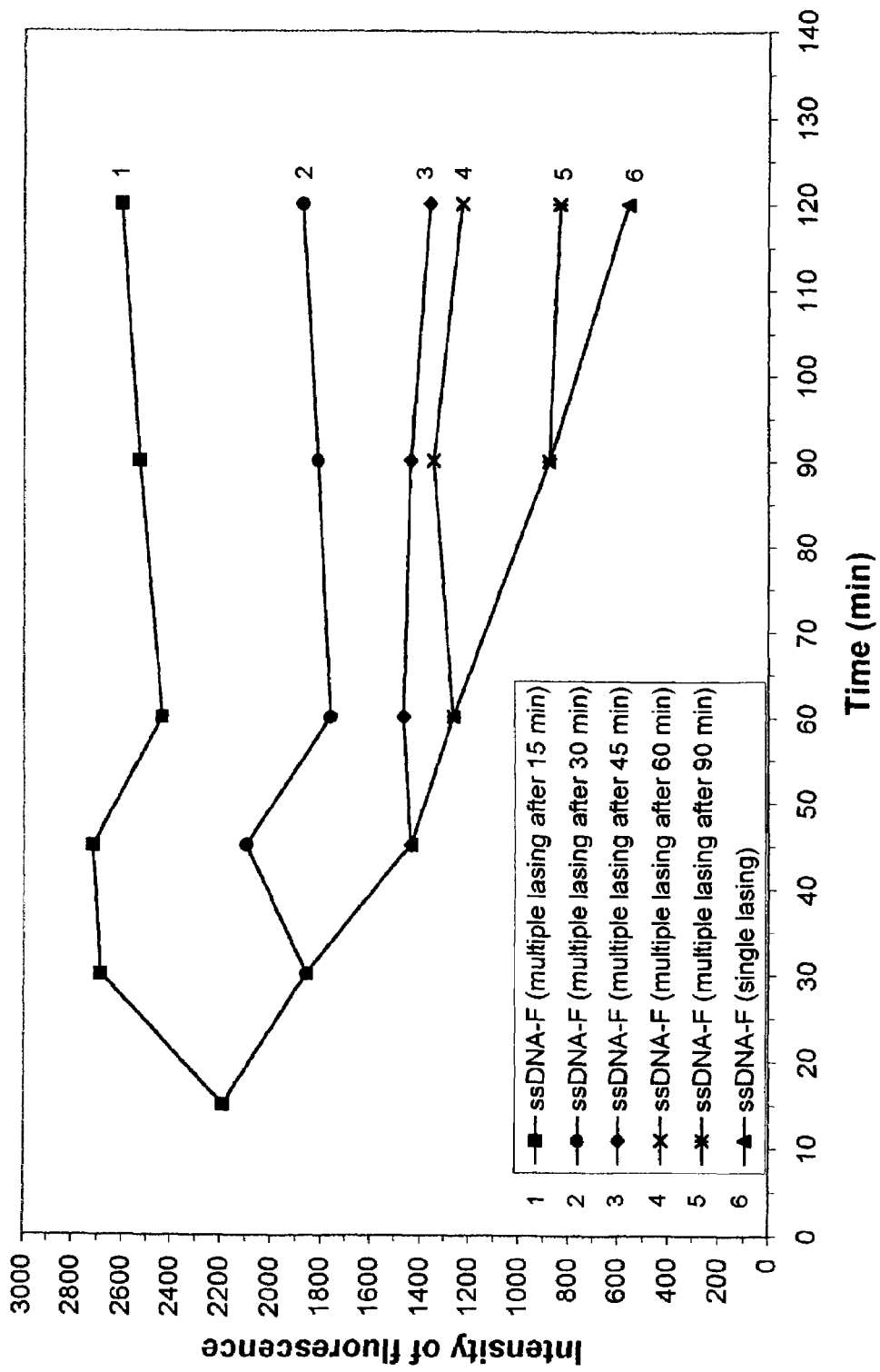
FIG. 14A. Effect of multiple laser treatment on cationic quench of 15-mer antiparallel ssDNA-F (4 pmole) by 10 mM $MgCl_2$ + 10 mM $MnCl_2$

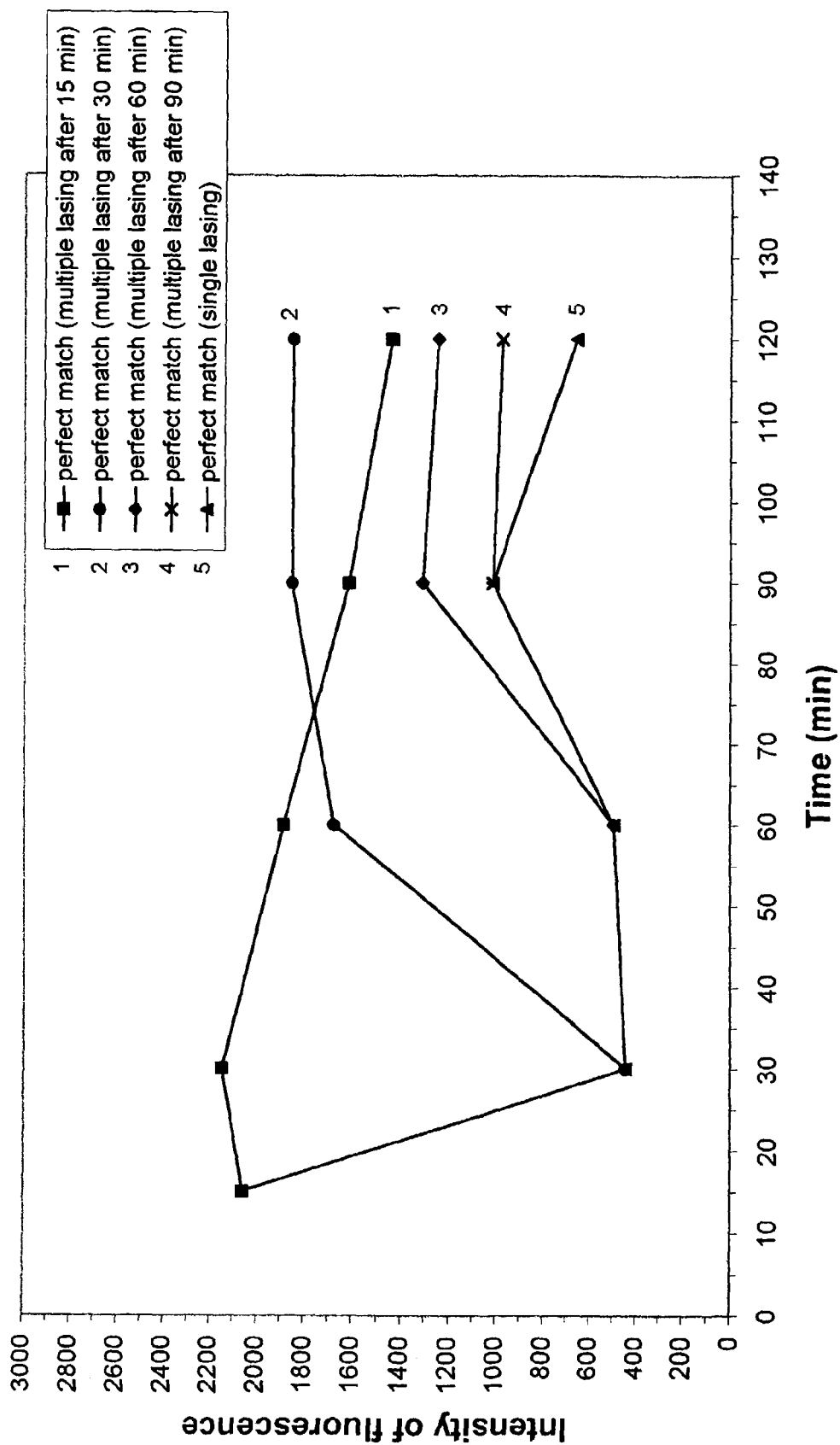
FIG. 14B. Effect of multiple laser treatment on complex formation between perfectly matched antiparallel 15-mer ssDNA-F (4 pmole) + 50-mer dsDNA (0.4 pmole) in the presence of 10 mM $MgCl_2$ + 10 mM $MnCl_2$

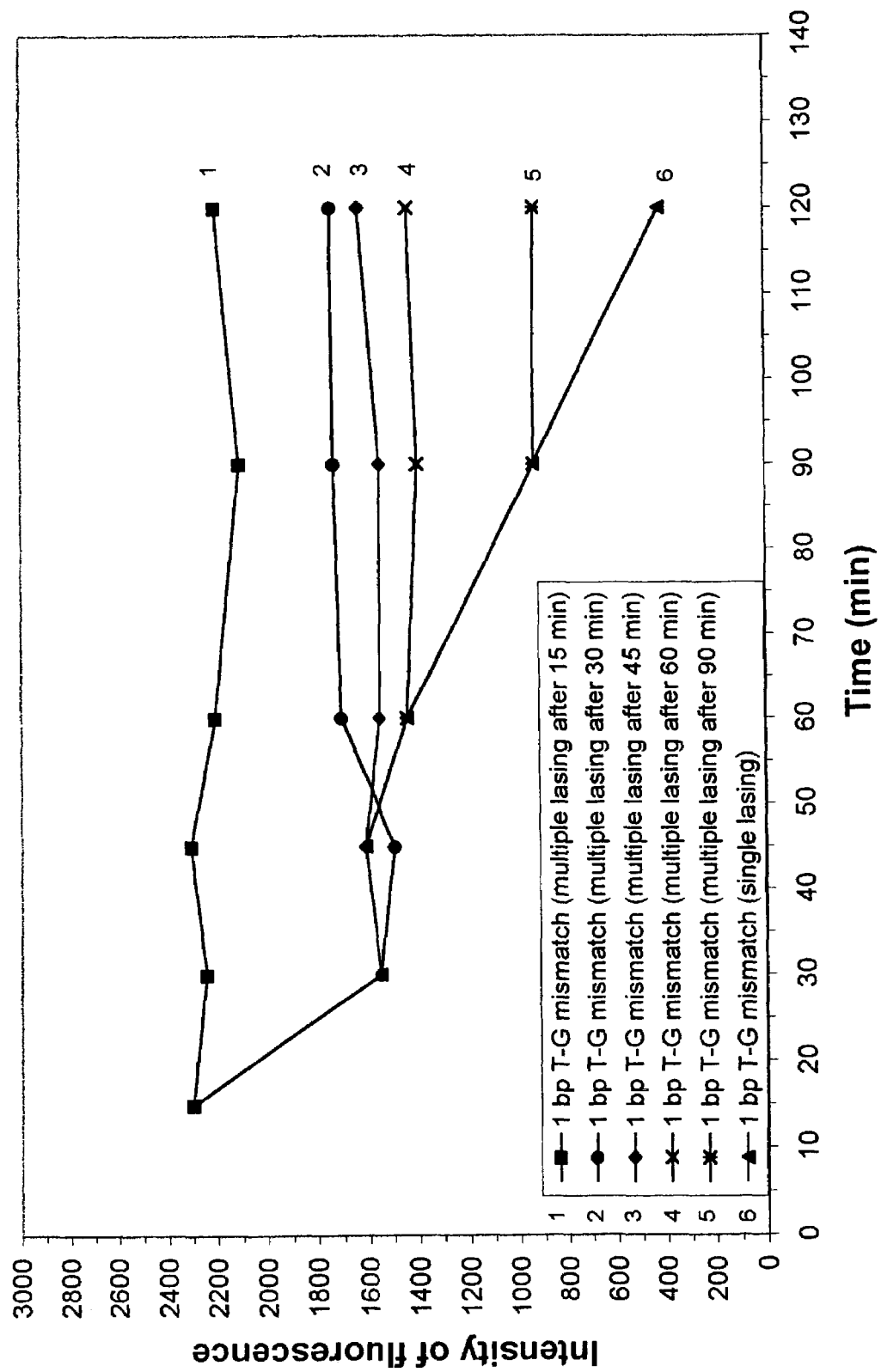

FIG. 14C. Effect of multiple laser treatment on complex formation between antiparallel 15-mer ssDNA-F (4 pmole) + 50-mer dsDNA (0.4 pmole) resulting in a 1 bp T-G mismatch in the presence of 10 mM MgCl$_2$ + 10 mM MnCl$_2$ 1 — 1 bp T-G mismatch (multiple lasing after 15 min)
2 — 1 bp T-G mismatch (multiple lasing after 30 min)
3 — 1 bp T-G mismatch (multiple lasing after 45 min)
4 — 1 bp T-G mismatch (multiple lasing after 60 min)
5 — 1 bp T-G mismatch (multiple lasing after 90 min)
6 — 1 bp T-G mismatch (single lasing)

PARALLEL OR ANTIPARALLEL, HOMOLOGOUS OR COMPLEMENTARY BINDING OF NUCLEIC ACIDS OR ANALOGUES THEREOF TO FORM DUPLEX, TRIPLEX OR QUADRUPLEX COMPLEXES

BACKGROUND OF THE INVENTION

1. Field of Invention

The invention relates to nucleobase binding in complexes, such as duplexes, triplexes and quadruplexes, and more particularly to methods wherein such complexes are formed by specific binding between single-stranded or double-stranded nucleobase-containing probes and single-stranded or double-stranded nucleobase-containing target sequences.

2. Description of Related Art

The Watson-Crick model of nucleic acids has been the accepted standard in molecular biology for nearly fifty years. As recounted by James Watson in his book entitled "A Personal Account of the Discovery of the Structure of DNA," (1968), the Watson-Crick model, which won Watson and Crick the Nobel Prize, arose from the ashes of their abandoned theory that bases bind to like bases on opposing strands (Watson at p. 125). Watson described how he abandoned his "briefly considered like-with-like pairing" model when he realized the advantages of a model based on A:T and G:C binding. Id.

Although antiparallel nucleic acid duplexes first suggested by Watson and Crick are the most widely studied type of multiple-strand nucleic acid structures, it has been discovered that nucleic acids also form triplex structures and quadruplex structures under certain conditions.

Until recently, binding among three nucleic acid strands to form a triplex was widely believed to be confined to very limited species of nucleic acids (e.g., polypurine or polypyrimidine sequences). See, e.g., Floris et al., "Effect of cations on purine-purine-pyrimidine triple helix formation in mixed-valence salt solutions," 260 Eur. J. Biochem. 801-809 (1999). Moreover, canonical triplex binding or hybridization was thought to be based on Hoogsteen binding between limited varieties of adjacent nucleobases, rather than Watson-Crick base pairing. See, e.g., Floris et al. and U.S. Pat. No. 5,874,555 to Dervan et al. However, the inventors have recently disclosed in several patent applications that specifically bound mixed base sequence triplex nucleic acids based on Watson-Crick base pairing can be created and used as the basis for a highly accurate and sensitive assay for specific binding. See U.S. patent applications Ser. Nos. 09/613,263 and 09/468,679, respectively filed Jul. 10, 2000 and Dec. 21, 1999.

Zhurkin et al., 239 J. Mol. Biol. 181 (1994) discloses the possibility of parallel DNA triplexes; however, these triplexes are said to be created by the third strand binding in the major groove of the duplex in the presence of recombination proteins, such as RecA protein.

As has been the case with triplex nucleic acids, the conventional wisdom regarding quadruplex nucleic acids has been that such peculiar structures only exist under relatively extreme conditions for a narrow class of nucleic acids. In particular, Sen et al. (Nature 334:364-366 (1988)) disclosed that guanine-rich oligonucleotides can spontaneously self-assemble into four-stranded helices in vitro. Sen et al. (Biochemistry 31:65-70 (1992)) disclosed that these four-stranded complexes can further associate into superstructures composed of 8, 12, or 16 oligomers.

Marsh et al. (Biochemistry 33:10718-10724 (1994), and Nucleic Acids Research 23:696-700 (1995)) disclosed that some guanine-rich oligonucleotides can also assemble in an offset, parallel alignment, forming long "G-wires". These higher-order structures are stabilized by G-quartets that consist of four guanosine residues arranged in a plane and held together through Hoogsteen base pairings. According to Sen et al. (Biochemistry 31:65-70 (1992)), at least three contiguous guanines within the oligomer are critical for the formation of these higher order structures.

It has been suggested that four-stranded DNAs play a role in a variety of biological processes, such as inhibition of HIV-1 integrase (Mazumder et al., Biochemistry 35:13762-13771 (1996)), formation of synapsis during meiosis (Sen et al., Nature 334:364-366 (1988)), and telomere maintenance (Williamson et al., Cell 59:871-880 (1989); Baran et al., Nucleic Acids Research 25:297-303 (1997)). It has been further suggested that controlling the production of guanine-rich quadruplexes might be the key to controlling such biological processes. For example, U.S. Pat. No. 6,017,709 to Hardin et al. suggests that telomerase activity might be controlled through drugs that inhibit the formation of guanine quartets.

U.S. Pat. No. 5,888,739 to Pitner et al. discloses that G-quartet based quadruplexes can be employed in an assay for detecting nucleic acids. Upon hybridization to a complementary oligonucleotide, the G-quartet structure unfolds or linearizes, thereby increasing the distance between donor and acceptor moieties on different parts of the G-quartet structure, resulting in a decrease in their interaction and a detectable change in a signal (e.g., fluorescence) emitted from the structure.

U.S. Pat. No. 5,912,332 to Agrawal et al. discloses a method for the purification of synthetic oligonucleotides, wherein the synthetic oligonucleotides hybridize specifically with a desired, full-length oligonucleotide and concomitantly form a multimer aggregate, such as quadruplex DNA. The multimer aggregate containing the oligonucleotide to be purified is then isolated using size-exclusion techniques.

Despite the foregoing developments, a need has continued to exist to systematically investigate and catalogue all specific interactions between mixed base sequence nucleic acids and to create new, effective and rapid methods for producing and analyzing specific interaction between nucleic acids and/or nucleic acid analogues.

All references cited herein are incorporated herein by reference in their entireties.

BRIEF SUMMARY OF THE INVENTION

The invention provides a complex comprising: (1) a probe containing a heteropolymeric probe sequence of nucleic acids or nucleic acid analogues; and (2) a target containing a heteropolymeric target sequence of nucleic acids or nucleic acid analogues, wherein: (a) at least one of the probe and the target is purified or synthetic; and (b) the heteropolymeric probe sequence is bonded to the heteropolymeric target sequence by Watson-Crick complementary base interaction or by homologous base interaction, provided that when the complex is a duplex and the heteropolymeric probe sequence is antiparallel to the heteropolymeric target sequence, the heteropolymeric probe sequence is bonded to the heteropolymeric target sequence by homologous base interaction, and provided that when the complex is a triplex, the complex is free of recombination proteins.

Also provided is a method for assaying a target, the method comprising: (1) providing a sample comprising the target containing a heteropolymeric target sequence of nucleic acids or nucleic acid analogues; (2) providing a probe containing a heteropolymeric probe sequence of nucleic acids or nucleic acid analogues; (3) providing a hybridization mixture comprising the target, the probe, water, and a buffer; (4) incubating the hybridization mixture for an incubation time effective to bind the heteropolymeric target sequence to the heteropolymeric probe sequence to provide a complex; and (5) detecting a signal correlated with binding affinity between the probe and the target to assay the target, wherein the heteropolymeric probe sequence is bonded to the heteropolymeric target sequence by Watson-Crick complementary base interaction or by homologous base interaction, provided that when the complex is a duplex and the heteropolymeric probe sequence is antiparallel to the heteropolymeric target sequence, the heteropolymeric probe sequence is bonded to the heteropolymeric target sequence by homologous base interaction, and provided that when the complex is a triplex, the complex is free of recombination proteins.

BRIEF DESCRIPTION OF SEVERAL VIEWS OF THE DRAWINGS

The invention will be described in conjunction with the following drawings in which like reference numerals designate like elements and wherein:

FIGS. 1A, 1B, 1C, 2A, 2B, 3A, 3B, 4, 5A, 5B, 6, 7, 8, 9, 10A, 10B, 11A, 11B, 12A, 12B, 13A and 13B are composite graphs of fluorescent intensity plotted as a function of wavelength for each sample analyzed;

FIGS. 14A, 14B and 14C are composite graphs of fluorescent intensity plotted as a function of time for each sample analyzed.

DETAILED DESCRIPTION OF THE INVENTION

Figure 15:
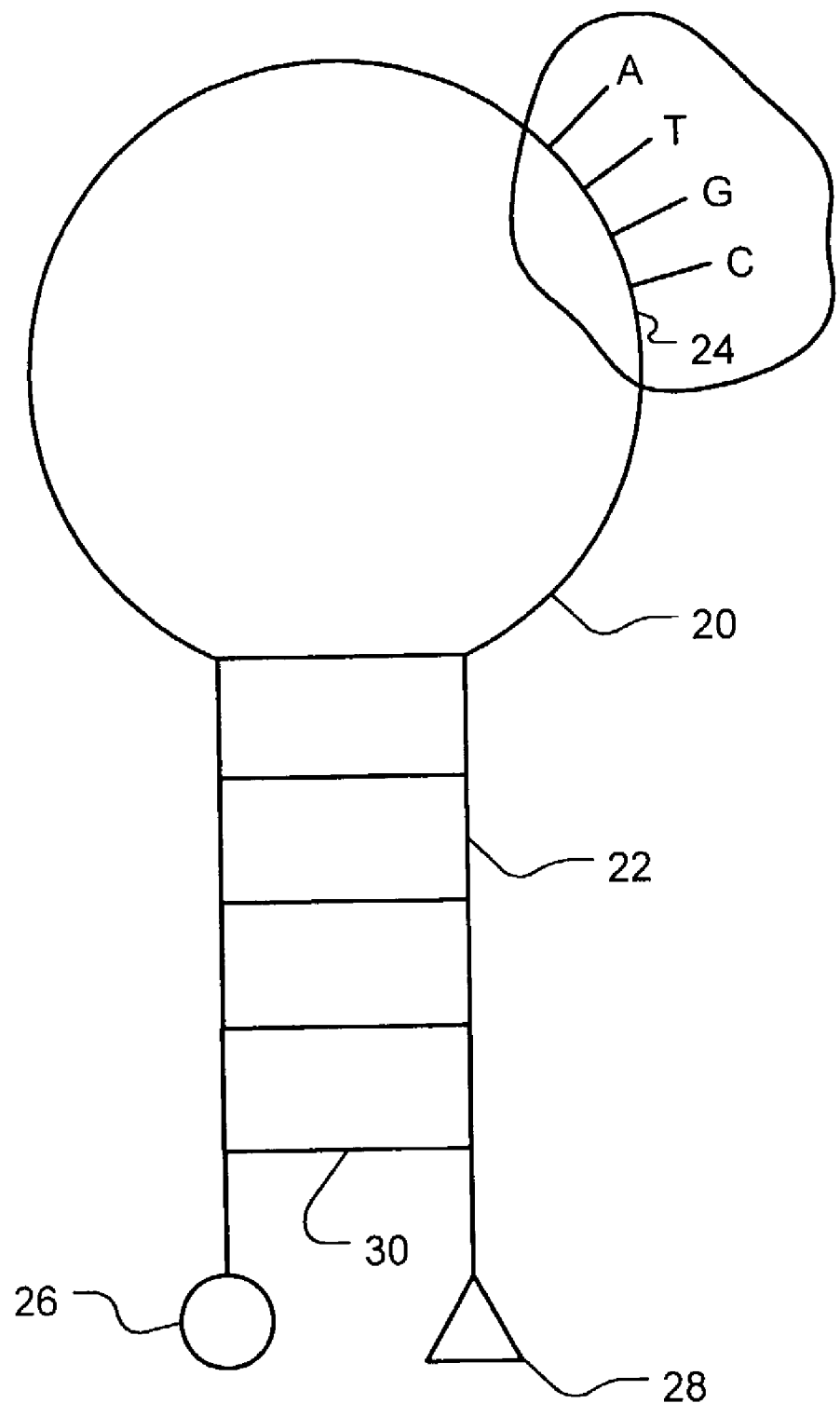
FIG. 15 is a partially enlarged schematic view of a loop and stem embodiment of the invention.

The invention flows from our elucidation of the specific binding properties of heteropolymeric nucleic acid strands. We have previously disclosed the specific binding of a heteropolymeric strand to duplex nucleic acid and the specific binding of duplex nucleic acid to other duplex nucleic acid. We now disclose that heteropolymeric nucleic acids (and/or their analogues) can specifically bind to each other by homologous base bonding as well as by Watson-Crick base interaction, and that base bonding is not limited to strands having antiparallel directionality relative to each other. Thus, heteropolymeric nucleic acids (and/or their analogues) can specifically bind to each other with parallel or antiparallel directionality, wherein the bases bond by homologous base bonding and/or Watson-Crick base bonding rules.

The invention is more than merely the disclosure of unorthodox binding properties of nucleic acids. The invention encompasses novel compounds, as well as methods for the analysis of nucleic acids, diagnostic methods, therapeutic methods, prophylactic methods, gene therapy and genetic engineering.

The invention encompasses novel duplex, triplex and quadruplex complexes of nucleic acids (and/or analogues thereof).

Nucleic acid strands have inherent directionality. The conventional wisdom holds that strands of opposite directionality, i.e., which are antiparallel in their orientation to one another, can form a duplex through Watson-Crick complementary binding of their respective bases.

Certain duplexes according to the invention, on the other hand, comprise two strands of nucleic acid (and/or nucleic acid analogues) hybridized in parallel relation to one another, wherein specific binding is either through homologous base pairing or Watson-Crick base pairing. Conventional wisdom holds that such duplexes do not exist, or at least would be extremely unstable due to, e.g., backbone irregularities necessitated by the conformational requirements of parallel base bonding. Even more surprising is our discovery that under appropriate hybridization conditions, homologous bonding demonstrates specificity and stability rivaling that of Watson-Crick complementary antiparallel duplex.

The invention also encompasses duplexes containing two strands of nucleic acid (and/or nucleic acid analogues) hybridized in antiparallel relation to one another, wherein specific binding is through homologous base pairing.

As used herein, the terms "Watson-Crick base pairing", "complementary base pairing" and the like are intended to define specific association between opposing or adjacent pairs of nucleic acid and/or nucleic acid analogue strands via matched bases (e.g., A:T; G:C and/or A:U). In the context of non-canonical complexes described herein, including parallel duplexes, parallel and antiparallel triplexes, and parallel and antiparallel quadruplexes, terms like "Watson-Crick base bonding" and "complementary base bonding" are intended to denote bonding between A and T, A and U and/or G and C, but not necessarily in the edgewise, planar conformation first described by Watson and Crick. In addition to the conventional binding motif first proposed by Watson and Crick (the "W-C motif"), and conformational variants thereof encompassed by the foregoing definition of Watson-Crick base bonding, the present invention encompasses complexes formed by homologous base bonding. In homologous base bonding, bases bond specifically with identical bases rather than complementary bases. Thus, in the "homologous motif", homologous base pairs include A:A, G:G, C:C, T:T and U:U.

The binding by the bases of nucleic acid strands is affected or conditioned by a number of factors, particularly the binding potential of the strands pursuant to either the W-C motif or homologous motif, and ionic conditions (e.g., salt concentration and/or type). Salty conditions tend to favor the formation of Watson-Crick bonding over homologous bonding. Homologous motif quadruplexes are favored over W-C motif quadruplexes under identical buffer conditions probably because the localized environment can become relatively low-salt, based on the presence of the charged backbones of the two duplex nucleic acids.

Each strand in a complex of the invention can comprise any sequence of nucleobases and/or nucleobase analogues, provided the nucleobases are related to the nucleobases to which they are to specifically bind by either the W-C motif or the homologous motif. Contrary to certain teachings of the prior art, the target and probe need not be homopolymeric to achieve binding, even in the case of triplex or quadruplex formation. Thus, in certain embodiments, the probe nucleobases are arranged in a heteropolymeric probe sequence of interspersed purines and pyrimidines, and the target nucleobases are arranged in a target sequence at least partially complementary or partially homologous to the probe sequence. For example, the probe sequence can contain 25% to 75% purine bases and 75% to 25% pyrimidine bases in any order. Complexes of the invention can form from heteropolymeric sequences, which as defined herein, means sequences containing at least one purine nucleobase or purine analogue and at least one pyrimidine nucleobase or pyrimidine analogue in at least their hybridizing segments. Heteropolymeric sequences preferably lack homopolymeric fragments greater than 5 bases long. Other nucleobases are also suitable for use in the invention, such as, e.g., synthetic analogues of naturally occurring bases which have specific Watson-Crick and/or homologous binding affinities to other bases.

In addition to duplexes, complexes of the invention also include triplexes and quadruplexes, wherein opposing heteropolymeric strands are linked by Watson-Crick complementary bases or by homologous bases, and the relative directionality of the bound sequences is parallel or antiparallel to one another.

A probe strand can specifically bind in the major or minor groove of a double-stranded target. Further, the bases of a single-stranded probe can interact specifically with bases on one or both strands of a double-stranded target. Similarly, the bases of each strand of a double-stranded probe can interact specifically with bases on one or both strands of a double-stranded target in quadruplex complexes of the invention.

In certain triplex and quadruplex embodiments, each nucleobase binds to one or two other nucleobases. Thus, in addition to the traditional duplex Watson-Crick base pairs and the duplex homologous base pairs described above, such embodiments include the following Watson-Crick base binding triplets: A:T:A, T:A:T, U:A:T, T:A:U, A:U:A, U:A:U, G:C:G and/or C:G:C (including $C^+$:G:C, and/or any other ionized species of base), and/or the following homologous base triplets: A:A:T, T:T:A, U:U:A, T:U:A, A:A:U, U:T:A, G:G:C and/or C:C:G (including $C:C^+$:G, and/or any other ionized species of base).

Thus, in certain quadruplex embodiments wherein the probe is defined as a duplex of a first and a second strand and the target is defined as a duplex of a third and a fourth strand, it is believed that the bases of the first and third strands also bind to each other, in addition to: (a) the binding between opposing bases of the first and second strands; (b) the binding between opposing bases of the third and fourth strands; and (c) the binding between opposing bases of the second and fourth strands.

In certain embodiments of the triplex and quadruplex structures of the invention, no binding sequence of bases is contiguous with another binding sequence of bases. That is, there are at least three separate strands. Although folded conformations and the like (e.g., hairpin turns, etc.) are within the scope of the invention, folded portions of a single strand do not make the strand count more than once toward the minimum of three separate strands.

Complexes of the invention preferably do not rely on Hoogsteen bonding or G-G quartets for maintenance of the complex structure, although Hoogsteen bonding and/or G-G quartets may be present. That is, complexes of the invention are preferably substantially free of Hoogsteen bonding, and substantially free of G-G quartets.

In certain complexes of the invention: (a) the probe is a heteropolymeric multistranded parallel complex; (b) bases of the probe are homologously bound in a first plane; (c) the target is a heteropolymeric multistranded parallel complex; and (d) bases of the target are homologously bound in a second plane. In certain other complexes of the invention: (a) the probe is a heteropolymeric multistranded parallel complex; (b) bases of the probe are bound pursuant to a Watson-Crick motif in a first plane; (c) the target is a heteropolymeric multistranded parallel complex; and (d) bases of the target are bound pursuant to a Watson-Crick motif in a second plane.

Each strand of the complex independently comprises a nucleic acid having a deoxyribose phosphate or ribose phosphate backbone (e.g., DNA, RNA, mRNA, hnRNA, rRNA, tRNA or cDNA) or a nucleic acid analogue. Preferred nucleic acid analogues contain an uncharged or partially charged backbone (i.e., a backbone having a charge that is not as negative as a native DNA backbone), and include, e.g., PNA and LNA. Certain embodiments are free of PNA.

At least a portion of the complex is isolated, purified, artificial or synthetic.

In embodiments, a portion of the complex is a PCR amplified product.

The complexes of the invention can be present in solution, on a solid support, in vitro, in vivo or in silico. The solid support can be electrically conductive (e.g., an electrode) or non-conductive. In addition, the complexes can be optically mapped or sequenced after being elongated, as taught in U.S. Pat. Nos. 6,147,198 and 5,720,928 to Schwartz.

Complexes of the invention can be provided by a method comprising: (a) providing a hybridization mixture comprising a target containing a heteropolymeric target sequence of nucleic acids or nucleic acid analogues, a probe containing a heteropolymeric probe sequence of nucleic acids or nucleic acid analogues, water, and a buffer; and (b) incubating said hybridization mixture for an incubation time effective to hybridize said heteropolymeric target sequence to said heteropolymeric probe sequence to provide the complex.

The hybridization mixture can include any conventional medium known to be suitable for preserving nucleotides. See, e.g., Sambrook et al., "Molecular Cloning: A Lab Manual," Vol. 2 (1989). For example, the medium can comprise nucleotides, water, buffers and standard salt concentrations. When divalent cations are used exclusively to promote triplex or quadruplex formation, chelators such as EDTA or EGTA should not be included in the reaction mixtures.

Specific binding between complementary bases occurs under a wide variety of conditions having variations in temperature, salt concentration, electrostatic strength, and buffer composition. Examples of these conditions and methods for applying them are known in the art. Our copending U.S. patent application Ser. No. 09/885,731, filed Jun. 20, 2001, discloses conditions particularly suited for use in this invention.

Unlike many Hoogsteen-type complexes, which are unstable or non-existent at pH levels above about 7.6, the complexes of the invention are stable over a wide range of pH levels, preferably from about pH 5 to about pH 9.

Complexes of the invention can be provided for analytic, diagnostic, therapeutic and/or engineering purposes. The complexes can be used to analyze, diagnose and/or treat conditions associated with infection by an organism or virus. The organism or virus can be quantitated, if desired.

Complexes of the invention can be formed under conventional hybridization conditions, under triplex hybridization conditions, under quadruplex hybridization conditions or under conditions of in situ hybridization. It is preferred that complexes be formed at a temperature of about 2° C. to about 55° C. for about two hours or less. In certain embodiments, the incubation time is preferably less than five minutes, even at room temperature. Longer reaction times are not required, but incubation for up to 24 hours in most cases does not adversely affect the complexes. The fast binding times of the complexes of the invention contrast with the much longer binding times necessary for Hoogsteen bound complexes.

The promoter in the hybridization medium is preferably an intercalating agent or a cation, as disclosed in U.S. patent application Ser. No. 09/613,263, filed Jul. 10, 2000. The intercalators are optionally fluorescent. The intercalating agent can be, e.g., a fluorophore, such as a member selected from the group consisting of YOYO-1, TOTO-1, YOYO-3, TOTO-3, POPO-1, BOBO-1, POPO-3, BOBO-3, LOLO-1, JOJO-1, cyanine dimers, YO-PRO-1, TO-PRO-1, YO-PRO-3, TO-PRO-3, TO-PRO-5, PO-PRO-1, BO-PRO-1, PO-PRO-3, BO-PRO-3, LO-PRO-1, JO-PRO-1, cyanine monomers, ethidium bromide, ethidium homodimer-1, ethidium homodimer-2, ethidium derivatives, acridine, acridine orange, acridine derivatives, ethidium-acridine heterodimer, ethidium monoazide, propidium iodide, SYTO dyes, SYBR Green 1, SYBR dyes, Pico Green, SYTOX dyes and 7-aminoactinomycin D.

Suitable cations include, e.g., monovalent cations, such as $Na^+$ (preferably at a concentration of 40 mM to 200 mM), $K^+$ (preferably at a concentration of 40 mM to 200 mM), and other alkali metal ions; divalent cations, such as alkaline earth metal ions (e.g., $Mg^{+2}$ and $Ca^{+2}$) and divalent transition metal ions (e.g., $Mn^{+2}$, $Ni^{+2}$, $Cd^{+2}$, $Co^{+2}$ and $Zn^{+2}$); and cations having a positive charge of at least three, such as $Co(NH_3)_6^{+3}$, trivalent spermidine and tetravalent spermine. $Mn^{+2}$ is preferably provided at a concentration of 10 mM to 45 mM. $Mg^{+2}$ is preferably provided at a concentration of 10 mM to 45 mM. $Ni^{+2}$ is preferably provided at a concentration of about 20 mM. In embodiments, $Mg^{+2}$ and $Mn^{+2}$ are provided in combination at a concentration of 1 mM each, 2 mM each, 3 mM each . . . 40 mM each (i.e., 1-40 mM each).

The amount of cation added to the medium in which the complex forms depends on a number of factors, including the nature of the cation, the concentration of probe, the concentration of target, the presence of additional cations and the base content of the probe and target. The preferred cation concentrations and mixtures can routinely be discovered experimentally. For triplexes, it is preferred to add cation(s) to the medium in the following amounts: (a) 10 mM-30 mM $Mn^{+2}$; (b) 10 mM-20 mM $Mg^{+2}$; (c) 20 mM $Ni^{+2}$; or (d) 1 mM-30 mM of each of $Mn^{+2}$ and $Mg^{2+}$. For quadruplexes, it is preferred to add cation(s) to the medium in the following amounts: (a) 10 mM-45 mM $Mn^{+2}$; (b) 10 mM-45 mM $Mg^{+2}$; or (c) 10 mM-40 mM of each of $Mn^{+2}$ and $Mg^{+2}$.

Although not required, other promoters include, e.g., single stranded binding proteins such as Rec A protein, T4 gene 32 protein, *E. coli* single stranded binding protein, major or minor nucleic acid groove binding proteins, viologen and additional intercalating substances such as actinomycin D, psoralen, and angelicin. Such facilitating reagents may prove useful in extreme operating conditions, for example, under abnormal pH levels or extremely high temperatures. Certain methods for providing complexes of the invention are conducted in the absence of protein promoters, such as Rec A and/or other recombination proteins.

The invention provides a rapid, sensitive, environmentally friendly, and safe method for assaying binding. The inventive assay can be used to, e.g., identify accessible regions in folded nucleotide sequences, to determine the number of mismatched base pairs in a hybridization complex, and to map genomes.

The inventive assay not only detects the presence of specific probe-target binding, but also provides qualitative and quantitative information regarding the nature of interaction between a probe and target. Thus, the invention enables the practitioner to distinguish among a perfect match, a one base pair mismatch, a two base pair mismatch, a three base pair mismatch, a one base pair deletion, a two base pair deletion and a three base pair deletion arising between a sequence in the double-stranded probe or single-stranded probe and in a sequence in the double-stranded or single-stranded target.

Embodiments of the invention comprise calibrating the measured signal (e.g., optical, fluorescence, chemiluminescence, electrochemiluminescence, electrical or electromechanical properties) for a first probe-target mixture against the same type of signal exhibited by other probes combined with the same target, wherein each of the other probes differs from the first probe by at least one base.

A calibration curve can be generated, wherein the magnitude of the measured signal (e.g., fluorescent intensity) is a function of the binding affinity between the target and probe. As the binding affinity between the target and a plurality of different probes varies with the number of mismatched bases, the nature of the mismatch(es) (e.g., A:G vs. A:C vs. T:G vs. T:C, etc. in the W-C motif), the location of the mismatch(es) within the complex, etc., the assay of the invention can be used to sequence the target.

In embodiments, the signal measured can be the fluorescent intensity of a fluorophore included in the test sample. In such embodiments, the binding affinity between the probe and target can be directly or inversely correlated with the intensity, depending on whether the fluorophore signals hybridization through signal quenching or signal amplification. Under selected conditions, the fluorescent intensity generated by intercalating agents can be directly correlated with probe-target binding affinity, whereas the intensity of preferred embodiments employing a non-intercalating fluorophore covalently bound to the probe can be inversely correlated with probe-target binding affinity. The fluorescent intensity decreases for non-intercalating fluorophores as the extent of matching (e.g., the amount of matches vs. mismatches and/or the types of mismatches) between the probe and target increases, preferably over a range inclusive of 0-2 mismatches and/or deletions, more preferably over a range inclusive of 0-3 mismatches and/or deletions.

The invention enables quantifying the binding affinity between probe and target. Such information can be valuable for a variety of uses, including designing antisense drugs with optimized binding characteristics.

The assay of the invention is preferably homogeneous. The assay can be conducted without separating free probe and free target from the hybridization complex prior to detecting the magnitude of the measured signal. The assay does not require a gel separation step, thereby allowing a great increase in testing throughput. Quantitative analyses are simple and accurate. Consequently the binding assay saves a lot of time and expense, and can be easily automated. Furthermore, it enables binding variables such as buffer, pH, ionic concentration, temperature, incubation time, relative concentrations of probe and target sequences, intercalator concentration, length of target sequences, length of probe sequences, and possible cofactor (i.e., promoter) requirements to be rapidly determined.

The assay can be conducted in, e.g., a solution within a well or microchannel, on an impermeable surface or on a biochip. In certain embodiments, the target is provided in the hybridization medium before the probe, and the probe is provided in dehydrated form prior to rehydration by contact with the hybridization medium.

In certain embodiments, the inventive assay is conducted without providing a signal quenching agent on the target or on the probe.

The invention obviates the need to denature the target prior to assaying. It is surprising that the inventors have been able to specifically assay heteropolymeric triplexes and quadruplexes, wherein the interaction between the probes and targets is based on Watson-Crick or homologous base interaction (at least in the sense that A binds to T (or U, in the case of RNA) and G binds to C), rather than the very limited Hoogsteen model of complex hybridization of, e.g., Pitner et al., supra.

Suitable targets are preferably 8 to $3.3 \times 10^9$ base pairs long, and can be single or double-stranded.

Probes of the invention are preferably 2 to 75 bases long (more preferably 5 to 30 bases long), and can be single or double-stranded. Thus, suitable probes for use in the inventive assay include, e.g., ssDNA, RNA, ssPNA, LNA, dsDNA, dsRNA, DNA:RNA hybrids, dsPNA, PNA:DNA hybrids and other single and double-stranded nucleic acids and nucleic acid analogues having uncharged, partially-charged, sugar phosphate and/or peptide backbones. The length of the probe can be selected to match the length of the target.

The probe can be unfolded or folded. When the probe is folded, it is preferred that the probe contains loop 20 and stem 22 adjacent to the loop, such as depicted in FIG. 15. Heteropolymeric probe sequence 24 is located partially or entirely within stem 22 or loop 20. FIG. 15 shows the most preferred location for heteropolymeric probe sequence 24, entirely within loop 20. This portion of loop 20 is enlarged to show an exemplary base sequence (A-T-G-C) of heteropolymeric probe sequence 24.

In embodiments wherein heteropolymeric probe sequence 24 is located in loop 20, it is preferred that binding of the heteropolymeric target sequence (not shown) to the heteropolymeric probe sequence causes the opposing strands of stem 22 to separate, thereby opening loop 20. As the opposing strands separate, the distance between donor 26 and acceptor 28 increases, resulting in a change in a detectable signal, which is particularly useful for a method of detecting binding between the heteropolymeric probe sequence and the heteropolymeric target sequence.

In certain embodiments, donor 26 emits the signal and acceptor 28 quenches the signal. In certain other embodiments, donor 26 transfers energy to acceptor 28 and the acceptor emits the signal. Thus, donor 26 and acceptor 28 can be, e.g., a fluorescence resonance energy transfer (FRET) pair or an electrochemiluminescent pair. Although donor 26 and acceptor 28 are schematically depicted in FIG. 15 as being different from each other, it is possible for them to be identical to each other. Similarly, these embodiments of the invention are not limited to only one acceptor-donor pair placed at the free ends of stem 22. One or more acceptor(s) and one or more donor(s) can be placed (e.g., via covalent bonding) throughout stem 22 in such "molecular beacon" embodiments. The number of crosslinks 30 between adjacent sequences of stem 22 varies and can be less or more than the five depicted in FIG. 15.

The use of certain single-stranded loop and stem structures as molecular beacons to detect target nucleic acids is disclosed in, e.g., U.S. Pat. No. 5,925,517 to Tyagi et al.; Bonnet et al., Proc Natl Acad Sci USA 1998 July 21; 95(15):8602-6; and Phys Rev Lett 2000 September 11;85 (11):2400-3. However, these references do not disclose or suggest the use of molecular beacons to detect probe-target hybridization according to the novel motifs of this invention.

Embodiments containing the heteropolymeric probe sequence in the stem can have enhanced specificity for perfectly matched heteropolymeric target sequences relative to heteropolymeric probe sequences lacking an adjacent loop (possibly because of the enhanced stability of the resulting complex of perfectly matched target and loop-containing probe). Some advantages of loop and stem structures in conventional nucleic acid hybridization studies are suggested by Riccelli et al. (Nucleic Acids Research 29:996-1004 (2001)) and U.S. Pat. No. 5,770,365 to Lane et al. The present invention comprises the use of loop and stem probes containing the novel complexes of the invention and/or adapted to form novel complexes of the invention when bound to the target. Thus, the loop and/or the stem of the probe can be completely or partially single-stranded and/or double-stranded, and can even be triple-stranded or quadruple-stranded alone or after hybridization to the target. The instant invention does not require the use of radioactive probes, which are hazardous, tedious and time-consuming to use, and need to be constantly regenerated. Probes of the invention are preferably safe to use and stable for years. Accordingly, probes can be made or ordered in large quantities and stored.

The complex is preferably detected by a change in at least one label. The at least one label can be attached to the probe and/or the target, and/or can be free in the test medium. The at least one label can comprise at least two moieties.

The label is preferably at least one member selected from the group consisting of a spin label, a fluorophore, a chromophore, a chemiluminescent agent, an electro-chemiluminescent agent, a radioisotope, an enzyme, a hapten, an antibody and a labeled antibody. Preferably, the complex is detected by at least one emission from the label or by monitoring an electronic characteristic of the complex.

The labeled antibody can be, e.g., a labeled anti-nucleic acid/nucleic acid antibody, which can be labeled with a detectable moiety selected from the group consisting of a fluorophore, a chromophore, a spin label, a radioisotope, an enzyme, a hapten, a chemiluminescent agent and an electro-chemiluminescent agent.

The complex can be detected under at least one varied condition, such as disclosed in U.S. patent application Ser. No. 09/490,273, filed Jan. 24, 2000. Suitable varied conditions include, e.g., (a) a change in nonaqueous components of the test medium, (b) a change in a pH of the test medium, (c) a change in a salt concentration of the test medium, (d) a change of an organic solvent content of the test medium, (e) a change in a formamide content of the test medium, (f) a change in a temperature of the test medium, and (g) a change in chaotropic salt concentration in the test medium. In addition, the varied condition can be the application of a stimulus, such as, e.g., electric current (DC and/or AC), photon radiation (e.g., laser light), or electromagnetic force. The stimulus can be applied constantly or pulsed. Detection can be accomplished through the use of a single varied condition, or through a combination of conditions varied serially.

The response of a characteristic of the complex in the test medium to the varied condition or stimulus can be monitored to detect the complex. The characteristic can be, e.g., electrical conductance or Q (a resonant structure of a transmission line or changes in phase or amplitude of a signal propagated in the transmission line in the test medium).

In embodiments, the detection method comprises: (a) detecting a signal from a label, wherein the signal is correlated to a binding affinity between said probe and said target; (b) varying a condition of a test medium; (c) detecting a subsequent signal; and (d) comparing the signal and the subsequent signal. The varying and the detecting can be repeated at least once or performed only once.

The label is preferably a fluorophore. Both intercalating and non-intercalating fluorophores are suitable for use in the invention. The fluorophore can be free in solution, covalently bound to the probe and/or covalently bound to the target. When the fluorophore is covalently bound to the probe, it is preferably bound to the probe at either end. Preferred fluorescent markers include biotin, rhodamine, acridine and fluorescein, and other markers that fluoresce when irradiated with exciting energy. Suitable non-intercalating fluorophores include, e.g., alexa dyes, BODIPY dyes, biotin conjugates, thiol reactive probes, fluorescein and its derivatives (including the "caged probes"), Oregon Green, Rhodamine Green and QSY dyes (which quench the fluorescence of visible light excited fluorophores).

The excitation wavelength is selected (by routine experimentation and/or conventional knowledge) to correspond to this excitation maximum for the fluorophore being used, and is preferably 200 to 1000 nm. Fluorophores are preferably selected to have an emission wavelength of 200 to 1000 nm. In preferred embodiments, an argon ion laser is used to irradiate the fluorophore with light having a wavelength in a range of 400 to 540 nm, and fluorescent emission is detected in a range of 500 to 750 nm.

The assay of the invention can be performed over a wide variety of temperatures, such as, e.g., from about 2 to about 60° C. Certain prior art assays require elevated temperatures, adding cost and delay to the assay. On the other hand, the invention can be conducted at room temperature or below (e.g., at a temperature below 25° C.).

The reliability of the invention is independent of guanine and cytosine content in either the probe or the target. In the traditional W-C motif, since G:C base pairs form three hydrogen bonds, while A:T base pairs form only two hydrogen bonds, target and probe sequences with a higher G or C content are more stable, possessing higher melting temperatures. Consequently, base pair mismatches that increase the GC content of the hybridized probe and target region above that present in perfectly matched hybrids may offset the binding weakness associated with a mismatched probe.

The inventive assay is extremely sensitive, thereby obviating the need to conduct PCR amplification of the target. For example, it is possible to assay a test sample having a volume of about 20 microliters, which contains about 10 femtomoles of target and about 10 femtomoles of probe. Embodiments of the invention are sensitive enough to assay targets at a concentration of $5 \times 10^{-9}$ M, preferably at a concentration of not more than $5 \times 10^{-10}$ M. Embodiments of the invention are sensitive enough to employ probes at a concentration of $5 \times 10^9$ M, preferably at a concentration of not more than $5 \times 10^{-10}$ M. It should go without saying that the foregoing values are not intended to suggest that the method cannot detect higher concentrations.

The ratio of probe to target is preferably about 1:1 to about 1000:1.

Unlike certain prior art assays, the invention not only detects the presence of hybridization (i.e., binding), but also provides qualitative and quantitative information regarding the nature of binding between a probe and target. Thus, the invention enables the practitioner to: (a) detect the presence of the target in the test medium; (b) detect allelic or heterozygous variance in the target; (c) quantitate the target; (d) detect an extent of complementarity (in the case of binding in the W-C motif) or homologousness (in the case of binding in the homologous motif) between the probe and the target; and (e) detect haplotypes.

We have noticed that duplexes which complex parallel strands of nucleic acid containing complementary base sequences bind to form triplexes at a different rate and bind as a culmination of a very different process than do bases in a double helix formed by nucleic acid strands of opposite directionality. Strands of opposite directionality (i.e., antiparallel strands) readily present regularly spaced bases in a planar orientation to the bases opposite with minimal backbone distortion.

The various complexes of the invention comprise a probe containing a heteropolymeric probe sequence of nucleobases and/or nucleobase analogues, and a target containing a heteropolymeric target sequence of nucleobases and/or nucleobase analogues. The complex is synthetic or purified in that at least one of either the probe or the target is synthetic or purified. The backbone of the probe is a deoxyribose phosphate backbone such as in DNA, or a peptide-like backbone such as in PNA, or is of some other uncharged or partially charged (negatively or positively) moieties.

In certain embodiments, the probe and target are single-stranded and the complex is a duplex. When said probe and target are a duplex they have parallel directionality with W-C complementary or homologous binding, or have antiparallel directionality with homologous binding.

In other embodiments, either the probe or the target is single-stranded and the other of said probe or target is double-stranded and the resulting complex is a triplex. This complex can be free of PNA.

In certain embodiments, the triplex contains a heteropolymeric probe sequence parallel to a heteropolymeric target sequence, wherein the heteropolymeric probe sequence is bonded to the heteropolymeric target sequence by homologous base binding or Watson-Crick complementary base binding. In certain other embodiments, the heteropolymeric probe sequence is antiparallel to the heteropolymeric target sequence and the heteropolymeric probe sequence is bonded to the heteropolymeric target sequence by homologous base binding or Watson-Crick complementary base binding.

In certain embodiments of the triplex complex, the target includes a first strand containing a heteropolymeric target sequence and a second strand containing a second heteropolymeric target sequence that is Watson-Crick complementary and antiparallel to the first heteropolymeric target sequence. The heteropolymeric probe sequence is bonded to the first heteropolymeric target sequence by homologous base bonding and is also bonded to the second heteropolymeric target sequence by Watson-Crick complementary base bonding.

In certain other embodiments of the triplex complex, the target includes a first strand containing a heteropolymeric target sequence and a second strand containing a second heteropolymeric target sequence that is Watson-Crick complementary and antiparallel to the first heteropolymeric target sequence. The heteropolymeric probe sequence is bonded to the first heteropolymeric target sequence by Watson-Crick complementary base bonding and is also bonded to the second heteropolymeric target sequence by homologous base bonding.

In certain embodiments, the probe and the target are double-stranded and the resulting complex is a quadruplex. This complex can be free of PNA.

In certain embodiments, the quadruplex contains a heteropolymeric probe sequence parallel or antiparallel to a heteropolymeric target sequence, wherein the heteropolymeric probe sequence is bonded to the heteropolymeric target sequence by homologous base binding or Watson-Crick complementary base binding. In such embodiments, the quadruplex complex contains a first probe strand containing said heteropolymeric probe sequence and a second probe strand containing a second heteropolymeric probe sequence that is complementary and antiparallel to the first probe sequence. The target includes a first target strand containing a heteropolymeric target sequence and a second target strand containing a second heteropolymeric target sequence that is complementary and antiparallel to the first.

In such quadruplex embodiments, the heteropolymeric probe sequence can bond to the heteropolymeric target sequence by Watson-Crick complementary or homologous base binding and the heteropolymeric probe sequence can optionally and additionally bond to the second heteropolymeric target sequence by homologous or Watson-Crick complementary base binding, respectively. Thus, when the heteropolymeric probe sequence bonds to the heteropolymeric target sequence by homologous base bonding, the heteropolymeric probe sequence optionally bonds to the second heteropolymeric target sequence by Watson-Crick complementary base bonding, and when the heteropolymeric probe sequence bonds to the heteropolymeric target sequence by Watson-Crick complementary base bonding, the heteropolymeric probe sequence optionally bonds to the second heteropolymeric target sequence by homologous base bonding.

The invention will be illustrated in more detail with reference to the following Examples, but it should be understood that the present invention is not deemed to be limited thereto.

EXAMPLES

Example 1

Complementary sense and antisense 50-mer ssDNA target sequences, derived from exon 10 of the human cystic fibrosis gene (Nature 380, 207 (1996)) were synthesized on a DNA synthesizer (Expedite 8909, PerSeptive Biosystems) and purified by HPLC. SsDNA oligonucleotides were dissolved in ddH$_2$O and diluted to a concentration of 1 pmole/µl. Equimolar amounts of complementary oligonucleotides were heated at 95° C. for 10 min and allowed to anneal gradually in the presence of 10 mM Tris, pH 7.5, 1 mM EDTA and 100 mM NaCl, as the temperature cooled to 21° C. over 1.5 hours. DsDNA oligonucleotides were diluted in ddH$_2$O at a concentration of 1 pmole/µl.

The sequence for the sense strand of the wild-type target DNA (SEQ ID NO:1) was: 5'-TGG CAC CAT TAA AGA AAA TAT CAT CTT TGG TGT TTC CTA TGA TGA ATA TA-3'.

The sequence for the antisense strand of the wild-type target DNA (SEQ ID NO:1) was: 5'-TAT ATT CAT CAT AGG AAA CAC CAA AGA TGA TAT TTT CTT TAA TGG TGC CA-3'.

SEQ ID NO:2 was a 50-mer mutant dsDNA target sequence identical to wild-type target DNA (SEQ ID NO:1) except for a one base pair mutation (underlined) at amino acid position 507 at which the wild-type sense strand sequence CAT was changed to C<u>G</u>T.

The sequence for the sense strand of SEQ ID NO:2 was:

5'-TGG CAC CAT TAA AGA AAA TAT C<u>G</u>T CTT TGG TGT TTC CTA TGA TGA ATA TA-3'.

The sequence for the antisense strand of SEQ ID NO:2 was:

5'-TAT ATT CAT CAT AGG AAA CAC CAA AGA <u>C</u>GA TAT TTT CTT TAA TGG TGC CA-3'.

SEQ ID NO:3 was a 50-mer mutant dsDNA target sequence identical to wild-type target DNA (SEQ ID NO:1) except for a consecutive two base pair mutation (underlined) at amino acid positions 506 and 507 at which the wild-type sense strand sequence CAT was changed to <u>AC</u>T.

The sequence for the sense strand of SEQ ID NO:3 was:

5'-TGG CAC CAT TAA AGA AAA TAT <u>AC</u>T CTT TGG TGT TTC CTA TGA TGA ATA TA-3'.

The sequence for the antisense strand of SEQ ID NO:3 was:

5'-TAT ATT CAT CAT AGG AAA CAC CAA AGA <u>GT</u>A TAT TTT CTT TAA TGG TGC CA-3'.

SEQ ID NO:4 was a 50-mer mutant dsDNA target sequence identical to wild-type target DNA (SEQ ID NO:1) except for a consecutive three base pair mutation (underlined) at amino acid positions 506 and 507 at which the wild-type sense strand sequence CAT was changed to <u>ACG</u>.

The sequence for the sense strand of SEQ ID NO:4 was:

5'-TGG CAC CAT TAA AGA AAA TAT <u>ACG</u> CTT TGG TGT TTC CTA TGA TGA ATA TA-3'.

The sequence for the antisense strand of SEQ ID NO:4 was:

5'-TAT ATT CAT CAT AGG AAA CAC CAA AG<u>C</u> <u>GT</u>A TAT TTT CTT TAA TGG TGC CA-3'.

SEQ ID NO:5 was a 50-mer dsDNA target sequence modified from SEQ ID NO:1, wherein the percent GC content was changed from 30% to 52%.

The sequence for the sense strand of the wild-type target DNA (SEQ ID NO:5) was: 5'-GAG CAC CAT GAC AGA CAC TGT CAT CTC TGG TGT GTC CTA CGA TGA CTC TG-3'.

The sequence for the antisense strand of the wild-type target DNA (SEQ ID NO:5) was: 5'-CAG AGT CAT CGT AGG ACA CAC CAG AGA TGA CAG TGT CTG TCA TGG TGC TC-3'.

SEQ ID NO:6 was a 50-mer mutant dsDNA target sequence identical to SEQ ID NO:5, except for a one base pair mutation (underlined), at which the sense strand sequence CAT was changed to C<u>G</u>T.

The sequence for the sense strand of mutant SEQ ID NO:6 was: 5'-GAG CAC CAT GAC AGA CAC TGT C<u>G</u>T CTC TGG TGT GTC CTA CGA TGA CTC TG-3'.

The sequence for the antisense strand of mutant SEQ ID NO:6 was: 5'-CAG AGT CAT CGT AGG ACA CAC CAG AGA <u>C</u>GA CAG TGT CTG TCA TGG TGC TC-3'.

SEQ ID NO:7 was a 50-mer mutant dsDNA target sequence identical to SEQ ID NO:5, except for a one base pair mutation (underlined), at which the sense strand sequence CTC was changed to CT<u>T</u>.

The sequence for the sense strand of mutant SEQ ID NO:7 was: 5'-GAG CAC CAT GAC AGA CAC TGT CAT CT<u>T</u> TGG TGT GTC CTA CGA TGA CTC TG-3'.

The sequence for the antisense strand of mutant SEQ ID NO:7 was: 5'-CAG AGT CAT CGT AGG ACA CAC CA<u>A</u> AGA TGA CAG TGT CTG TCA TGG TGC TC-3'.

SEQ ID NO:8 was a 50-mer mutant dsDNA target sequence identical to SEQ ID NO:5, except for a consecutive two base pair mutation (underlined), at which the sense strand sequence CAT was changed to <u>AC</u>T.

The sequence for the sense strand of mutant SEQ ID NO:8 was: 5'-GAG CAC CAT GAC AGA CAC TGT <u>AC</u>T CTC TGG TGT GTC CTA CGA TGA CTC TG-3'.

The sequence for the antisense strand of mutant SEQ ID NO:8 was: 5'-CAG AGT CAT CGT AGG ACA CAC CAG AGA <u>GT</u>A CAG TGT CTG TCA TGG TGC TC-3'.

SEQ ID NO:9 was a 47-mer mutant dsDNA target sequence identical to wild-type target DNA (SEQ ID NO:1) except for a consecutive three base pair deletion (indicated by three dots) at amino acid positions 507 and 508 at which the wild-type sense strand sequence CTT is deleted.

The sequence for the sense strand of SEQ ID NO:9 was:

5'-TGG CAC CAT TAA AGA AAA TAT CAT . . . TGG TGT

TTC CTA TGA TGA ATA TA-3'.

The sequence for the antisense strand of SEQ ID NO:9 was:

5'-TAT ATT CAT CAT AGG AAA CAC CA . . . A TGA TAT

TTT CTT TAA TGG TGC CA-3'.

SEQ ID NO:10 was a 50-mer mutant dsDNA target sequence identical to SEQ ID NO:5, except for a one base pair mutation (underlined), at which the sense strand sequence CAT was changed to C<u>T</u>T.

The sequence for the sense strand of mutant SEQ ID NO:10 was: 5'-GAG CAC CAT GAC AGA CAC TGT C<u>T</u>T CTC TGG TGT GTC CTA CGA TGA CTC TG-3'.

The sequence for the antisense strand of mutant SEQ ID NO:10 was: 5'-CAG AGT CAT CGT AGG ACA CAC CAG AGA <u>A</u>GA CAG TGT CTG TCA TGG TGC TC-3'.

SEQ ID NO:11 was a 50-mer mutant dsDNA target sequence identical to SEQ ID NO:5, except for a one base pair mutation (underlined), at which the sense strand sequence CTC was changed to C<u>C</u>C.

The sequence for the sense strand of mutant SEQ ID NO:11 was: 5'-GAG CAC CAT GAC AGA CAC TGT CAT C<u>C</u>C TGG TGT GTC CTA CGA TGA CTC TG-3'.

The sequence for the antisense strand of mutant SEQ ID NO:11 was: 5'-CAG AGT CAT CGT AGG ACA CAC CAG <u>G</u>GA TGA CAG TGT CTG TCA TGG TGC TC-3'.

The PNA probes were synthesized, HPLC purified and confirmed by mass spectroscopy by Commonwealth Biotechnologies, Inc. (Richmond, Va., USA). PNA probes were first dissolved in 0.1% TFA (trifluoroacetic acid) to a concentration of 10 mg/ml, and then diluted to 1 mg/ml by the addition of ddH$_2$O. Final PNA stock solutions were prepared in ddH$_2$O at a concentration of 1 pmole/µl.

Probe No. 1 was a 15-mer PNA probe designed to be completely complementary to a 15 nucleotide segment of the sense strand of the 50-mer wild-type target DNA (SEQ ID NO:1), overlapping amino acid positions 505 to 510 (Nature 380, 207 (1996)). The directionality of the probe was opposite or antiparallel to that of the sense strand in the target.

The sequence for Probe No. 1 (SEQ ID NO:12) was: 5'-H-CAC CAA AGA TGA TAT-Lys-CONH$_2$-3'.

Probe No. 2 was a 15-mer PNA probe identical in sequence to Probe No. 1, but was of the same directionality, or parallel to that of the sense strand in the dsDNA target.

The sequence for Probe No. 2 (SEQ ID NO:13) was: 5'-H-TAT AGT AGA AAC CAC-Lys-CONH$_2$-3'.

The 15-mer ssDNA probes were synthesized and purified by HPLC as above. SsDNA probes were dissolved in ddH$_2$O at a concentration of 1 pmole/µl.

Probe No. 3 was a 15-mer ssDNA probe designed to be completely complementary to a 15 nucleotide segment of the sense strand of the 50-mer wild-type target DNA (SEQ ID NO:5). The directionality of the probe was opposite or antiparallel to that of the sense strand in the target.

The sequence for Probe No. 3 (SEQ ID NO:14) was: 5'-CAC CAG AGA TCA CAG-3'.

Probe No. 4 was a 15-mer ssDNA probe identical in sequence to Probe No. 3, but was of the same directionality, or parallel to that of the sense strand in the dsDNA target.

The sequence for Probe No. 4 (SEQ ID NO:15) was: 5'-GAC AGT AGA GAC CAC-3'.

Probe No. 5 was a 15-mer antiparallel ssDNA probe identical to Probe No. 3, except it had an attached fluorescein moiety at the 5' position.

The sequence for Probe No. 5 (SEQ ID NO:16) was: 5'-Flu-CAC CAG AGA TGA CAG-3'.

Probe No. 6 was a 15-mer parallel ssDNA probe identical to Probe No. 4, except it had an attached fluorescein moiety at the 5' position.

The sequence for Probe No. 6 (SEQ ID NO:17) was: 5'-Flu-GAC AGT AGA GAC CAC-3'.

Probe No. 7 was a 15-mer ssDNA probe, with an attached fluorescein moiety at the 5' position, designed to be completely complementary to a 15 nucleotide segment of the sense strand of the 50-mer wild-type target DNA (SEQ ID NO:1). The directionality of the probe was opposite or antiparallel to that of the sense strand in the target.

The sequence for Probe No. 7 (SEQ ID NO:18) was: 5'-Flu-CAC CAA AGA TGA TAT-3'.

Probe No. 8 was a 15-mer ssDNA probe designed to be completely complementary to a 15 nucleotide segment of the sense strand of the 50-mer wild-type target DNA (SEQ ID NO:1). The directionality of the probe was antiparallel to that of the sense strand in the target.

The sequence for Probe No. 8 (SEQ ID NO:19) was: 5'-CAC CAA AGA TGA TAT-3'.

Probe No. 9 and Probe No. 10 were 15-mer mutant ssDNA probes identical in sequence to wild-type Probe No. 8, except for a one base mutation (underlined).

The sequence for Probe No. 9 (SEQ ID NO:20) was: 5'-CAC <u>G</u>AA AGA TGA TAT-3'.

The sequence for Probe No. 10 (SEQ ID NO:21) was: 5'-CAC CAA A<u>C</u>A TGA TAT-3'.

It is well known that ssDNA strands of mixed base sequence readily form ssPNA:ssDNA duplexes on a Watson-Crick pairing basis when reacted with either antiparallel or parallel synthesized ssPNA strands at room temperature. We have previously shown that such ssPNA:ssDNA complexes containing perfectly matched sequences can reliably be distinguished from ssPNA:ssDNA complexes containing a 1 bp mismatch when assayed in the presence of the DNA intercalator, YOYO-1 (Molecular Probes, Eugene, Oreg., USA), and that the order of assembly of the PNA strand has a significant bearing on its ability to specifically bind a ssDNA target. Example 1 compares the efficiency of formation of dsDNA duplexes when wild-type or mutant ssDNA target sequences are reacted with Watson-Crick complementary antiparallel ssDNA probes or with homologous, that is to say identical parallel, ssDNA probes.

The hybridization reaction mixtures giving rise to the data illustrated in FIG. 1A, each contained the following mixture: 2 pmoles of ssDNA target, 2 pmoles of ssDNA probe, 0.5×TBE and 500 nM of YOYO-1 in a final volume of 40 µl. The reaction mixtures were incubated at room temperature (21° C.) for 5 minutes, placed into a quartz cuvette, irradiated with an argon ion laser beam having a wavelength of 488 nm and monitored for fluorescent emission. The intensity of fluorescence was plotted as a function of wavelength for each sample analyzed.

In FIGS. 1B and 1C, the hybridization reaction mixtures (40 µl) each contained the following: 2 pmoles of ssDNA target, 2 pmoles of 5'-fluorescein labeled ssDNA probe, 10 mM Tris-HCl, pH 7.5, and 1 mM EDTA. The reaction mixtures were incubated at room temperature (21° C.) for 30 minutes or 90 minutes. Following incubation, each sample was placed into a quartz cuvette, irradiated with an argon ion laser beam having a wavelength of 488 nm and monitored for fluorescent emission. The maximum fluorescent intensities occurred at a wavelength of 525 nm, the emission wavelength for fluorescein. The intensity of fluorescent emission was plotted as a function of wavelength for each sample analyzed.

When the ssDNA Probe No. 3 was reacted with the 50-mer wild-type sense strand of SEQ ID NO:5 or with the 50-mer mutant sense strand of SEQ ID NO:7 in the presence of YOYO-1, antiparallel complementary ssDNA:ssDNA duplexes were formed (FIG. 1A). The fluorescent intensity emitted by the 1 bp T-G mismatched antiparallel complementary duplex (sense strand of SEQ ID NO:7+Probe No. 3) was 56% lower than that obtained by the perfectly matched antiparallel complementary duplex (sense strand of SEQ ID NO:5+Probe No. 3).

When the ssDNA Probe No. 3 was reacted with the 50-mer wild-type antisense strand of SEQ ID NO:5 in the presence of YOYO-1, the efficiency of parallel homologous ssDNA:ssDNA duplex formation was only 3% lower than the efficiency of antiparallel complementary ssDNA:ssDNA duplex formation (FIG. 1A). This result was completely unanticipated. The 1 bp A-G mismatched parallel homologous duplex formed when the 50-mer mutant antisense strand of SEQ ID NO:7 was reacted with the ssDNA Probe No. 3 in the presence of YOYO-1, produced a fluorescent emission intensity that was 56% lower than that emitted by the perfectly parallel homologous duplex (FIG. 1A). Control samples comprising each 50-mer ssDNA target plus 500 nM YOYO-1 exhibited levels of fluorescence which ranged from 91% to 92% lower than that observed with the perfectly matched duplexes (FIG. 1A). The level of fluorescence emitted by the 15-mer ssDNA Probe No. 3 plus 500 nM YOYO-1 was slightly greater than that produced by YOYO-1 alone. The shift in fluorescent emission wavelength observed with the ssDNA targets and probe is typical of YOYO-1's emission profile in the presence of ssDNA.

YOYO-1 facilitated DNA complex formation between a ssDNA probe and a complementary base sequence in an antiparallel ssDNA target, or between a ssDNA probe and an identical base sequence in a parallel ssDNA target, with similar efficacy, to allow differentiation between perfectly matched complexes and those containing a 1 bp mismatch. In the parallel homologous complexes, the 1 bp mismatch was a non-homologous base pair.

The comparative efficiency of antiparallel complementary and parallel homologous dsDNA duplex formation was further examined using ssDNA targets and ssDNA-F probes in the absence of complex promoting agents such as YOYO-1 or cations. When the ssDNA-F Probe No. 5 was incubated for 30 minutes in Tris buffer at room temperature with the 50-mer wild-type sense strand of SEQ ID NO:5, the Watson-Crick complementary antiparallel ssDNA:ssDNA-F duplexes were formed very efficiently, resulting in a 53% reduction in fluorescent emission compared to that emitted by Probe No. 5 alone (FIG. 1B). By contrast, antiparallel complementary ssDNA:ssDNA-F complexes that contained a 1 bp T-G mismatch (sense strand of SEQ ID NO:7+Probe No. 5) were less stable, resulting in only a 40% decrease in fluorescent emission compared to that emitted by Probe No. 5 alone after a 30 minute incubation (FIG. 1B).

Parallel homologous ssDNA:ssDNA-F complexes were formed when the ssDNA Probe No. 5 was reacted with the 50-mer wild-type antisense strand of SEQ ID NO:5 or with the 50-mer mutant antisense strand of SEQ ID NO:7, generating fluorescent emission intensities that were 44% and 37% lower, respectively, than that emitted by ssDNA Probe No. 5 alone after a 30 minute incubation (FIG. 1B). The avid formation of parallel homologous ssDNA:ssDNA-F complexes in the absence of a promoting agent was completely unanticipated. The discrimination between signals emitted from perfectly matched duplexes and 1 bp mismatched duplexes in the absence of complex promoting agents, was not as dramatic as that observed when YOYO-1 was present and served as the promoter and signaling agent (compare FIGS. 1A and 1B). This was the case for both antiparallel and parallel duplexes. Slightly less discrimination between perfectly matched and 1 bp mismatched DNA complexes was observed when a parallel homologous ssDNA target was used than when an antiparallel complementary ssDNA target was used to produce the ssDNA:ssDNA-F complexes (FIG. 1B).

After a 90 minute incubation, Watson-Crick antiparallel dsDNA:ssDNA-F complexes consisting of perfectly complementary sequences (sense strand of SEQ ID NO:5+Probe No. 5) or 1 bp T-G mismatched sequences (sense strand of SEQ ID NO:7+Probe No. 5) produced a 39% and 30% decrease, respectively, in fluorescent emission intensity compared to that emitted by Probe No. 5 alone (FIG. 1C). Remarkably, parallel homologous ssDNA:ssDNA-F complexes exhibited the same level of stability after 90 minutes of incubation as did the Watson-Crick antiparallel ssDNA:ssDNA-F complexes. The fluorescent intensities for a perfectly parallel homologous duplex (antisense strand of SEQ ID NO:5+Probe No. 5) and a 1 bp A-G mismatched parallel homologous duplex (antisense strand of SEQ ID NO:7+Probe No. 5) were 40% and 25% lower, respectively, than that emitted by ssDNA Probe No. 5 alone after a 90 minute incubation (FIG. 1C).

The mechanism of recognition and binding of the homologous bases in the parallel dsDNA duplexes is unknown at this time. Nevertheless, recognition and binding of parallel homologous ssDNA sequences occurred in a configuration which allowed the discrimination between perfectly matched ssDNA:ssDNA complexes and those containing a 1 bp or 2 bp mismatch. In these parallel homologous complexes, the 1 bp mismatch was a non-homologous base pair.

Example 2

In Example 1, the remarkable efficiency of parallel homologous ssDNA:ssDNA duplex formation was demonstrated both in the presence of a complex promoting agent such as YOYO-1 and in the absence of any complex promoting agent. The recognition and binding of the homologous bases in the parallel dsDNA duplexes was such as to allow easy discrimination between perfectly homologous base sequences and parallel homologous sequences that contained a 1 bp mismatch. These parallel homologous 1 bp mismatches were also clearly recognizable as mismatches based on Watson-Crick complementary recognition and binding rules. Example 2 examines the recognition and binding efficiency of parallel homologous dsDNA duplexes that contain A-T or G-C base pairings, to determine whether these Watson-Crick complementary pairings appear as mismatches in a parallel homologous binding reaction.

Each hybridization reaction mixture (40 µl) contained the following: 2 pmoles of ssDNA target, 2 pmoles of ssDNA probe, 0.5×TBE and 500 nM of YOYO-1. The reaction mixtures were incubated at room temperature (21° C.) for 5 minutes, placed into a quartz cuvette, irradiated with an argon ion laser beam having a wavelength of 488 nm and monitored for fluorescent emission. The intensity of fluorescence was plotted as a function of wavelength for each sample analyzed.

When the ssDNA Probe No. 3 (with a 53% GC content) was reacted with the 50-mer wild-type antisense strand of SEQ ID NO:5 or with the 50-mer mutant antisense strand of SEQ ID NO:10 in the presence of YOYO-1, parallel homologous ssDNA:ssDNA duplexes were formed (FIG. 2A). The fluorescent intensity emitted by the 1 bp A-T mismatched parallel homologous duplex (antisense strand of SEQ ID NO:10+Probe No. 3) was 72% lower than that obtained by the perfectly parallel homologous duplex (antisense strand of SEQ ID NO:5+Probe No. 3) (FIG. 2A). This dramatic decrease in fluorescent emission by the parallel homologous duplex containing a 1 bp A-T, strongly suggested that the Watson-Crick A-T binding was hindered by the spatial and/or charge configuration imposed on the A and T bases when part of parallel homologous strands attempting to achieve stable duplex. Control samples comprising each 50-mer ssDNA target plus 500 nM YOYO-1 exhibited levels of fluorescence which ranged from 96% to 97% lower than that observed with the perfectly matched duplexes (FIG. 2A). The level of fluorescence emitted by the 15-mer ssDNA Probe No. 3 plus 500 nM YOYO-1 was slightly greater than that produced by YOYO-1 alone. The shift in fluorescent emission wavelength observed with the ssDNA targets and probe is typical of YOYO-1's emission profile in the presence of ssDNA.

Parallel homologous ssDNA:ssDNA duplexes were also formed when the 50-mer wild-type antisense strand of SEQ ID NO:1 (with a 33% GC content) was reacted with the wild-type ssDNA Probe No. 8 or with the mutant ssDNA Probes No. 9 and 10, in the presence of YOYO-1 (FIG. 2B). The fluorescent intensities emitted by the 1 bp G-C mismatched parallel homologous duplex (antisense strand of SEQ ID NO:1+Probe No. 9) and the 1 bp C-G mismatched parallel homologous duplex (antisense strand of SEQ ID NO:1+Probe No. 10) were 67% and 66% lower, respectively, than that obtained by the perfectly parallel homologous duplex (antisense strand of SEQ ID NO:1+Probe No. 8) (FIG. 2B). The configuration of the interacting bases in the parallel homologous duplexes was unfavorable for Watson-Crick complementary G-C binding, resulting in a decrease in fluorescent emission indicative of a 1 bp mismatch. Control samples consisting of the 50-mer ssDNA target plus 500 nM YOYO-1 or each of the 15-mer ssDNA probes plus 500 nM YOYO-1 resulted in levels of fluorescence that were slightly greater than that produced by YOYO-1 alone (FIG. 2B).

Therefore, the interacting base pairs in parallel homologous dsDNA duplexes, formed in the presence of YOYO-1, adopt a configuration that is unfavorable for binding between Watson-Crick complementary base pairs, resulting in such duplexes appearing to contain 1 bp mismatches.

We are led to envisage how mismatches in binding sequences, whether occurring as part of a hairpin or multistrand complex can cause energetic and repeated motion as the base sequences try to achieve the stability of the ideal binding configuration under either binding motif. It is expected that binding strength of base pairs upstream or downstream of nucleation sites, metal ions and other factors will have a bearing on the attempts to achieve bonding.

Example 3

This example examines the efficiency of antiparallel homologous ssDNA:ssDNA duplex formation facilitated by YOYO-1 or by monovalent cations.

The hybridization reactions, giving rise to the data illustrated in FIG. 3A, each contained the following mixture: 2 pmoles of ssDNA target, 2 pmoles of ssDNA probe, 0.5× TBE and 500 nM of YOYO-1 in a final volume of 40 µl. The reaction mixtures were incubated at room temperature (21° C.) for 5 minutes, placed into a quartz cuvette, irradiated with an argon ion laser beam having a wavelength of 488 nm and monitored for fluorescent emission. The intensity of fluorescent emission was plotted as a function of wavelength for each sample analyzed.

In FIG. 3B, the hybridization reaction mixtures (40 µl) each contained the following: 2 pmoles of ssDNA target, 2 pmoles of 5'-fluorescein labeled ssDNA probe, 10 mM Tris-HCl, pH 7.5, and 50 mM NaCl. The reaction mixtures were incubated at room temperature (21° C.) for various lengths of time ranging from 1 minute to 60 minutes. Following incubation, samples were placed into a quartz cuvette, irradiated with an argon ion laser beam having a wavelength of 488 nm and monitored for fluorescent emission. The intensity of fluorescent emission was plotted as a function of wavelength for each sample analyzed.

Incubation of ssDNA Probe No. 4 with the 50-mer wild-type antisense strand of SEQ ID NO:5 in the presence of YOYO-1 resulted in antiparallel homologous ssDNA:ssDNA complex formation (FIG. 3A). Although the efficiency of antiparallel homologous complex formation was only 65% that of conventional antiparallel complementary dsDNA formation (compare FIGS. 1A and 3A), recognition and binding of antiparallel homologous ssDNA sequences did occur, facilitated by YOYO-1. This result was completely unanticipated. Furthermore, antiparallel homologous ssDNA:ssDNA complexes comprising wild-type sequences were clearly distinguished from those comprising 1 bp or 2 bp mismatches. The fluorescent intensities emitted by the 1 bp A-G mismatched DNA complex (antisense strand of SEQ ID NO:7+Probe No. 4), the 1 bp C-T mismatched DNA complex (antisense strand of SEQ ID NO:6+Probe No. 4), and the consecutive 2 bp mismatched DNA complex (antisense strand of SEQ ID NO:8+Probe No. 4) were 25%, 65% and 71% lower, respectively, than that obtained by the perfect antiparallel homologous complex (antisense strand of SEQ ID NO:5+Probe No. 4) (FIG. 3A). As the degree of homology between the probe and target decreased, the level of fluorescent emission decreased. Control samples comprising each 50-mer ssDNA target plus 500 nM YOYO-1 exhibited levels of fluorescence which ranged from 88% to 90% lower than that observed with the perfectly matched complexes (FIG. 3A). The level of fluorescence emitted by the 15-mer ssDNA Probe No. 4 plus 500 nM YOYO-1 was slightly greater than that produced by YOYO-1 alone.

Antiparallel homologous ssDNA:ssDNA complex formation was further examined using ssDNA targets and ssDNA-F probes both in the presence and absence of 50 mM NaCl. After 15 minutes of incubation of ssDNA-F Probe No. 6 with the 50-mer wild-type antisense strand of SEQ ID NO:5 in the presence of 50 mM NaCl, antiparallel homologous ssDNA:ssDNA-F complexes were formed, as indicated by the 34% decrease in fluorescence observed compared to that emitted by Probe No. 6 alone (FIG. 3B). The efficiency of antiparallel homologous complex formation was 62% that of antiparallel complementary complex formation following a 15 minute incubation (data not shown). By contrast, antiparallel homologous ssDNA:ssDNA-F complexes that contained a 1 bp A-G mismatch (antisense strand of SEQ ID NO:7+Probe No. 6), a 1 bp C-T mismatch (antisense strand of SEQ ID NO:6+Probe No. 6), a 1 bp A-T mismatch (antisense strand of SEQ ID NO:10+Probe No. 6), and a consecutive 2 bp mismatch (antisense strand of SEQ ID NO:8+Probe No. 6), produced a 24%, 26%, 23% and a 13% decrease in fluorescence, respectively, compared to that emitted by Probe No. 6 alone after a 15 minute incubation (FIG. 3B). The configuration of the interacting bases in the antiparallel homologous duplexes was apparently unfavorable for Watson-Crick complementary A-T binding, resulting in a change in fluorescent emission indicative of a 1 bp mismatch. Less antiparallel homologous complex formation occurred following a 30 minute incubation in the presence of 50 mM NaCl (data not shown). No complex formation was evident after 45 minutes of incubation. Similar rates of antiparallel homologous complex formation and stability were observed in Tris buffer without NaCl (data not shown).

Promoted by YOYO-1 or NaCl, recognition and binding of antiparallel homologous ssDNA sequences occurred in a configuration which allowed the discrimination between perfectly matched ssDNA:ssDNA complexes and those containing a 1 bp or 2 bp mismatch. The interaction of the base pairs in the antiparallel homologous duplex resulted in a conventional Watson-Crick A-T base pair being destabilizing as a mismatch.

Example 4

This example demonstrates the efficiency of parallel complementary ssDNA:ssDNA complex formation promoted by monovalent cations. The hybridization reaction mixtures (40 µl) each contained the following: 2 pmoles of ssDNA target, 2 pmoles of 5'-fluorescein labeled ssDNA probe, 10 mM Tris-HCl, pH 7.5, and 50 mM NaCl. The reaction mixtures were incubated at room temperature (21° C.) for various lengths of time ranging from 1 minute to 60 minutes. Following incubation, samples were placed into a quartz cuvette, irradiated with an argon ion laser beam having a wavelength of 488 nm and monitored for fluorescent emission. The intensity of fluorescent emission was plotted as a function of wavelength for each sample analyzed.

After a 15 minute incubation in the presence of 50 mM NaCl, ssDNA:ssDNA-F duplexes consisting of perfectly complementary sequences (sense strand of SEQ ID NO:5+ Probe No. 6) formed readily, resulting in a 41% decrease in fluorescent emission intensity compared to that emitted by Probe No. 6 alone (FIG. 4). This high efficiency of parallel complementary duplex formation was completely unexpected. By contrast, incompletely complementary ssDNA:ssDNA-F complexes containing a 1 bp T-G mismatch (sense strand of SEQ ID NO:7+Probe No. 6), a 1 bp G-T mismatch (sense strand of SEQ ID NO:6+Probe No. 6), a 1 bp T-T mismatch (sense strand of SEQ ID NO:10+Probe No. 6), and a consecutive 2 bp mismatch (sense strand of SEQ ID NO:8+Probe No. 6), generated an 18%, 20%, 10% and 16% decrease, respectively, in fluorescent emission intensity compared to that exhibited by Probe No. 6 alone (FIG. 4).

Once formed in the presence of 50 mM NaCl, the perfectly matched parallel complementary duplexes were very stable, resulting in a 40% and 47% decrease in fluorescent emission after 30 minutes and 45 minutes of incubation, respectively, compared to that emitted by Probe No. 6 alone (data not shown). The 1 bp and 2 bp mismatched parallel complementary complexes were much less stable after 30 minutes and 45 minutes of incubation in the presence of 50 mM NaCl (data not shown). The rate and efficiency of parallel complementary ssDNA:ssDNA-F formation was very similar to that of antiparallel complementary ssDNA:ssDNA-F formation during the first 45 minutes of incubation in the presence of 50 mM NaCl (data not shown). While antiparallel complementary complexes continued to form easily after 60 minutes of incubation in 50 mM NaCl, no parallel complementary complex formation was evident at this time (data not shown).

NaCl facilitated DNA complex formation between a ssDNA-F probe and an antiparallel complementary ssDNA target, or between a ssDNA-F probe and a parallel complementary ssDNA target, with similar efficacy, to allow differentiation between perfectly matched complexes and those containing a 1 bp or 2 bp mismatch.

Example 5

Examples 1 to 4 demonstrated alternate base recognition and binding motifs occurring between antiparallel or parallel ssDNA probes, and complementary or homologous ssDNA targets to generate ssDNA:ssDNA duplexes, other than the conventional antiparallel Watson-Crick complementary dsDNA complexes. This example will show that bases are capable of recognizing and interacting with both complementary and homologous bases at the same time.

Samples of two pmoles of ssDNA Probe No. 3 were heated at 95° C. for 10 minutes and allowed to cool to room temperature for 30 minutes in the presence of various concentrations of a free base, resulting in ssDNA probes containing conjugated bases. Duplicate samples of ssDNA Probe No. 3 were similarly denatured and cooled in the absence of added free bases to generate non-conjugated ssDNA probes. Two pmoles of these conjugated or non-conjugated ssDNA probes were then mixed with 2 pmoles of ssDNA target in the presence of 500 nM YOYO-1 and 0.5×TBE in a final reaction volume of 40 µl. The reaction mixtures were incubated at room temperature (21° C.) for 5 minutes, placed into a quartz cuvette, irradiated with an argon ion laser beam having a wavelength of 488 nm, and monitored for fluorescent emission. The intensity of fluorescence was plotted as a function of wavelength for each sample analyzed.

When the non-conjugated ssDNA Probe No. 3 was reacted with the 50-mer wild-type sense strand of SEQ ID NO:5 or with the 50-mer mutant sense strand of SEQ ID NO:7, in the presence of YOYO-1, antiparallel complementary ssDNA:ssDNA complexes were formed (FIG. 5A). The fluorescent intensity emitted by the 1 bp T-G mismatched antiparallel complementary duplex (sense strand of SEQ ID NO:7+Probe No. 3) was 45% lower than that obtained by the perfectly matched antiparallel complementary duplex (sense strand of SEQ ID NO:5+Probe No. 3). Control samples comprising each 50-mer ssDNA target plus 500 nM YOYO-1 exhibited levels of fluorescence which ranged from 92% to 93% lower than that observed with the perfectly matched duplexes (FIG. 5A). The level of fluorescence emitted by the 15-mer ssDNA Probe No. 3 plus 500 nM YOYO-1 was slightly greater than that produced by YOYO-1 alone.

When the ssDNA Probe No. 3 was reacted with the 50-mer wild-type antisense strand of SEQ ID NO:5 in the presence of YOYO-1, the efficiency of parallel homologous ssDNA:ssDNA duplex formation was 14% lower than the efficiency of antiparallel complementary ssDNA:ssDNA duplex formation (compare FIGS. 5A and 5B). The 1 bp A-G mismatched parallel homologous duplex formed when the 50-mer mutant antisense strand of SEQ ID NO:7 was reacted with the ssDNA Probe No. 3 in the presence of YOYO-1, produced a fluorescent emission intensity that was 47% lower than that emitted by the perfectly parallel homologous duplex (FIG. 5B).

The 15-mer ssDNA Probe No. 3 contains six adenine bases. Conjugation of 2 pmoles of ssDNA Probe No. 3 with 3 pmoles of free thymine could result in 25% of the complementary A or 100% of the homologous T within Probe No. 3 bound to the added thymine. Complementary A-T binding is energetically preferred. Reaction of 2 pmoles of ssDNA Probe No. 3 (conjugated with 3 pmoles of thymine) with 2 pmoles of the wild-type antisense strand of SEQ ID NO:5 in the presence of YOYO-1 resulted in dramatically enhanced parallel homologous ssDNA:ssDNA complex formation (FIG. 5B). Twenty-five percent conjugation of the ssDNA probe with 3 pmoles of thymine increased parallel homologous complex formation between the perfectly homologous sequences by 78%. This augmentation of parallel homologous complex formation can be linked to the ability of the adenines in Probe No. 3 to interact simultaneously with the conjugated complementary thymine bases, as well as with the homologous adenines in the ssDNA target. Moreover, interaction with available complementary bases was not deleterious to the homologous binding configuration adopted by the homologous bases and their neighbors.

By contrast, the efficiency of formation of parallel homologous complexes containing a 1 bp A-G mismatch (antisense strand of SEQ ID NO:7+Probe No. 3) were increased by 16% when Probe No. 3 was conjugated 25% with thymine than when non-conjugated Probe No. 3 was used (FIG. 5B). This corresponded to a 65% reduction in fluorescent emission intensity for the 1 bp A-G mismatched parallel homologous complex compared to that observed for the perfectly matched parallel homologous complex when the T-conjugated Probe No. 3 was used. Conjugation of the ssDNA probe increased the specificity in discriminating between perfectly matched parallel homologous complexes and 1 bp mismatched parallel homologous complexes.

Remarkably, perfectly matched antiparallel complementary ssDNA:ssDNA complex formation was enhanced by 48% when Probe No. 3 conjugated 25% with thymine was reacted with the sense strand of SEQ ID NO:5 in the presence of YOYO-1 (FIG. 5A). The simultaneous interaction of an adenine in Probe No. 3 with the conjugated complementary thymine and the complementary T in the ssDNA target augmented formation of the perfectly matched antiparallel complementary complex. Remarkably, formation of the 1 bp T-G mismatched antiparallel complementary complex was very inefficient when T-conjugated Probe No. 3 was used, resulting in an 88% decrease in fluorescent emission intensity compared to that generated by the perfectly matched antiparallel complementary complex containing conjugated T (FIG. 5A). It is also remarkable that discrimination between perfectly matched and 1 bp mismatched antiparallel complementary ssDNA:ssDNA complexes was greatly enhanced by use of conjugated ssDNA probes in the presence of YOYO-1.

Twenty-five percent conjugation of Probe No. 3 with cytosine or guanosine also increased the efficiency of both antiparallel complementary and parallel homologous ssDNA:ssDNA complex formation in the presence of YOYO-1, as well as improved the specificity in differentiation between perfectly matched complexes and 1 bp mismatched complexes (data not shown).

Formation of ssDNA:ssDNA complexes comprising conjugated bases proves that the bases in a sequence can recognize and interact specifically and simultaneously with both complementary and homologous bases provided the conjugated base is a Watson-Crick complement to a base on the strand which binds specifically to another strand. The recognition and binding configurations between bases in a ssDNA probe, conjugated bases and bases in a ssDNA target may be similar to the base configurations formed in antiparallel and parallel dsDNA:ssDNA complexes described herein.

Example 6

Example 6 demonstrates quadruplex DNA formation between dsDNA targets containing mixed base sequences and homologous dsDNA probes labeled with fluorescein. Quadruplex DNA formation is enhanced by the presence of monovalent cations added to the reaction. Complementary sense and antisense 15-mer ssDNA sequences were synthesized, purified by HPLC and annealed as above to generate 15-mer dsDNA probes. DsDNA probes were diluted in ddH$_2$O at a concentration of 1 pmole/µl.

Probe No. 11 was a 15-mer dsDNA probe with an attached fluorescein moiety at each 5' position, and was designed to be completely homologous to a central 15 bp segment of the 50-mer wild-type target DNA (SEQ ID NO:5).

The sequence for the sense strand of Probe No. 11 (SEQ ID NO:22) was: 5'-Flu-CTG TCA TCT CTG GTG-3'.

The sequence for the antisense strand of Probe No. 11 (SEQ ID NO:22) was: 5'-Flu-CAC CAG AGA TGA CAG-3'.

Each hybridization reaction mixture (40 µl) contained the following: 0.4 pmoles of target dsDNA, 4 pmoles of 5'-fluorescein labeled dsDNA Probe No. 11, 10 mM Tris-HCl, pH 7.5 and 100 mM KCl. The reaction mixtures were incubated at room temperature (21° C.) for 1 hour, without prior denaturation. Samples were placed into a quartz cuvette, irradiated with an argon ion laser beam having a wavelength of 488 nm and monitored for fluorescent emission. The maximum fluorescent intensities occurred at a wavelength of 525 nm, the emission wavelength for fluorescein. FIG. 6 shows the intensity of fluorescence plotted as a function of wavelength for each sample analyzed.

In the absence of KCl, no binding between the dsDNA targets and Probe No. 11 was detected, resulting in similar fluorescent intensities observed when wild-type dsDNA target (SEQ ID NO:5) or mutant dsDNA target (SEQ ID NO:7) were mixed with dsDNA Probe No. 11 or when dsDNA Probe No. 11 was present alone (data not shown).

After a 1 hour incubation at 21° C. in the presence of 100 mM KCl, dsDNA:dsDNA-F quadruplexes consisting of perfectly homologous sequences on dsDNA target (SEQ ID NO:5) and dsDNA Probe No. 11 formed readily, resulting in a 62% decrease in the intensity of fluorescent emission compared to that emitted by dsDNA Probe No. 11 alone (labeled dsDNA-F) (FIG. 6). In contrast, incompletely homologous dsDNA:dsDNA-F quadruplexes (SEQ ID NO:7+Probe No. 11), containing a 1 base pair mismatch were less stable in these reaction conditions, yielding only an 18% decrease in fluorescent intensity compared to that exhibited by dsDNA Probe No. 11 alone.

The presence of monovalent cations, such as $K^+$, at specific concentrations was sufficient to allow quadruplex formation between dsDNA targets and dsDNA probes labeled with fluorescein in the absence of prior denaturation. Quadruplex formation occurred on the basis of homologous base pair affinities, with a measurable and significantly greater amount of quadruplex formation between fully homologous duplex strands. Moreover, the reaction occurred at room temperature within just 1 hour of incubation at a ratio of probe to target of 10 to 1, using natural dsDNA. The dsDNA targets and dsDNA probe used in this example were homologous, contained 53% GC content, and did not contain homopurine or homopyrimidine stretches on any DNA strand. The assay of the invention was able to identify perfectly homologous dsDNA sequences and those containing a pair of mismatched bases, using a dsDNA probe.

Example 7

The quadruplex DNA assays performed in Example 6 were facilitated by the addition of monovalent cations in the reaction mixtures. The specificity of the assay was further examined utilizing divalent cations to facilitate quadruplex DNA formation with dsDNA targets and dsDNA-F probes possessing 53% GC content.

Each hybridization reaction mixture (40 µl) contained the following: 0.4 pmoles of target dsDNA, 4 pmoles of 5'-fluorescein labeled dsDNA Probe No. 11, 10 mM Tris-HCl, pH 7.5, 20 mM $MnCl_2$ and 20 mM $MgCl_2$. The reaction mixtures were incubated at room temperature (21° C.) for 1 hour, without prior denaturation. Samples were placed into a quartz cuvette, irradiated with an argon ion laser beam having a wavelength of 488 nm and monitored for fluorescent emission. FIG. 7 shows the intensity of fluorescence plotted as a function of wavelength for each sample analyzed.

When dsDNA-F Probe No. 11 (with a 53% GC content) was incubated with the 50-mer wild-type dsDNA target (SEQ ID NO:5) or the mutant dsDNA target (SEQ ID NO:7) in the presence of 20 mM $MnCl_2$ and 20 mM $MgCl_2$, quadruplexes were formed at room temperature under nondenaturing conditions. While perfectly homologous DNA quadruplexes yielded the maximum decrease in fluorescent intensity, a 34% decrease, the less favourable dsDNA: dsDNA-F quadruplexes containing a 1 bp mismatch (SEQ ID NO:7+Probe No. 11) produced a fluorescent intensity that was about the same as that observed with dsDNA Probe No. 11 alone (FIG. 7).

The presence of divalent cations such as $Mn^{+2}$ and $Mg^{+2}$ facilitated quadruplex formation under non-denaturing conditions to allow accurate discrimination between fully homologous dsDNA target and dsDNA probe quadruplexes, and quadruplex sequences containing a pair of bases which are mismatched.

Example 8

The quadruplex DNA assays performed in Examples 6 and 7 were facilitated by the addition of either monovalent cations or divalent cations in the reaction mixtures. The next Example demonstrates the specificity of the homologous quadruplex DNA assay when the DNA intercalator, YOYO-1, is employed.

Complementary sense and antisense 15-mer ssDNA sequences were synthesized, purified by HPLC and annealed as above to generate 15-mer dsDNA probes. DsDNA probes were diluted in $ddH_2O$ at a concentration of 1 pmole/µl.

Probe No. 12 was a 15-mer dsDNA probe identical in sequence to Probe No. 11, but without the attached 5' fluorescein moieties.

The sequence for the sense strand of Probe No. 12 (SEQ ID NO:23) was: 5'-CTG TCA TCT CTG GTG-3'.

The sequence for the antisense strand of Probe No. 12 (SEQ ID NO:23) was: 5'-CAC CAG AGA TGA CAG-3'.

Each hybridization reaction mixture (40 µl) contained the following: 0.4 pmoles of dsDNA target, 4 pmoles of dsDNA Probe No. 12, 0.5×TBE and 100 nM of YOYO-1. The reaction mixtures were incubated at 21° C. for 5 minutes, placed into a quartz cuvette, irradiated with an argon ion laser beam having a wavelength of 488 nm and monitored for fluorescent emission. The intensity of fluorescent emission was plotted as a function of wavelength for each sample analyzed.

The fluorescent intensities observed when no target or probe was present (YOYO-1 only) are shown in FIG. 8. FIG. 8 also shows the fluorescent intensities observed when the reaction mixtures combined dsDNA Probe No. 12 with wild-type 50-mer dsDNA target (SEQ ID NO:5) which contained homologous sequences, or with four other dsDNA targets which, but for one mismatched pair of bases, contained sequences which were homologous to the base sequences in the dsDNA Probe No. 12. Homologous wild-type dsDNA target (SEQ ID NO:5) when present in the reaction mixture with the dsDNA Probe No. 12 produced the greatest fluorescent intensity. Mismatched dsDNA targets when incubated with dsDNA Probe No. 12 in the reaction mixture yielded lesser fluorescent intensity values ranging from 20% less for dsDNA target (SEQ ID NO:10) to 80% less for dsDNA target (SEQ ID NO:11), compared to that achieved by perfectly matched quadruplexes (FIG. 8).

It was observed that homologous quadruplexes, stabilized by YOYO-1 intercalation, formed more readily between a dsDNA target and a dsDNA probe when that probe contained perfectly homologous sequences, than when there was a single pair of bases which were not homologous, that is to say identical, to a pair of bases in the dsDNA target. The quadruplex complexes described in the foregoing three examples are referred to by us as mirror homologous.

Example 9

In this example, 50-mer dsDNA targets were exposed to a 53% GC 15-mer dsDNA probe (Probe No. 13), wherein Watson-Crick complementarity exists between bases of the strands of the probe and proximal bases of the strands of the target when the major groove of one duplex is placed in the minor groove of the other duplex. The sequences of bases in the duplex probe are not homologous but are inverted in relation to those in the duplex target. The duplexes, when nested major groove into minor groove, are parallel to one another, and referred to by us as nested complementary.

Complementary sense and antisense 15-mer ssDNA sequences were synthesized, purified by HPLC and annealed as above to generate 15-mer dsDNA probes. DsDNA probes were diluted in ddH$_2$O at a concentration of 1 pmole/µl.

The sequence for the sense strand of Probe No. 13 (SEQ ID NO:24) was: 5'-GAC AGT AGA GAC CAC-3'.

The sequence for the antisense strand of Probe No. 13 (SEQ ID NO:24) was: 5'-GTG GTC TCT ACT GTC-3'.

Each hybridization reaction mixture (40 µl) contained the following: 0.4 pmoles of target dsDNA, 4 pmoles of dsDNA Probe No. 13, 0.5×TBE and 100 nM of YOYO-1. The reaction mixtures were incubated at room temperature (21° C.) for 5 minutes, placed in a quartz cuvette, irradiated with an argon ion laser beam having a wavelength of 488 nm and monitored for fluorescent emission. The intensity of fluorescent emission was plotted as a function of wavelength for each sample analyzed.

FIG. 9 illustrates that in the absence of prior denaturation, the highest fluorescent intensities were achieved when the wild-type 50-mer dsDNA target (SEQ ID NO:5) was reacted with the 15-mer dsDNA Probe No. 13, which was a perfect match on a nested complementary basis to the dsDNA target (SEQ ID NO:5). The fluorescent intensity is indicative of DNA binding taking place, in this case quadruplex formation between the dsDNA target and the nested complementary dsDNA probe.

Mutant dsDNA targets which were mismatched with the duplex probe by a single pair of bases when matching was assessed on the inverted homology basis of nested complementarity, formed measurably fewer quadruplex complexes with the dsDNA probe, than did the fully complementary wild-type dsDNA target. The various mismatches, which were assayed on a mirror homologous basis in Example 8 were assayed on a nested complementary basis in this example.

As shown in FIG. 9, the fluorescent intensities produced by the quadruplexes formed with the 1 bp mismatched dsDNA targets plus dsDNA Probe No. 13, ranged from 8% to 16% less than that achieved by perfectly matched quadruplexes (SEQ ID NO:5+Probe No. 13).

Greater discrimination in fluorescence was observed between perfectly homologous and partially homologous quadruplexes in Example 8. This suggests that fully complementary or 1 base pair mismatched nested complementary dsDNA probes bind less discriminately to dsDNA targets than do mirror homologous dsDNA probes, which bind with greater specificity.

This example shows that Watson-Crick quadruplex binding between nested complementary DNA duplexes readily occurs in the presence of YOYO-1.

Example 10

Example 10 demonstrates that the assay of the invention can discriminate between perfectly matched, Watson-Crick complementary dsDNA:ssPNA complexes and dsDNA:ssPNA complexes containing 1 bp, 2 bp and 3 bp mismatches when a cationic decondensing agent, such as the DNA intercalator, YOYO-1 is present.

Each hybridization reaction mixture (40 µl) contained the following: 2 pmoles of target dsDNA, 2 pmoles of ssPNA probe, 0.5×TBE and 500 nM of YOYO-1. The reaction mixtures were incubated at room temperature (21° C.) for 5 minutes, placed into a quartz cuvette, irradiated with an argon ion laser beam having a wavelength of 488 nm and monitored for fluorescent emission. The intensity of fluorescence was plotted as a function of wavelength for each sample analyzed.

The fluorescent intensities observed when no DNA or PNA was present (YOYO-1 only), or when wild-type SEQ ID NO:1, mutant SEQ ID NO:2 or mutant SEQ ID NO:3 were reacted with antiparallel PNA Probe No. 1 or parallel PNA Probe No. 2 are shown in FIGS. 10A and 10B, respectively. DsDNA:ssPNA complexes consisting of perfectly complementary sequences (SEQ ID NO:1+Probe No. 1) allowed maximum interaction between YOYO-1 and the complexes, yielding the highest fluorescent intensities (FIG. 10A). The fluorescent intensities for a one base pair mismatched dsDNA:ssPNA complex (SEQ ID NO:2+Probe No. 1) and a two base pair mismatched dsDNA:ssPNA complex (SEQ ID NO:3+Probe No. 1) was 97% and 99% lower, respectively, than the perfectly matched dsDNA:ssPNA complex (FIG. 10A). Similarly, when parallel PNA Probe No. 2 was bound to the target dsDNA sequences, the one and two base pair mismatched dsDNA:ssPNA complexes exhibited fluorescent intensities that were 92% and 97% lower, respectively, than the perfectly complementary dsDNA:ssPNA complexes (SEQ ID NO:1+Probe No. 2) (FIG. 10B). Three base pair mismatched dsDNA:ssPNA complexes consisting of SEQ ID NO:4 and Probe No. 1, or SEQ ID NO:4 and Probe No. 2 produced fluorescent intensities that were 99% and 97% lower, respectively, than the perfectly matched dsDNA:ssPNA complexes (data not shown). Control samples comprising 50-mer dsDNA targets plus 500 nM YOYO-1 exhibited levels of fluorescence which were at or below the level of fluorescence observed with 3 bp mismatched complexes (data not shown). The level of fluorescence emitted by either ssPNA probe plus 500 nM YOYO-1 together was identical to that emitted by YOYO-1 alone (data not shown). As the degree of mismatch between the probe and the target increased, the level of interaction of YOYO-1 with the mismatched complexes diminished. Hence the intensity of fluorescent emission decreased. This relationship held whether or not an antiparallel or parallel PNA probe was used. The characteristic level of fluorescence emitted by each complex was monitored over time and was stable between 5 minutes and 24 hours.

Interestingly, when 15-mer target dsDNA sequences were reacted with 15-mer PNA probe sequences, larger differences in fluorescent emission were observed between perfectly matched complexes and 1 or 2 bp mismatched complexes when parallel PNA probes were used, than when antiparallel PNA probes were used (data not shown).

Therefore, the fluorescent intensity assay measuring dsDNA:ssPNA complex formation is able to distinguish between wild-type sequences and those containing 1 bp, 2 bp or 3 bp mutations, without prior denaturation of the duplex DNA target.

Example 11

The specificity of the assay measuring triplex formation promoted by YOYO-1 was further investigated by reacting wild-type and mutant dsDNA targets of mixed base sequence with antiparallel and parallel ssDNA probes in the absence of prior denaturation of dsDNA targets.

Each hybridization reaction mixture (40 µl) contained the following: 2 pmoles of target dsDNA, 2 pmoles of ssDNA probe, 0.5×TBE and 500 nM of YOYO-1. The reaction mixtures were incubated at room temperature (21° C.) for 5 minutes, placed into a quartz cuvette, irradiated with an argon ion laser beam having a wavelength of 488 nm and monitored for fluorescent emission. The intensity of fluorescence was plotted as a function of wavelength for each sample analyzed.

When the antiparallel ssDNA Probe No. 3 (with a 53% GC content) was reacted with the 50-mer wild-type dsDNA target (SEQ ID NO:5) and mutant dsDNA targets (SEQ ID NO:6 and SEQ ID NO:8), dsDNA:ssDNA complexes were formed at room temperature under non-denaturing conditions (FIG. 11A). While perfectly matched DNA complexes emitted the highest fluorescent intensities, incompletely complementary complexes with a 1 bp mismatch (SEQ ID NO:6+Probe No. 3) and a consecutive 2 bp mismatch (SEQ ID NO:8+Probe No. 3) produced fluorescent intensities that were 63% and 95% lower, respectively, than that observed with the perfectly matched sequences (FIG. 11A). The level of fluorescence diminished as the degree of mismatch between the probe and target increased. The characteristic fluorescent intensity exhibited by each complex was monitored over time and was stable between 5 minutes and 24 hours. Control samples comprising 50-mer dsDNA targets plus 500 nM YOYO-1 exhibited levels of fluorescence which were below the level of fluorescence observed with 2 bp mismatched DNA complexes (data not shown). The level of fluorescence generated by the ssDNA probe plus 500 nM YOYO-1 was identical to that achieved by YOYO-1 alone (data not shown). Very similar results were obtained when 15-mer antiparallel ssDNA probes were reacted with wild-type or mutant 50-mer dsDNA targets having 33% GC and 73% GC contents under the same reaction conditions, demonstrating the reliability of the dsDNA:ssDNA complex formation assay utilizing antiparallel ssDNA probes, independent of the percent GC content of the ssDNA probes and dsDNA targets (data not shown).

Similarly, in the presence of YOYO-1, dsDNA:ssDNA complexes were formed when the parallel ssDNA Probe No. 4 was reacted with the 50-mer wild-type dsDNA target (SEQ ID NO:5) and mutant dsDNA targets (SEQ ID NO:6 and SEQ ID NO:8). The fluorescent intensities for a 1 bp mismatched DNA complex (SEQ ID NO:6+Probe No. 4) and a consecutive 2 bp mismatched DNA complex (SEQ ID NO:8+Probe No. 4) were 48% and 65% lower, respectively, than that obtained by the perfectly matched sequences (FIG. 11B). As the degree of mismatch between the probe and target increased, the level of fluorescent emission decreased. Slightly less discrimination between perfectly matched and mismatched DNA complexes was observed when a parallel ssDNA probe was used than when an antiparallel ssDNA probe was used to generate the dsDNA:ssDNA complexes.

YOYO-1 facilitated DNA complex formation between an antiparallel ssDNA probe and dsDNA targets, and between a parallel ssDNA probe and dsDNA targets, to allow differentiation between perfectly matched complexes and those containing 1 bp or 2 bp mismatches, without the requirement for prior denaturation of dsDNA targets.

Example 12

The complexes formed in Examples 10 and 11 were stabilized by the DNA intercalator, YOYO-1 present in the reaction mixtures. The specificity of the assay was further examined utilizing divalent cations to promote and stabilize complex formation with dsDNA targets and ssDNA-F probes.

Each hybridization reaction mixture (40 μl) contained the following: 0.4 pmoles of target dsDNA, 4 pmoles of 5'-fluorescein labeled ssDNA probe, 10 mM Tris-HCl, pH 7.5, and 1 mM to 20 mM each of $MgCl_2$ and $MnCl_2$. The reaction mixtures were incubated at room temperature (21° C.) for various lengths of time ranging from 1 minute to 2 hours, without prior denaturation of dsDNA targets. Following incubation, samples were placed into a quartz cuvette, irradiated with an argon ion laser beam having a wavelength of 488 nm and monitored for fluorescent emission. The maximum fluorescent intensities occurred at a wavelength of 525 nm, the emission wavelength for fluorescein. The intensity of fluorescent emission was plotted as a function of wavelength for each sample analyzed.

When the antiparallel ssDNA-F Probe No. 5 was incubated for 1 hour with the 50-mer wild-type dsDNA target (SEQ ID NO:5) in the presence of 15 mM $MgCl_2$ and 15 mM $MnCl_2$, perfectly complementary dsDNA:ssDNA-F complexes were formed very efficiently, generating a 74% decrease in fluorescence compared to that achieved by Probe No. 5 alone (FIG. 12A). By contrast, dsDNA:ssDNA-F complexes that contained a 1 bp T-G mismatch (SEQ ID NO:7+Probe No. 5) were much less stable in the presence of 15 mM $MgCl_2$ and 15 mM $MnCl_2$, yielding a 15% decrease in fluorescence compared to that emitted by Probe No. 5 alone after a 1 hour incubation (FIG. 12A). When Probe No. 5 (containing a 53% GC content) was reacted with the dsDNA target SEQ ID NO:9 (containing a 33% GC content), a 3% increase in fluorescence was observed compared to that obtained by Probe No. 5 alone (FIG. 12A), indicative of no DNA complex formation. This result was expected considering this probe and target combination would result in a 5 bp mismatch.

In the presence of 10 mM $MgCl_2$ and 10 mM $MnCl_2$, the dsDNA:ssDNA-F complexes possessing a 53% GC content and containing perfectly complementary sequences (SEQ ID NO:5+Probe No. 5) or a 1 bp T-G mismatch (SEQ ID NO:7+Probe No. 5) generated fluorescent intensities that were 68% and 20% lower, respectively, after an 1 hour incubation, and 76% and 16% lower, respectively, after a 30 minute incubation, than that emitted by Probe No. 5 alone (data not shown). The addition of 5 mM $MgCl_2$ and 5 mM $MnCl_2$ (or lower concentrations) was insufficient to allow complex formation between the antiparallel ssDNA-F Probe No. 5 and all dsDNA targets tested following a 1 hour incubation (data not shown).

DsDNA:ssDNA complexes were also formed when the parallel ssDNA Probe No. 6 was reacted with the 50-mer wild-type dsDNA target (SEQ ID NO:5) and mutant dsDNA target (SEQ ID NO:7). In this case DNA complex formation was promoted with much lower concentrations of $MgCl_2$ and $MnCl_2$ (i.e. 1-5 mM each) requiring shorter incubation periods. Incubation in the presence of 1 mM $MgCl_2$ and 1 mM $MnCl_2$, or 2 mM $MgCl_2$ and 2 mM $MnCl_2$ for 15 minutes was sufficient to generate DNA complexes (data not shown). The fluorescent intensities for a perfectly matched DNA complex (SEQ ID NO:5+Probe No. 6) and a 1 bp mismatched DNA complex (SEQ ID NO:7+Probe No. 6) were 29% and 6% lower, respectively, than that obtained by parallel ssDNA Probe No. 6 alone in the presence of 3 mM $MgCl_2$ and 3 mM $MnCl_2$ after a 45 minute incubation (FIG. 12B).

Although DNA complexes formed readily at 10 mM $MgCl_2$ and 10 mM $MnCl_2$ after a 1 hour incubation, no discrimination between perfectly matched and mismatched complexes was observed when a parallel ssDNA probe was used. Concentrations above 15 mM $MgCl_2$ and 15 mM $MnCl_2$ were inhibitory for DNA complex formation with a parallel ssDNA probe (data not shown).

The addition of salt bridging, condensing agents such as divalent cations promoted DNA complex formation between non-denatured dsDNA targets and fluorescently-labeled antiparallel or parallel ssDNA probes, to allow accurate and reliable discrimination between perfectly complementary sequences and those containing 1 bp mutations. The reactions occurred at room temperature within 15-60 minutes of incubation at a ratio of probe to target of 10 to 1. The dsDNA targets and ssDNA probes did not contain homopurine or homopyrimidine stretches of DNA. Despite the presence of 5 pyrimidine bases interspersed within the 15 nucleotide ssDNA probes, DNA complexes formed readily in a sequence specific manner.

Example 13

The utility of probes of varying directionality was also evaluated when monovalent cations were employed to promote and stabilize complex formation with dsDNA targets.

Each hybridization reaction mixture (40 µl) contained the following: 0.4 pmoles of target dsDNA, 4 pmoles of 5'-fluorescein labeled ssDNA probe, 10 mM Tris-HCl, pH 7.5, and 10 mM to 150 mM NaCl. The reaction mixtures were incubated at room temperature (21° C.) for various lengths of time ranging from 1 minute to 2 hours, without prior denaturation of dsDNA targets. Following incubation, samples were placed into a quartz cuvette, irradiated with an argon ion laser beam having a wavelength of 488 nm and monitored for fluorescent emission. The maximum fluorescent intensities occurred at a wavelength of 525 nm, the emission wavelength for fluorescein. The intensity of fluorescent emission was plotted as a function of wavelength for each sample analyzed.

In the absence of NaCl or presence of 10 mM or 25 mM NaCl, no binding between the dsDNA targets (SEQ ID NO:1 or SEQ ID NO:2) and the antiparallel ssDNA-F Probe No. 7 was detected, after all incubation periods (data not shown).

After a 1 hour incubation in the presence of 50 mM NaCl, dsDNA:ssDNA-F complexes consisting of perfectly complementary sequences (SEQ ID NO:1+°Probe No. 7) formed readily, resulting in a 49% decrease in fluorescent emission intensity compared to that emitted by the control Probe No. 7, which was similarly incubated in the reaction mixture (FIG. 13A). By contrast, incompletely complementary dsDNA:ssDNA-F complexes containing a 1 bp G-T mismatch (SEQ ID NO:2+Probe No. 7) yielded a 11% decrease in fluorescent emission intensity compared to that exhibited by the Probe No. 7 control sample.

The presence of 75 mM, 100 mM and 125 mM NaCl in the reaction mixture also resulted in fluorescent emission quenching consistent with significant amounts of complex formation between the perfectly matched SEQ ID NO:1 target and antiparallel Probe No. 7, and significantly less quenching when the 1 bp G-T mismatched SEQ ID NO:2 target and Probe No. 7 were present, producing similar fluorescent intensities to that observed in the presence of 50 mM NaCl (data not shown).

DsDNA:ssDNA complexes were also formed when the parallel ssDNA Probe No. 6 was reacted with the 50-mer wild-type dsDNA target (SEQ ID NO:5) and mutant dsDNA target (SEQ ID NO:7) in the presence of 50 mM, 75 mM, 100 mM or 150 mM NaCl. Optimum results were obtained in the presence of 100 mM NaCl. After a 75 minute incubation at room temperature in a reaction mixture containing 100 mM NaCl, the fluorescent emission intensities for a perfectly matched DNA complex (SEQ ID NO:5+Probe No. 6) and a 1 bp mismatched DNA complex (SEQ ID NO:7+Probe No. 6) were 53% and 9% lower, respectively, than that obtained by the control parallel ssDNA Probe No. 6 reacted under the same conditions (FIG. 13B). 50 mM NaCl promoted maximum discrimination between perfectly matched and mismatched complexes in an incubation period of 45 minutes (data not shown). In general, complexes containing either antiparallel or parallel ssDNA probes seemed to form with similar efficiencies at similar NaCl concentrations and incubation periods.

Use of monovalent cations, which are known DNA condensing agents, facilitated DNA complex formation between non-denatured dsDNA targets and fluorescently-labeled antiparallel or parallel ssDNA probes, to allow reliable differentiation between complexes containing perfectly complementary sequences and those containing 1 bp mismatches.

Example 14

DsDNA:ssDNA complexes facilitated by YOYO-1 readily form at room temperature within 5 minutes of incubation and generate fluorescent emissions at the same level of intensity for hours. Complexes containing base pair mismatches similarly emit fluorescent signals which persist, indicating the same level of complex formation over time. To examine the rate of formation, stability and rate of disassociation of dsDNA:ssDNA complexes formed in the presence of condensing agents such as cations, time course experiments were performed.

Each hybridization reaction mixture (40 µl) contained the following: 0.4 pmoles of non-denatured target dsDNA, 4 pmoles of 5'-fluorescein labeled ssDNA probe, 10 mM Tris-HCl, pH 7.5, 10 mM $MgCl_2$ and 10 mM $MnCl_2$. The reaction mixtures were incubated at room temperature (21° C.) for various periods ranging from 1 minute to 2 hours. Following incubation, samples were placed into a quartz cuvette, irradiated once with an argon ion laser beam having a wavelength of 488 nm and monitored for fluorescent emission. Further fluorescent measurements were taken of the same samples after subsequent multiple laser irradiation, at the indicated times (FIG. 14). The intensity of fluorescence was plotted as a function of time for each sample analyzed.

The fluorescence emitted by control samples comprising 4 pmoles of Probe No. 5 plus 10 mM $MgCl_2$ and 10 mM $MnCl_2$, in the absence of target dsDNA, dramatically decreased 3-fold within just 5 minutes of incubation (data not shown), and then steadily declined at a much slower rate within the next few hours (FIG. 14A). This effect we refer to as "Cationic Quench". This inhibition of fluorescence, associated with increased incubation periods of ssDNA-F probes with specific cations, occurred routinely in the presence of divalent cations, but not in the presence of monovalent cations (data not shown). This observation makes evident the importance of incubating the control sample in an experiment under exactly the same conditions that the test samples of an experiment are reacted. Multiple lasing of each ssDNA-F control sample after varying periods of incubation inhibited further quenching of the fluorophore, resulting in a steady level of fluorescence thereafter (FIG. 14A). This result was entirely unanticipated.

When the antiparallel ssDNA-F Probe No. 5 was incubated with the 50-mer wild-type dsDNA target (SEQ ID NO:5) in the presence of 10 mM $MgCl_2$ and 10 mM $MnCl_2$, dsDNA:ssDNA-F complex formation was evident after 15 minutes of incubation resulting in a decrease in fluorescence, which was 6% greater than the progressive cationic quench of the control Probe No. 5 (compare FIGS. 14A and 14B). Complex formation was greatly indicated after 30 and 60 minutes of incubation of SEQ ID NO:5 with Probe No. 5 in the presence of 10 mM $MgCl_2$ and 10 mM $MnCl_2$, generating a 76% and 61% decrease in fluorescence, respectively, compared to that achieved by the cationically quenched Probe No. 5 alone (FIG. 14B). After 90 and 120 minutes of incubation in the presence of 10 mM $MgCl_2$ and 10 mM $MnCl_2$, no complex formation was being signaled (FIG. 14B) The level of fluorescent emission seen at 90 and 120 minutes was wholly attributable to the cationic quench effect (compare FIGS. 14A and 14B).

By contrast, dsDNA:ssDNA-F complexes that contained a 1 bp T-G mismatch (SEQ ID NO:7+Probe No. 5) formed at a slower rate and were much less stable once formed in the presence of 10 mM $MgCl_2$ and 10 mM $MnCl_2$. The 1 bp T-G mismatched complex was first observed after 30 minutes of incubation, and appeared to have been eliminated after 60 minutes of incubation (FIG. 14C). Once again, the probe was antiparallel to the complementary strand in the duplex (FIG. 14C).

Multiple laser irradiation of perfectly complementary dsDNA:ssDNA complexes (SEQ ID NO:5+Probe No. 5) formed after 30 minutes or 60 minutes of incubation in the presence of 10 mM $MgCl_2$ and 10 mM $MnCl_2$ resulted in fluorescent emissions consistent with the destruction of these complexes at a rate characteristic for DNA complexes containing an antiparallel ssDNA probe (FIG. 14B). When a subsequent measurement was made at 45 minutes after lasing of the perfectly complementary complex at 30 minutes, the emission intensity level was 1869, testimony to the rapidity with which the complex was destroyed (data not shown). The level of fluorescent emission, after multiple lasing, returned to the cationically quenched values observed by the uncomplexed Probe No. 5 alone control (compare FIGS. 14A and 14B). The only exception was the perfectly matched complexes formed after 15 minutes of incubation and repeatedly irradiated thereafter (FIG. 14B). In this case the fluorescent emission was not consistent with the destruction of the complexes (FIG. 14B), even though further cationic quench of Probe No. 5, when multiply irradiated after a 15 minute incubation, was totally inhibited (FIG. 14A). DsDNA:ssDNA complexes containing a 1 bp T-G mismatch (SEQ ID NO:7+Probe No. 5) were similarly apparently destroyed by multiple lasing (FIG. 14C).

An experiment was performed to determine the basis for the effect of multiple lasing on the complexes. It was found that when fresh cations were added to the reaction mixture which had been lased twice, the inhibition of cationic quench in fluorescence emitted by the ssDNA-F probe could not be reversed and further cationic quench did not occur upon further incubation, strongly suggesting that the ssDNA-F probe was inactivated by multiple irradiation, by a yet unknown mechanism (data not shown). Similarly, when fresh ssDNA-F probes were added to the reaction mixture which had been lased twice, after normalizing for the increased fluorescent emission of the fresh probe, no subsequent progressive cationic quenching was observed upon further incubation of the reaction mixture, strongly suggesting that the lased cations were somehow disabled (data not shown).

In the foregoing examples and description, we have elucidated that heteropolymeric nucleic acid strands can specifically bind on the basis of homologous base pairing. Such binding can occur between parallel or antiparallel strands.

We have also elucidated that nucleic acid bases bound in a Watson-Crick complementary duplex are not quiescent as regards the bases of proximal nucleic acid strands and that such bases can be interacted with on the basis of Watson-Crick complementary base pairing or homologous base pairings, depending on the binding potential of the proximal sequence of bases determined by either of the possible binding motifs. This is true whether the bases in the duplex are interacting with bases in a third strand to form a specifically bound triplex structure or whether the bases of the duplex are specifically interacting with proximal bases which are themselves coupled into a Watson-Crick complementary duplex. Accordingly the invention comprises the discovery that Watson-Crick coupled bases remain reactive as specific bases to interact and bind to proximal bases on other strands and do so with great specificity and alacrity. While all of this is remarkable, it is considered especially remarkable that A:T and G:C pairings are detected as mismatches in binding reactions wherein the homologous binding motif is dominant and being enforced on all base pairs by a strand-wide imperative. It is likewise remarkable that homologous quadruplex binding is more specific than is Watson-Crick complementary quadruplex binding. Of necessity quadruplex binding occurs between the major groove side of a duplex-coupled base or base pair and the minor groove side of a duplex-coupled base or base pair. Heretofore, while the potential of further binding by a base already complexed in a duplex was unknown, it had been postulated that third strand recognition of bases in a duplex occurred solely in the major groove of the duplex. This we show is not the case. We have also demonstrated that putative backbone repulsion is no barrier to duplex:duplex interaction.

Our invention relates to readily achieved binding reactions which are typically achieved with short incubation periods at room temperature and which do not depend on molar excess of a reagent to drive a reaction. Accordingly the invention is shown to be not only readily achieved, but obviously biologically relevant.

Finally we have shown that partial Watson-Crick complementary conjugation with free bases can contribute to increased duplex binding and increased specificity.

The invention constitutes a substantial addition to the knowledge of base binding and as such will be central to the elucidation of many biological functions whose mechanisms are currently mysterious, such as gene silencing.

It is most remarkable to detect specific homologous recognition and binding by bases previously and stably coupled into Watson-Crick complementary duplex.

We believe that what we have elucidated will require the abandonment of many "canonical" ideas and the reopening of the question of nucleic acid binding capability.

While the invention has been described in detail and with reference to specific examples thereof, it will be apparent to one skilled in the art that various changes and modifications can be made therein without departing from the spirit and scope thereof.

What is claimed is:

1. A complex comprising:
a probe containing a heteropolymeric probe sequence of nucleic acids or nucleic acid analogues containing purines and pyrimidines; and
a target containing a heteropolymeric target sequence of nucleic acids or nucleic acid analogues containing purines and pyrimidines, wherein:
(a) at least one of said probe and said target is purified or synthetic;
(b) bonding of said heteropolymeric probe sequence to said heteropolymeric target sequence consists of:
(i) Watson-Crick bonds between each pyrimidine of the heteropolymeric probe sequence and each opposing purine of the heteropolymeric target sequence, and between each purine of the heteropolymeric probe sequence and each opposing pyrimidine of the heteropolymeric target sequence; or
(ii) homologous bonds between each pyrimidine of the heteropolymeric probe sequence and each opposing pyrimidine of the heteropolymeric target sequence, and between each purine of the heteropolymeric probe sequence and each opposing purine of the heteropolymeric target sequence;
and
(c) all bases of said probe and said target are selected from the group consisting of A, T, G, C and U, provided that when said complex is a duplex and said heteropolymeric probe sequence is antiparallel to said heteropolymeric target sequence, said heteropolymeric probe sequence is bonded to said heteropolymeric target sequence by homologous base interaction, and provided that when said complex is a triplex, said complex is free of recombination proteins.

2. A complex comprising:
a probe containing a heteropolymeric probe sequence of nucleic acids or nucleic acid analogues; and
a target containing a heteropolymeric target sequence of nucleic acids or nucleic acid analogues,
wherein: (a) at least one of said probe and said target is purified or synthetic; (b) said complex is a duplex; (c) said heteropolymeric probe sequence and said heteropolymeric target sequence have parallel directionality; and (d) said heteropolymeric probe sequence is bonded to said heteropolymeric target sequence by Watson-Crick complementary base interaction.

3. The complex of claim 1, wherein one of said probe and said target is single stranded, the other of said probe and said target is double-stranded, and said complex is a triplex.

4. The complex of claim 3, wherein said complex is free of PNA.

5. The complex of claim 3, wherein said heteropolymeric probe sequence and said heteropolymeric target sequence have parallel directionality, and said heteropolymeric probe sequence is bonded to said heteropolymeric target sequence by homologous base interaction.

6. The complex of claim 3, wherein said heteropolymeric probe sequence and said heteropolymeric target sequence have parallel directionality, and said heteropolymeric probe sequence is bonded to said heteropolymeric target sequence by Watson-Crick complementary base interaction.

7. The complex of claim 3, wherein: (a) said heteropolymeric probe sequence and said heteropolymeric target sequence have parallel directionality; (b) said target includes a first strand containing said heteropolymeric target sequence and a second strand containing a second heteropolymeric target sequence complementary and antiparallel to said heteropolymeric target sequence; and (c) said heteropolymeric probe sequence is bonded to said heteropolymeric target sequence by homologous base interaction and said heteropolymeric probe sequence is bonded to said second heteropolymeric target sequence by Watson-Crick complementary base interaction.

8. The complex of claim 3, wherein said heteropolymeric probe sequence and said heteropolymeric target sequence have antiparallel directionality, and said heteropolymeric probe sequence is bonded to said heteropolymeric target sequence by homologous base interaction.

9. The complex of claim 3, wherein said heteropolymeric probe sequence and said heteropolymeric target sequence have antiparallel directionality, and said heteropolymeric probe sequence is bonded to said heteropolymeric target sequence by Watson-Crick complementary base interaction.

10. The complex of claim 3, wherein: (a) said heteropolymeric probe sequence and said heteropolymeric target sequence have antiparallel directionality; (b) said target includes a first strand containing said heteropolymeric target sequence and a second strand containing a second heteropolymeric target sequence complementary and antiparallel to said heteropolymeric target sequence; and (c) said heteropolymeric probe sequence is bonded to said heteropolymeric target sequence by homologous base interaction and said heteropolymeric probe sequence is bonded to said second heteropolymeric target sequence by Watson-Crick complementary base interaction.

11. A complex comprising:
  a probe containing a heteropolymeric probe sequence of nucleic acids or nucleic acid analogues; and
  a target containing a heteropolymeric target sequence of nucleic acids or nucleic acid analogues,
  wherein: (a) at least one of said probe and said target is purified or synthetic; (b) said heteropolymeric probe sequence is bonded to said heteropolymeric target sequence by Watson-Crick complementary base interaction or by homologous base interaction; and (c) said probe and said target are double stranded and said complex is a quadruplex.

12. The complex of claim 11, wherein said complex is free of PNA.

13. The complex of claim 11, wherein said heteropolymeric probe sequence and said heteropolymeric target sequence have parallel directionality, and said heteropolymeric probe sequence is bonded to said heteropolymeric target sequence by homologous base interaction.

14. The complex of claim 11, wherein said heteropolymeric probe sequence and said heteropolymeric target sequence have parallel directionality, and said heteropolymeric probe sequence is bonded to said heteropolymeric target sequence by Watson-Crick complementary base interaction.

15. The complex of claim 11, wherein: (a) said heteropolymeric probe sequence and said heteropolymeric target sequence have parallel directionality; (b) said probe includes a first probe strand containing said heteropolymeric probe sequence and a second probe strand containing a second heteropolymeric probe sequence complementary and antiparallel to said heteropolymeric probe sequence; (c) said target includes a first target strand containing said heteropolymeric target sequence and a second target strand containing a second heteropolymeric target sequence complementary and antiparallel to said heteropolymeric target sequence; and (d) said heteropolymeric probe sequence is bonded to said heteropolymeric target sequence by homologous base interaction and said heteropolymeric probe sequence is optionally bonded to said second heteropolymeric target sequence by Watson-Crick complementary base interaction.

16. The complex of claim 11, wherein: (a) said heteropolymeric probe sequence and said heteropolymeric target sequence have parallel directionality; (b) said probe includes a first probe strand containing said heteropolymeric probe sequence and a second probe strand containing a second heteropolymeric probe sequence complementary and antiparallel to said heteropolymeric probe sequence; (c) said target includes a first target strand containing said heteropolymeric target sequence and a second target strand containing a second heteropolymeric target sequence complementary and antiparallel to said heteropolymeric target sequence; and (d) said heteropolymeric probe sequence is bonded to said heteropolymeric target sequence by Watson-Crick complementary base interaction and said heteropolymeric probe sequence is optionally bonded to said second heteropolymeric target sequence by homologous base interaction.

17. The complex of claim 11, wherein: (a) said heteropolymeric probe sequence and said heteropolymeric target sequence have antiparallel directionality; (b) said probe includes a first probe strand containing said heteropolymeric probe sequence and a second probe strand containing a second heteropolymeric probe sequence complementary and antiparallel to said heteropolymeric probe sequence; (c) said target includes a first target strand containing said heteropolymeric target sequence and a second target strand containing a second heteropolymeric target sequence complementary and antiparallel to said heteropolymeric target sequence; and (d) said heteropolymeric probe sequence is bonded to said heteropolymeric target sequence by homologous base interaction and said heteropolymeric probe sequence is optionally bonded to said second heteropolymeric target sequence by Watson-Crick complementary base interaction.

18. The complex of claim 11, wherein: (a) said heteropolymeric probe sequence and said heteropolymeric target sequence have antiparallel directionality; (b) said probe includes a first probe strand containing said heteropolymeric probe sequence and a second probe strand containing a second heteropolymeric probe sequence complementary and antiparallel to said heteropolymeric probe sequence; (c) said target includes a first target strand containing said heteropolymeric target sequence and a second target strand containing a second heteropolymeric target sequence complementary and antiparallel to said heteropolymeric target sequence; and (d) said heteropolymeric probe sequence is bonded to said heteropolymeric target sequence by Watson-Crick complementary base interaction and said heteropolymeric probe sequence is optionally bonded to said second heteropolymeric target sequence by homologous base interaction.

19. The complex of claim 1, wherein said probe occupies a minor groove of said target.

20. The complex of claim 1, wherein said probe occupies a major groove of said target.

21. The complex of claim 3, wherein bases of said probe interact with bases of both strands of said target simultaneously.

22. The complex of claim 11, wherein bases of said probe interact with bases of both strands of said target simultaneously.

23. The complex of claim 1, wherein a backbone of the probe comprises deoxyribose phosphate.

24. The complex of claim 1, wherein a backbone of the probe is uncharged, partially negatively charged, or positively charged.

25. The complex of claim 1, wherein at least one base in said probe is a synthetic analogue of a naturally occurring base having specific binding affinities based on Watson-Crick complementarity or homologous binding.

26. A complex comprising:
a probe containing a heteropolymeric probe sequence of nucleic acids or nucleic acid analogues: and
a target containing a heteropolymeric target sequence of nucleic acids or nucleic acid analogues.
wherein: (a) at least one of said probe and said target is purified or synthetic; (b) said heteropolymeric probe sequence is bonded to said heteropolymeric target sequence by base interaction between bases of said probe and bases of said target, said base interaction being Watson-Crick complementary base interaction or homologous base interaction; (c) the probe further contains a loop and a stem adjacent to the loop; (d) the heteropolymeric probe sequence is located partially or entirely within the stem; and (e) each of the loop and the stem comprises nucleic acids or nucleic acid analogues, provided that when said complex is a duplex and said heteropolymeric probe sequence is antiparallel to said heteropolymeric target sequence, said heteropolymeric probe sequence is bonded to said heteropolymeric target sequence by homologous base interaction, and provided that when said complex is a triplex, said complex is free of recombination proteins.

27. A method for making a complex of claim 1, said method comprising:
providing a sample comprising the target containing the heteropolymeric target sequence of nucleic acids or nucleic acid analogues;
providing the probe, wherein: (a) the probe further contains a loop and a stem adjacent to the loop; (b) the heteropolymeric probe sequence is located within at least one of the loop and the stem; and (c) each of the loop and the stem comprises nucleic acids or nucleic acid analogues; and
forming a reaction mixture comprising the probe and the target under conditions that the probe and the target hybridize to form the complex.

28. The method of claim 27, further comprising detecting a signal correlated with a binding affinity between the probe and the target such that the target is detected.

29. The method of claim 28, wherein a match or a mismatch between bases of the heteropolymeric probe sequence and bases of the heteropolymeric target sequence is detected.

30. The method of claim 27, wherein the probe and the target hybridize to form a duplex.

31. The method of claim 27, wherein one of the heteropolymeric probe sequence and the heteropolymeric target sequence is single stranded, the other of the heteropolymeric probe sequence and the heteropolymeric target sequence is double-stranded, and the probe and the target hybridize to form a triplex.

32. The method of claim 27, wherein the heteropolymeric probe sequence and the heteropolymeric target sequence are double stranded and the probe and the target hybridize to form a quadniplex.

33. The method of claim 27, wherein: (a) homologous binding conditions are provided and an incompletely homologous probe does not bind to the target or binds to the target with reduced efficiency; or (b) Watson-Crick complementary binding conditions are provided and an incompletely complementary probe does not bind to the target or binds to the target with reduced efficiency.

34. The method of claim 27, wherein the heteropolymeric probe sequence is located in the stem.

35. The method of claim 27, wherein the heteropolymeric probe sequence is located in the loop.

36. The method of claim 35, wherein: (a) the stem comprises at least two strands of nucleic acids or nucleic acid analogues, (b) the at least two strands are adapted to be bound to each other in the absence of the heteropolymeric target sequence binding to the heteropolymeric probe sequence, and (c) the at least two strands are adapted to separate from each other when the heteropolymeric target sequence binds to the heteropolymeric probe sequence.

37. The method of claim 36, wherein: (a) one of the at least two strands comprises a donor; (b) an opposing one of the at least two strands comprises an acceptor; and (c) the method further comprises detecting a change in a signal when the heteropolymeric target sequence binds to the heteropolymeric probe sequence and the at least two strands separate from each other.

38. The method of claim 37, wherein: (a) the donor emits the signal and the acceptor quenches the signal; or (b) the donor transfers energy to the acceptor and the acceptor emits the signal.

39. The method of claim 38, wherein the energy transferred is fluorescent resonance energy.

40. The method of claim 38, wherein the signal is chemiluminescent.

41. The complex of claim 1, wherein: (a) the probe is a heteropolymeric multistranded parallel complex; (b) bases of the probe are homologously bound in a first plane; (c) the target is a heteropolyineric multistranded parallel complex; and (d) bases of the target are homologously bound in a second plane.

42. The complex of claim 1, wherein: (a) the probe is a heteropolymeric multistranded parallel complex; (b) bases of the probe are bound pursuant to a Watson-Crick motif in a first plane; (c) the target is a heteropolymeric multistranded parallel complex; and (d) bases of the target are bound pursuant to a Watson-Crick motif in a second plane.

43. An isolated or synthetic probe comprising:
a loop containing nucleic acids or nucleic acid analogues;
a stem adjacent to the loop, and containing at least two strands of nucleic acids or nucleic acid analogues; and
a heteropolymeric probe sequence located entirely or partially within the loop, and containing a double or triple-stranded sequence of nucleic acids or nucleic acid analogues,
wherein the at least two strands of the stem are adapted to be bound to each other in the absence of the heteropolymeric target sequence binding to the heteropolymeric probe sequence, and the at least two strands are adapted to separate from each other and open the loop when a heteropolymeric target sequence binds to the heteropolymeric probe sequence.

44. The complex of claim 11, wherein said complex is free of Hoogsteen binding and free of G-G quartets.

45. A complex comprising:
a probe containing a heteropolymeric probe sequence of nucleic acids or nucleic acid analogues; and
a target containing a heteropolymeric target sequence of nucleic acids or nucleic acid analogues, wherein:
(a) at least one of said probe and said target is purified or synthetic;
(b) bonding of said heteropolymeric probe sequence to said heteropolymeric target sequence consists of:
(i) Watson-Crick bonds comprising at least two members selected from the group consisting of an A-T bond, an A-U bond, and a G-C bond, or (ii) homologous bonds comprising at least four members selected from the group consisting of an A-A bond, a T-T bond, a G-G bond, a C-C bond and a U-U bond;
and
(c) all bases of said probe and said target are selected from the group consisting of A, T, G, C and U, provided that when said complex is a duplex and said heteropolymeric probe sequence is antiparallel to said heteropolymeric target sequence, said heteropolymeric probe sequence is bonded to said heteropolymeric target sequence by homologous base interaction, and provided that when said complex is a triplex, said complex is free of recombination proteins.

46. The complex of claim 11, wherein said heteropolymeric probe sequence comprises purines and pyrimidines, said heteropolymeric target sequence comprises purines and pyrimidines, all bases of said probe and said target are selected from the group consisting of A, T, G, C and U, and bonding of said heteropolymeric probe sequence to said heteropolymeric target sequence consists of:
   (i) Watson-Crick bonds between each pyrimidine of the heteropolymeric probe sequence and each opposing purine of the heteropolymeric target sequence, and between each purine of the heteropolymeric probe sequence and each opposing pyrimidine of the heteropolymeric target sequence; or
   (ii) homologous bonds between each pyrimidine of the heteropolymeric probe sequence and each opposing pyrimidine of the heteropolymeric target sequence, and between each purine of the heteropolymeric probe sequence and each opposing purine of the heteropolymeric target sequence.

47. The complex of claim 26, wherein said heteropolymeric probe sequence comprises purines and pyrimidines, said heteropolymeric target sequence comprises purines and pyrimidines, all bases of said probe and said target are selected from the group consisting of A, T, G, C and U, and bonding of said heteropolymeric probe sequence to said heteropolymeric target sequence consists of:
   (i) Watson-Crick bonds between each pyrimidine of the heteropolymeric probe sequence and each opposing purine of the heteropolymeric target sequence, and between each purine of the heteropolymeric probe sequence and each opposing pyrimidine of the heteropolymeric target sequence; or
   (ii) homologous bonds between each pyrimidine of the heteropolymeric probe sequence and each opposing pyrimidine of the heteropolymeric target sequence, and between each purine of the heteropolymeric probe sequence and each opposing purine of the heteropolymeric target sequence.

* * * * *

UNITED STATES PATENT AND TRADEMARK OFFICE
CERTIFICATE OF CORRECTION

PATENT NO.         : 7,309,569 B2
APPLICATION NO.    : 10/293148
DATED              : December 18, 2007
INVENTOR(S)        : Glen H. Erikson et al.

Page 1 of 1

It is certified that error appears in the above-identified patent and that said Letters Patent is hereby corrected as shown below:

In the Claims

Col. 45, line 56, change "quadniplex" to --quadruplex--.

Col. 46, line 28, change "heteropolyineric" to --heteropolymeric--.

Signed and Sealed this

Twenty-ninth Day of April, 2008

JON W. DUDAS
*Director of the United States Patent and Trademark Office*

SEQUENCE LISTING

<160> NUMBER OF SEQ ID NOS: 24

<210> SEQ ID NO 1
<211> LENGTH: 50
<212> TYPE: DNA
<213> ORGANISM: Exon 10 of Human Cystic Fibrosis Gene

<400> SEQUENCE: 1
tggcaccatt aaagaaaata tcatctttgg tgtttcctat gatgaatata          50

<210> SEQ ID NO 2
<211> LENGTH: 50
<212> TYPE: DNA
<213> ORGANISM: Exon 10 of Human Cystic Fibrosis Gene

<400> SEQUENCE: 2
tggcaccatt aaagaaaata tcgtctttgg tgtttcctat gatgaatata          50

<210> SEQ ID NO 3
<211> LENGTH: 50
<212> TYPE: DNA
<213> ORGANISM: Exon 10 of Human Cystic Fibrosis Gene

<400> SEQUENCE: 3
tggcaccatt aaagaaaata tactctttgg tgtttcctat gatgaatata          50

<210> SEQ ID NO 4
<211> LENGTH: 50
<212> TYPE: DNA
<213> ORGANISM: Exon 10 of Human Cystic Fibrosis Gene

<400> SEQUENCE: 4
tggcaccatt aaagaaaata tacgctttgg tgtttcctat gatgaatata          50

<210> SEQ ID NO 5
<211> LENGTH: 50
<212> TYPE: DNA
<213> ORGANISM: Exon 10 of Human Cystic Fibrosis Gene

<400> SEQUENCE: 5
gagcaccatg acagacactg tcatctctgg tgtgtcctac gatgactctg          50

<210> SEQ ID NO 6
<211> LENGTH: 50
<212> TYPE: DNA
<213> ORGANISM: Exon 10 of Human Cystic Fibrosis Gene

<400> SEQUENCE: 6
gagcaccatg acagacactg tcgtctctgg tgtgtcctac gatgactctg          50

<210> SEQ ID NO 7
<211> LENGTH: 50
<212> TYPE: DNA
<213> ORGANISM: Exon 10 of Human Cystic Fibrosis Gene

<400> SEQUENCE: 7
gagcaccatg acagacactg tcatctttgg tgtgtcctac gatgactctg          50

<210> SEQ ID NO 8
<211> LENGTH: 50
<212> TYPE: DNA
<213> ORGANISM: Exon 10 of Human Cystic Fibrosis Gene -continued

```
<400> SEQUENCE: 8
gagcaccatg acagacactg tactctctgg tgtgtcctac gatgactctg          50

<210> SEQ ID NO 9
<211> LENGTH: 47
<212> TYPE: DNA
<213> ORGANISM: Exon 10 of Human Cystic Fibrosis Gene

<400> SEQUENCE: 9
tggcaccatt aaagaaaata tcattggtgt ttcctatgat gaatata            47

<210> SEQ ID NO 10
<211> LENGTH: 50
<212> TYPE: DNA
<213> ORGANISM: Exon 10 of Human Cystic Fibrosis Gene

<400> SEQUENCE: 10
gagcaccatg acagacactg tcttctctgg tgtgtcctac gatgactctg          50

<210> SEQ ID NO 11
<211> LENGTH: 50
<212> TYPE: DNA
<213> ORGANISM: Exon 10 of Human Cystic Fibrosis Gene

<400> SEQUENCE: 11
gagcaccatg acagacactg tcatccctgg tgtgtcctac gatgactctg          50

<210> SEQ ID NO 12
<211> LENGTH: 15
<212> TYPE: DNA
<213> ORGANISM: Exon 10 of Human Cystic Fibrosis Gene
<220> FEATURE:
<221> NAME/KEY: misc_feature
<222> LOCATION: ()..()
<223> OTHER INFORMATION: 5' end begins with H, 3' end ends with
      lysine-CONH2

<400> SEQUENCE: 12
caccaaagat gatat                                               15

<210> SEQ ID NO 13
<211> LENGTH: 15
<212> TYPE: DNA
<213> ORGANISM: Exon 10 of Human Cystic Fibrosis Gene
<220> FEATURE:
<221> NAME/KEY: misc_feature
<222> LOCATION: ()..()
<223> OTHER INFORMATION: 5' end begins with H, 3' end ends with
      lysine-CONH2

<400> SEQUENCE: 13
tatagtagaa accac                                               15

<210> SEQ ID NO 14
<211> LENGTH: 15
<212> TYPE: DNA
<213> ORGANISM: Exon 10 of Human Cystic Fibrosis Gene

<400> SEQUENCE: 14
caccagagat gacag                                               15

<210> SEQ ID NO 15
<211> LENGTH: 15
<212> TYPE: DNA
<213> ORGANISM: Exon 10 of Human Cystic Fibrosis Gene
```

```
<400> SEQUENCE: 15
gacagtagag accac                                                    15

<210> SEQ ID NO 16
<211> LENGTH: 15
<212> TYPE: DNA
<213> ORGANISM: Exon 10 of Human Cystic Fibrosis Gene
<220> FEATURE:
<221> NAME/KEY: misc_feature
<222> LOCATION: ()..()
<223> OTHER INFORMATION: fluorescein moiety attached at the 5' position

<400> SEQUENCE: 16
caccagagat gacag                                                    15

<210> SEQ ID NO 17
<211> LENGTH: 15
<212> TYPE: DNA
<213> ORGANISM: Exon 10 of Human Cystic Fibrosis Gene
<220> FEATURE:
<221> NAME/KEY: misc_feature
<222> LOCATION: ()..()
<223> OTHER INFORMATION: fluorescein moiety attached at 5' end

<400> SEQUENCE: 17
gacagtagag accac                                                    15

<210> SEQ ID NO 18
<211> LENGTH: 15
<212> TYPE: DNA
<213> ORGANISM: Exon 10 of Human Cystic Fibrosis Gene
<220> FEATURE:
<221> NAME/KEY: misc_feature
<222> LOCATION: ()..()
<223> OTHER INFORMATION: fluorescein moiety attached at 5' end

<400> SEQUENCE: 18
caccaaagat gatat                                                    15

<210> SEQ ID NO 19
<211> LENGTH: 15
<212> TYPE: DNA
<213> ORGANISM: Exon 10 of Human Cystic Fibrosis Gene

<400> SEQUENCE: 19
caccaaagat gatat                                                    15

<210> SEQ ID NO 20
<211> LENGTH: 15
<212> TYPE: DNA
<213> ORGANISM: Exon 10 of Human Cystic Fibrosis Gene

<400> SEQUENCE: 20
cacgaaagat gatat                                                    15

<210> SEQ ID NO 21
<211> LENGTH: 15
<212> TYPE: DNA
<213> ORGANISM: Exon 10 of Human Cystic Fibrosis Gene

<400> SEQUENCE: 21
caccaaacat gatat                                                    15
```

```
<210> SEQ ID NO 22
<211> LENGTH: 15
<212> TYPE: DNA
<213> ORGANISM: Exon 10 of Human Cystic Fibrosis Gene
<220> FEATURE:
<221> NAME/KEY: misc_feature
<222> LOCATION: ()..()
<223> OTHER INFORMATION: fluorescein moiety attached at 5' end

<400> SEQUENCE: 22
ctgtcatctc tggtg                                                15

<210> SEQ ID NO 23
<211> LENGTH: 15
<212> TYPE: DNA
<213> ORGANISM: Exon 10 of Human Cystic Fibrosis Gene

<400> SEQUENCE: 23
ctgtcatctc tggtg                                                15

<210> SEQ ID NO 24
<211> LENGTH: 15
<212> TYPE: DNA
<213> ORGANISM: Exon 10 of Human Cystic Fibrosis Gene

<400> SEQUENCE: 24
gacagtagag accac                                                15
```